United States Patent
Beutler et al.

(10) Patent No.: US 10,287,297 B2
(45) Date of Patent: May 14, 2019

(54) EPOXYAZULENE DERIVATIVES USEFUL FOR TREATING CANCER AND DIABETES

(71) Applicants: The United States of America, as represented by the Secretary, Department of Heatlh and Human Services, Washington, DC (US); Fundació Institut Català d'Investigació Química (ICIQ), Tarragona (ES); Universitat Rovira i Virgili, Tarragona (ES)

(72) Inventors: John A. Beutler, Union Bridge, MD (US); Antonio M. Echavarren, Tarragona (ES); Laura Lopez, Barcelona (ES); Fernando Bravo, Valls (ES); Lorena Riesgo, El Bérrón (ES); Tanya Tannaquil Ransom, Germantown, MD (US)

(73) Assignees: The United States of America, as represented by the Secretary, Department of Health and Human Services, Washington, DC (US); Fundació Institut Català d'Investigació Quimica (ICIQ), Tarragona (ES); Universitat Rovira i Virgili, Tarragona (ES)

( * ) Notice: Subject to any disclaimer, the term of this patent is extended or adjusted under 35 U.S.C. 154(b) by 0 days.

(21) Appl. No.: 15/564,353

(22) PCT Filed: Apr. 13, 2016

(86) PCT No.: PCT/US2016/027262
§ 371 (c)(1),
(2) Date: Oct. 4, 2017

(87) PCT Pub. No.: WO2016/168281
PCT Pub. Date: Oct. 20, 2016

(65) Prior Publication Data
US 2018/0127433 A1    May 10, 2018

Related U.S. Application Data

(60) Provisional application No. 62/146,805, filed on Apr. 13, 2015.

(51) Int. Cl.
C07D 493/08    (2006.01)
A61P 35/02     (2006.01)
C07D 487/08    (2006.01)
C07D 495/08    (2006.01)
A61P 3/10      (2006.01)

(52) U.S. Cl.
CPC ............ C07D 493/08 (2013.01); A61P 3/10 (2018.01); A61P 35/02 (2018.01); C07D 487/08 (2013.01); C07D 495/08 (2013.01)

(58) Field of Classification Search
CPC .. C07D 493/08; C07D 487/08; C07D 495/08; A61P 35/02; A61P 3/10
USPC ........................................................ 514/468
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985  | Geho et al. |
| 4,837,028 A | 6/1989  | Allen |
| 5,019,369 A | 5/1991  | Presant et al. |
| 8,410,292 B2 | 4/2013 | Beutler et al. |

FOREIGN PATENT DOCUMENTS

| | | |
|---|---|---|
| WO | WO 2009/088854 A1 | 7/2009 |
| WO | WO 2011/120886 A1 | 10/2011 |
| WO | WO 2012/084267 A1 | 6/2012 |
| WO | WO 2013/106226 A2 | 7/2013 |
| WO | WO 2014/078350 A1 | 5/2014 |

OTHER PUBLICATIONS

Akbulut et al., "(−)-Englerin A is a Potent and Selective Activator of TRPC4 and TRPC5 Calcium Channels," *Angew. Chem. Int. Ed. Engl.*, 54: 3787-3791 (2015).
Akee et al., "Chlorinated Englerins with Selective Inhibition of Renal Cancer Cell Growth," *J. Nat. Prod.*, 75: 459-463 (2012).
Amijs et al., "Gold(I)-Catalyzed Intermolecular Addition of Carbon Nucleophiles to 1,5- and 1,6-Enynes," *J. Org. Chem.*, 73: 7721-7730 (2008).
Carson et al., "Englerin A agonizes the TRPC4/C5 cation channels to inhibit tumor cell line proliferation," *PLoS One*, DOI:10.1371/journale/pone.0127498, 21 pages (2015).
Chemical Abstracts No. 1359266, 2006.
Chan et al., "Chemical Synthesis and Biological Evaluation of the Englerin Analogues," *Chem. Med. Chem.*, 6(3): 420-423 (2011).
Docherty, "Totally Synthetic," Royal Society of Chemistry, pp. 1-2, May 2010.

(Continued)

*Primary Examiner* — Rita J Desai
(74) *Attorney, Agent, or Firm* — Leydig, Voit & Mayer, Ltd.

(57) ABSTRACT

Disclosed is a compound of formula (I) in which $R^1$-$R^5$ and $X^1$ are as described herein. Also provided are methods of using a compound of formula (I), including a method of treating cancer and a method of treating diabetes.

19 Claims, 25 Drawing Sheets

(56) References Cited

OTHER PUBLICATIONS

Dong et al., "Total synthesis of (+/−)-4-demethylenglerin A," *J. Asian Nat. Prod. Res.*, 16: 629-639 (2014).
Fash et al., "Synthesis of a Stable and Orally Bioavailable Englerin Analogue," *Bioorg. Med. Chem. Lett.*, 26(11): 2641-2644 (2016).
Ferrer et al., "Missing cyclization pathways and new rearrangements unveiled in the gold(I) and platinum(II)-catalyzed cyclization of 1,6-enynes," *Tetrahedron*, 63: 6306-6316 (2007).
Gaunt et al., "Transient receptor potential canonical 4 and 5 proteins as targets in cancer therapeutics," *Eur. Biophys. J.*, 45: 611-620 (2016).
International Preliminary Report on Patentability, PCT/US2016/027262, WIPO, dated Oct. 17, 2017.
International Search Report, European Patent Office, PCT/US2016/027262, dated Jul. 6, 2016.
Lopez-Suarez et al., "Biological Evaluation of New (−)-Englerin Analogues," *ChemMedChem*, 11(9): 1003-1007, 2016.
Ludlow et al., "(−)-Englerin A-evoked Cytotoxicity Is Mediated by Na$^+$ Influx and Counteracted by Na$^+$/K$^+$-ATPase," *J. Biol. Chem.*, 292(2): 723-731 (Nov. 14, 2016).
Mohapatra et al., "A Short and Efficient Synthetic Strategy for the Total Syntheses of (S)-(+)- and (R)-(−)-Plakolide A," *Eur. J. Org. Chem.*, 5059-5063 (2007).
Molawi et al., "Enantioselective Synthesis of (−)-Englerins A and B," *Angew. Chem. Int. Ed.*, 49: 3517-3519 (2010).
Molawi et al., "Enantioselective Synthesis of (−)-Englerins A and B," *Angew. Chem. Int. Ed.*, 122: 3595-3597 (2010).
Nakatsuji et al., "General, Robust, and Stereocomplementary Preparation of β-Ketoester Enol Tosylates as Cross-Coupling Partners Utilizing TsCI-N-Methylimidazole Agents," *Org. Lett.*, 10(11): 2131-2134 (2008).
Nicolaou et al., "Total Synthesis of Englerin A," *J. Am. Chem. Soc.*, 132: 8219-8222 (2010).
Paek et al., "Preparative isolation of aldose reductase inhibitory compounds from *Nardostachys chinensis* by elution-extrusion countercurrent chromatography," *Arch. Pharm. Res.*, 37(10): 1271-1279 (2014).
Radtke et al., "Total Synthesis and Biological Evaluation of (−)-Englerin A and B: Synthesis of Analogues with Improved Activity Profile," *Angew. Chem. Int. Ed.*, 50: 3998-4002 (2011).
Ratnayake et al., "Englerin A, a Selective Inhibitor of Renal Cancer Cell Growth, from *Phyllanthus engleri*," *Organic Letters*, 11(1): 57-60 (2008).
Riou et al., "De Novo Synthesis of (+)-Isofregenedol," *J. Org. Chem.*, 73: 7436-7439 (2008).
Shoemaker, "The NCI60 Human tumour cell line anticancer drug screen," *Nat Rev Cancer*, 6(10): 813-23 (2006).
Sourbier et al., "Englerin A Stimulates PKCθ to Inhibit Insulin Signaling and to Simultaneously Activate HFS1: Pharmacologically Induced Synthetic Lethality," *Cancer Cell*, 23: 228-237 (Feb. 11, 2013).
Veliceasa et al., "Transient potential receptor channel 4 controls thrombospondin-1 secretion and angiogenesis in renal cell carcinoma," *FEBS J*, 274: 6365-6377 (2007).
Written Opinion of the International Searching Authority, European Patent Office, PCT/US2016/027262, dated Jul. 6, 2016.
Xu et al., "Enantioselective Formal Synthesis of (−)-Englerin A via a Rh-catalyzed [4+3] Cycloaddition Reaction," *Organic Letters*, 12(16): 3708-3711 (2010).
Xu et al., "Formal Synthesis of (−)-Englerin A and Cytotoxicity Studies of Truncated Englerins," *Chem Asian J.*, 7(5): 1052-1060 (2012).

EPOXYAZULENE DERIVATIVES USEFUL FOR TREATING CANCER AND DIABETES

CROSS-REFERENCE TO RELATED APPLICATIONS

This patent application is a U.S. national phase of International patent Application No. PCT/US2016/027262, filed Apr. 12, 2016, which claims the benefit of U.S. Provisional Patent Application No. 62/146,805, filed Apr. 13, 2015, the disclosures of which are incorporated by reference for all purposes.

STATEMENT REGARDING FEDERALLY SPONSORED RESEARCH AND DEVELOPMENT

This invention was made with Government support under Contract Number ZIA 1ZIABC01147001 awarded by the National Institutes of Health, National Cancer Institute. The Government has certain rights in this invention.

BACKGROUND OF THE INVENTION

Cancer is a major cause of death; for example, renal cancer is an important contributor to morbidity and mortality. Current therapies are lacking due to incomplete therapeutic responses and potential adverse side effects, so new therapies are always sought after (Ratanyake et al., *Organic Letters* 2008, 11, 1, 57-60). Attempts have been made to identify and isolate medicinal products for cancer treatment from plant materials. For example, a large number of *Phyllanthus* species have been found in tropical and subtropical regions of the world and some have been used in traditional medicines. Englerin A and englerin B have been isolated and purified from the root bark and stem bark of the plant *Phyllanthus engleri* Pax (Euphorbiaceae). Since then, englerin compounds and derivatives thereof have been studied as potential therapeutics. See, e.g., International Patent Application WO 2013/106226, International Patent Application WO 2014/078350, International Patent Application WO 2012/084267, Radtke et al., *Angew. Chem. Int. Ed.* 2011, 50, 3998, 49, 3517-3519, Nicolaou et al., *J. Am. Chem. Soc.* 2010, 132, 8219-8222, Akee et al., *J. Nat. Prod.* 2012, 75, 459-463, Xu et al., *Chem. Asian J.* 2012, 7, 1052-1060, and Chan et al., *Chem. Med. Chem.* 2011, 6(3), 420-423.

In one possible mechanism, englerin compounds are believed to bind to and activate protein kinase C theta (PKCθ), an isoform found in T cells, muscle, and kidney cancers. The ability to stimulate PKCθ by englerin compounds leads to, e.g., cell cytotoxicity, insulin inhibition, and selective activation of viral replication in T cells. See, e.g., International Patent Application WO 2014/078350 and Sourbier et al., *Cancer Cell,* 2013, 23(2), 228-337. In another possible mechanism, it is contemplated that englerin A activates transient receptor potential canonical (TRPC) ion channels on kidney cancer cell surfaces, thereby increasing the influx of $Ca^{2+}$ and killing the cancer cells (Akbulut et al., *Angew. Chem. Int. Ed.* 2015, 54, 3787-3791). It is further speculated that TRPC proteins and PKCθ may interact with one another but the specific mechanism of interaction is not yet known.

Thus, there continues to be an unmet need to identify novel englerin derivatives to produce treatments for diseases associated with PKCθ and/or calcium ion channel proteins, such as cancer, particularly renal cancer, and diabetes.

BRIEF SUMMARY OF THE INVENTION

The invention provides a compound of formula (I)

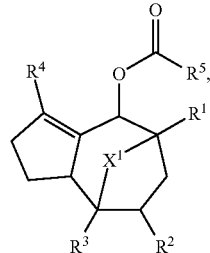

(I)

in which $R^1$-$R^5$ and $X^1$ are as described herein.

The present invention further provides a pharmaceutical composition comprising a compound of the invention and a pharmaceutically acceptable carrier.

The addition of the double bond in the core structure of formula (I) twists the geometry of the core, which might be expected to destroy the therapeutic activity. However it was surprisingly discovered that compounds of formula (I) are therapeutically active, especially against certain cancers, such as renal cancer. This was particularly unexpected, since few modifications of the core sesquiterpene structure have been previously reported, and loss of the five-membered ring or removal of the 4-methyl substituent provides compounds that do not effectively inhibit renal cancer cell growth (Xu et al., *Chem. Asian J.,* 2010, 7, 1052-1060; Dong et al, *J. Asian Nat. Prod. Res.,* 2014, 16, 629-639.). Accordingly, the present invention also provides a method of treating a disease, such as cancer or diabetes, in a mammal in need thereof comprising administering to the mammal an effective amount of the compound.

BRIEF DESCRIPTION OF THE SEVERAL VIEWS OF THE DRAWINGS

FIG. 2 is a chemical scheme of the synthesis of (S,E)-2,6-dimethyl-6-(triethylsilyloxy)oct-2-en-7-ynal 5a.

FIG. 3 is a chemical scheme of the synthesis of compounds of formula (I) starting from (S,E)-2,6-dimethyl-6-(triethylsilyloxy)oct-2-en-7-ynal 5a. FIG. 3A shows steps h-k, whereas

FIG. 4A depicts the dose response curves against leukemia cell lines. FIG. 4B depicts the dose response curves against non-small cell lung cancer cell lines. FIG. 4C depicts the dose response curves against colon cancer cell lines. FIG. 4D depicts dose response curves against ovarian cancer cell lines. FIG. 4E depicts dose response curves against melanoma cell lines. FIG. 4F depicts dose response curves against central nervous system (CNS) cancer cell lines. FIG. 4G depicts dose response curves against renal cancer cell lines. FIG. 4H depicts dose response curves against prostate cancer cell lines. FIG. 4I depicts dose response curves against breast cancer cell lines.

FIG. 5A depicts the dose response curves against leukemia cell lines. FIG. 5B depicts the dose response curves against non-small cell lung cancer cell lines. FIG. 5C depicts the dose response curves against colon cancer cell lines. FIG. 5D depicts dose response curves against ovarian cancer cell lines. FIG. 5E depicts dose response curves against melanoma cell lines. FIG. 5F depicts dose response curves against central nervous system (CNS) cancer cell lines. FIG. 5G depicts dose response curves against renal cancer cell lines. FIG. 5H depicts dose response curves against prostate cancer cell lines. FIG. 5I depicts dose response curves against breast cancer cell lines.

FIG. 6A depicts the dose response curves against leukemia cell lines. FIG. 6B depicts the dose response curves against non-small cell lung cancer cell lines. FIG. 6C depicts the dose response curves against colon cancer cell lines. FIG. 6D depicts dose response curves against ovarian cancer cell lines. FIG. 6E depicts dose response curves against melanoma cell lines. FIG. 6F depicts dose response curves against central nervous system (CNS) cancer cell lines. FIG. 6G depicts dose response curves against renal cancer cell lines. FIG. 6H depicts dose response curves against prostate cancer cell lines. FIG. 6I depicts dose response curves against breast cancer cell lines.

FIGS. 7A-7I depict the dose response curves for a compound formula (I) (i.e (Is)) against various cancer cell lines in the NCI 60-cell test. FIG. 7A depicts the dose response curves against leukemia cell lines. FIG. 7B depicts the dose response curves against non-small cell lung cancer cell lines. FIG. 7C depicts the dose response curves against colon cancer cell lines. FIG. 7D depicts dose response curves against ovarian cancer cell lines. FIG. 7E depicts dose response curves against melanoma cell lines. FIG. 7F depicts dose response curves against central nervous system (CNS) cancer cell lines. FIG. 7G depicts dose response curves against renal cancer cell lines. FIG. 7H depicts dose response curves against prostate cancer cell lines. FIG. 7I depicts dose response curves against breast cancer cell lines.

FIG. 8A depicts the dose response curves against leukemia cell lines. FIG. 8B depicts the dose response curves against non-small cell lung cancer cell lines. FIG. 8C depicts the dose response curves against colon cancer cell lines. FIG. 8D depicts dose response curves against ovarian cancer cell lines. FIG. 8E depicts dose response curves against melanoma cell lines. FIG. 8F depicts dose response curves against central nervous system (CNS) cancer cell lines. FIG. 8G depicts dose response curves against renal cancer cell lines. FIG. 8H depicts dose response curves against prostate cancer cell lines. FIG. 8I depicts dose response curves against breast cancer cell lines.

DETAILED DESCRIPTION OF THE INVENTION

Figure 1:
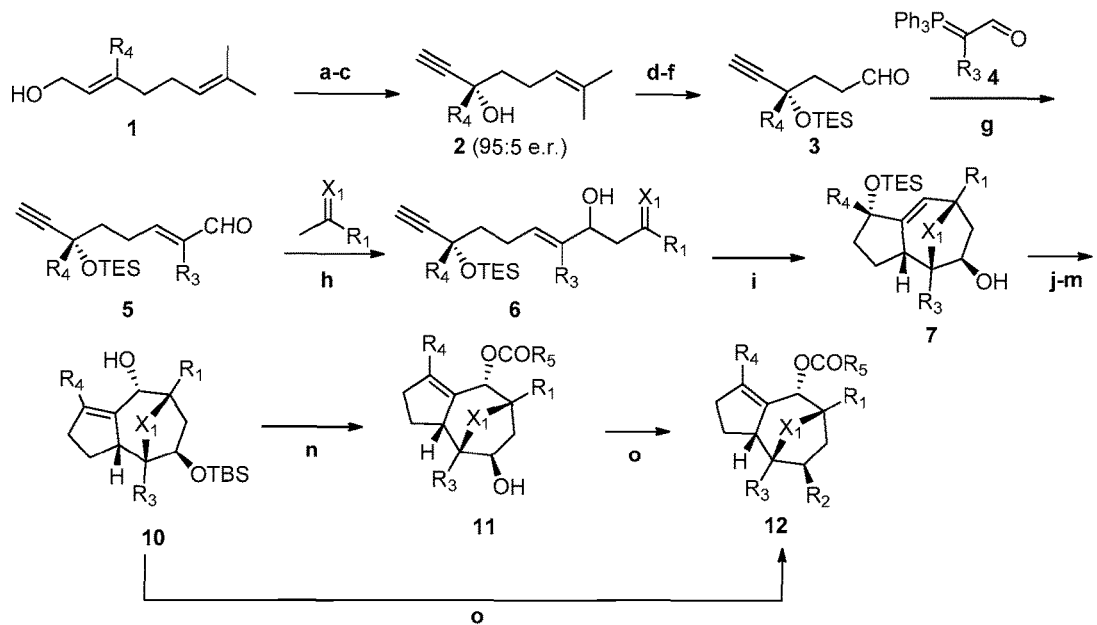
FIG. 1 is a chemical scheme of the synthesis of a compound of formula (I). Reagents and conditions: a) L-(+)-diethyl tartrate, Ti(OiPr)$_4$, tert-butylhydroperoxide, CH$_2$Cl$_2$, −40° C., 4 h, 9:1 e.r.; b) CCl$_4$, PPh$_3$, 80° C., 6 h; c) nBuLi (3.5 equiv), THF, −40° C., 2 h; d) TESOTf, Et$_3$N, CH$_2$Cl$_2$, 23° C., 3 h; e) AD-mix-α, tBuOH/H$_2$O (1:1), 23° C., 10 h.; f) NaIO$_4$/SiO$_2$, CH$_2$Cl$_2$, 23° C., 10 h; g) 4 (1.6 equiv), benzene, reflux, 2 days. h) LDA, R$_1$COMe, THF, −78° C., 15 h; i) [IPrAuNCPh]SbF$_6$ (3 mol %), CH$_2$Cl$_2$, 23° C., 5 h; j) TBAF, THF, 23° C., 12 h; k) DMAP, imidazole, TBDM-SCl, 23° C.; l) CrO$_3$, pyridine, CH$_2$Cl$_2$, 23° C., 1 h and CeCl$_3$(H$_2$O)$_7$, NaBH$_4$, MeOH, 23° C., 5 min; m) WCl$_6$ (2 equiv), nBuLi (4 equiv), THF, 0 to 50° C., 2 h; n) R$_5$COCl, DMAP, Et$_3$N, CH$_2$Cl$_2$, 45° C. 4-12 h and TBAF, THF, 23° C., 12 h; o) R$_2$COOH, DMAP, NEt$_3$, 2,4,6-trichlorobenzoyl chloride, toluene, 23° C., 1 h and TBAF, AcOH, THF, 4 h, 23° C.

In accordance with an embodiment, the invention provides a compound of formula (I)

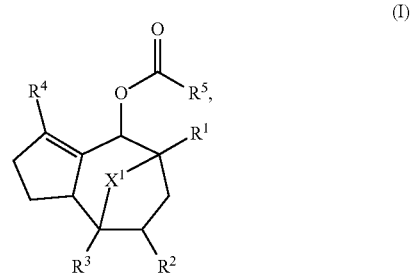

(I)

wherein $R^1$ is selected from $C_1$-$C_6$ alkyl, $C_2$-$C_6$ alkenyl, $C_3$-$C_6$ cycloalkyl, aryl, and heteroaryl, each of which is optionally substituted;

$R^2$ is selected from hydroxy, alkoxy, —$X^2$—($CX^3$)—($CR^6R_7$), —$X^2$—($CX^3$)—$R^8$, —$X^2$—($CX^3$)—($CR^6R^7$)$_m$—$R^8$, and —$X^2$—($CX^3$)—($CR^6R^7$)$_m$—$X^2$—$R^{18}$;

$R^6$ and $R^7$ are independently selected from hydrogen, hydroxy, fluorine, chlorine, and $C_1$-$C_6$ alkyl;

$R^8$ is selected from $C_1$-$C_6$ alkyl, fluoro $C_1$-$C_6$ alkyl, heterocycloalkyl, aryl, heteroaryl, alkoxy, aryloxy, each of the foregoing is optionally substituted, hydroxy, and —$NR^{15}R^{16}$;

$R^{15}$ and $R^{16}$ are independently selected from hydrogen and $C_1$-$C_6$ alkyl; or $R^{16}$ is $COOR^{17}$;

$R^{17}$ is $C_1$-$C_6$ alkyl;

$R^{18}$ is selected from $C_1$-$C_6$ alkyl, fluoro $C_1$-$C_6$ alkyl, aryl, and heteroaryl, each of which is optionally substituted;

each $X^2$ is independently selected from O, S and $NR^{15}$;

$X^3$ is selected from O and S;

$R^3$ and $R^4$ are independently a $C_1$-$C_6$ alkyl;

$R^5$ is selected from —($CR^9R^{10})_n$—$R^{11}$ and —($CR^{12}$=$CR^{13})_n$—$R^{14}$;

$R^9$ and $R^{10}$ are independently selected from hydrogen and $C_1$-$C_6$ alkyl; or alternatively $R^9$ and $R^{10}$, together with the carbon to which they are attached, form a $C_3$-$C_6$ cycloalkyl;

$R^{11}$ and $R^{14}$ are independently selected from $C_1$-$C_6$ alkyl, $C_3$-$C_6$ cycloalkyl, aryl, and heteroaryl, each of which is optionally substituted;

$R^{12}$ and $R^{13}$ are independently selected from hydrogen, halogen, and $C_1$-$C_6$ alkyl;

$X^1$ is selected from O, S and $NR^{15}$; and n and m are independently selected from 0 and an integer of 1-3, or a pharmaceutically acceptable salt thereof.

The compound of formula (I) can have any suitable stereochemistry and can be in the form of a single stereoisomer, a mixture of two or more stereoisomers (e.g., an epimer, a mixture of diastereomers and/or enantiomers, a racemic mixture). In an embodiment, the compound of formula (I) has the stereochemistry of formula (I'):

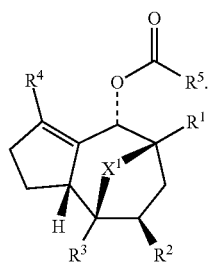

(I')

$R^9$, $R^{10}$, and the carbon to which they are attached can be attached to the carbonyl (C=O) and $R^{11}$ at any suitable positions (e.g., any combination of the 1-position, the 2-position, the 3-position, the 4-position, the 5-position, and the 6-position). For example, $R^9$, $R^{10}$, and the carbon to which they are attached can be attached to the carbonyl (C=O) and $R^{11}$ at the 1- and 2-positions, the 1- and 3-positions, the 1- and 4-positions, the 1- and 5-positions, the 2- and 3-positions, the 2- and 4-positions, the 3- and 4-positions, etc.

In any of the embodiments of the invention, $X^1$ is O.

In any of the embodiments of the invention, $R^1$ is selected from $C_1$-$C_6$ alkyl, $C_3$-$C_6$ cycloalkyl, and aryl. In more specific embodiments of the invention, $R^1$ is selected from isopropyl, tert-butyl, $C_3$-$C_6$ cycloalkyl, and phenyl, any of which is optionally substituted. The $C_3$-$C_6$ cycloalkyl is optionally substituted cyclopropyl, optionally substituted cyclobutyl, optionally substituted cyclopentyl, or optionally substituted cyclohexyl. Preferably, $R^1$ is selected from isopropyl, tert-butyl, cyclopropyl, cyclohexyl, and phenyl.

In any of the embodiments, $R^2$ is selected from hydroxy, alkoxy, radicals of formula —$X^2$—(CO)—$(CR^6R^7)_m$— $X^2$—(CO)—$R^8$, radicals of formula —$X^2$—(CO)—$R^8$, radicals of formula —$X^2$—CO—$X^2$—$R^{18}$, and radicals of formula —$X^2$—C(O)—$(CR^6R^7)_m$—$R^8$. In certain embodiments, $R^2$ is selected from hydroxy, alkoxy, and radicals of formula —$X^2$—C(O)—$(CR^6R^7)_m$—$R^8$. In some aspects, $R^2$ is selected from hydroxy and a radical of formula —$X^2$—C(O)—$(CR^6R^7)_m$—$R^8$, in which $R^6$ is hydrogen, $R^7$ is selected from hydrogen and $C_1$-$C_6$ alkyl; $R^8$ is selected from $C_1$-$C_6$ alkyl, hydroxy, —$NH_2$, and —$NHCOOC_4H_9$, in which $X^2$ is O; and m is 0 or 1. More specifically, in some embodiments of the invention, $R^2$ is selected from —OH, —OCOMe, —OCOCH$_2$OH, —OCOCH(CH$_3$)OH, —OCOCH$_2$NH$_2$, —OCOCH(CH$_3$)NH$_2$, and —OCOCH(CH$_3$)NHCOC$_4$H$_9$.

In any of the embodiments of the invention, $R^5$ is selected from —$(CR^9R^{10})_n$—$R^{11}$ and —$(CR^{12}=CR^{13})_n$—$R^{14}$; in which $R^9$ and $R^{10}$ are independently selected from hydrogen and $C_1$-$C_6$ alkyl, or alternatively, $R^9$ and $R^{10}$, together with the carbon to which they are attached, form a $C_3$-$C_6$ cycloalkyl; $R^{11}$ and $R^{14}$ are independently selected from $C_1$-$C_6$ alkyl and aryl, each of which is optionally substituted; and $R^{12}$ and $R^{13}$ are independently selected from hydrogen and optionally substituted $C_1$-$C_6$ alkyl.

In any of the embodiments of the invention, $R^5$ is —$(CR^9R^{10})_n$—$R^{11}$, $R^9$ and $R^{10}$ are each hydrogen, $R^{11}$ is phenyl, and n is 1-3. Preferably, n is 3 so as to form a radical of formula —$(CH_2)_3$Ph.

Alternatively, in any of the embodiments of the invention, $R^5$ is —$(CR^9R^{10})_n$—$R^{11}$, n is 0, and $R^{11}$ is $C_1$-$C_6$ alkyl, which is optionally substituted. More preferably, $R^5$ is methyl.

Alternatively, in any of the embodiments of the invention, $R^5$ is —$(CR^9R^{10})_n$—$R^{11}$, $R^9$ and $R^{10}$, together with the carbon to which they are attached, form a $C_3$-$C_6$ cycloalkyl, $R^{11}$ is phenyl, and n is 1 or 2. The $C_3$-$C_6$ cycloalkyl is optionally substituted cyclopropyl, optionally substituted cyclobutyl, optionally substituted cyclopentyl, or optionally substituted cyclohexyl. In particular, $R^9$ and $R^{10}$, together with the carbon atom to which they are attached, form a cyclopropyl (e.g., attached at the 1- and 2-positions). More particularly, $R^5$ is 2-phenylcyclopropyl.

Alternatively, in any of the embodiments of the invention, $R^5$ is —$(CR^{12}=CR^{13})_n$—$R^{14}$, $R^{12}$ and $R^{13}$ are each hydrogen, $R^{14}$ is phenyl, and n is 1-3. Preferably, n is 1 so as to form a radical of formula —(CH=CH)Ph.

In any of the embodiments of the invention, either one or both of $R^3$ and $R^4$ is methyl.

Specific examples of the compound of formula (I) are:

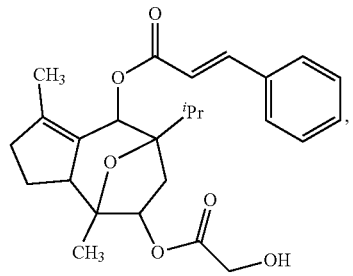

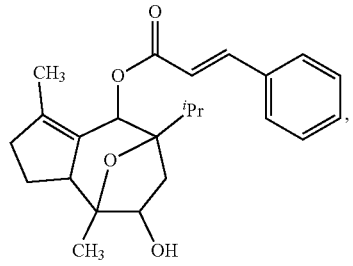

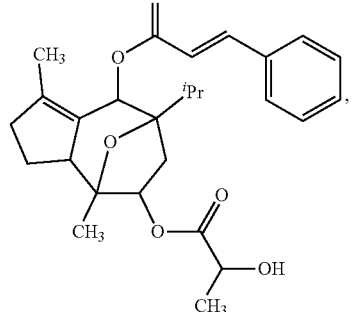

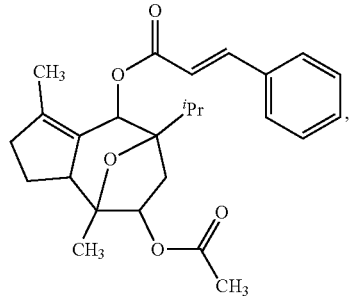

-continued
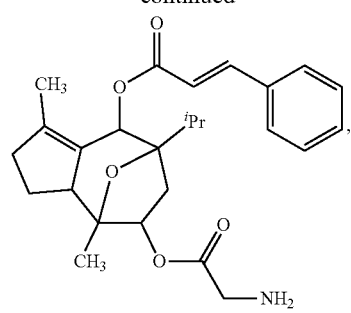
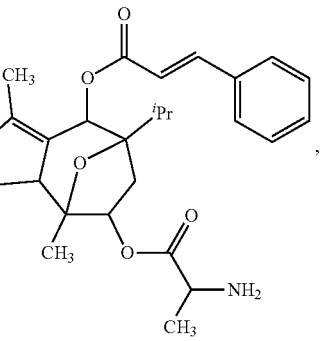
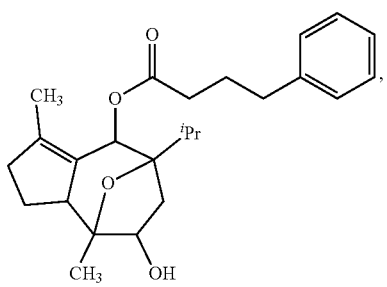
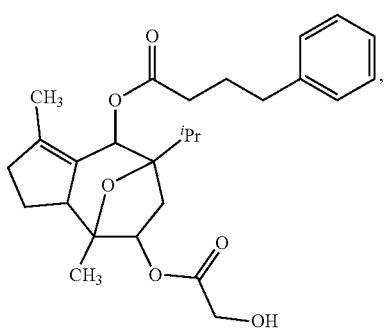
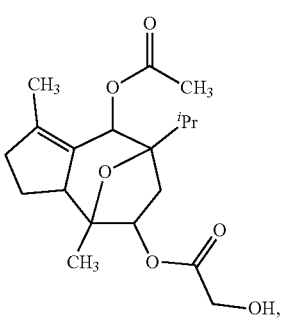
-continued
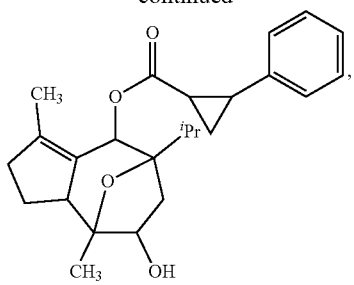
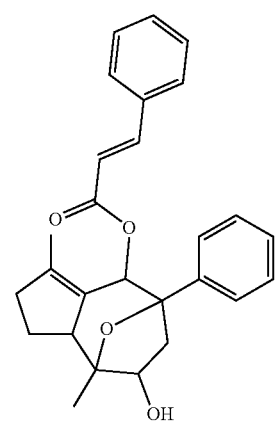
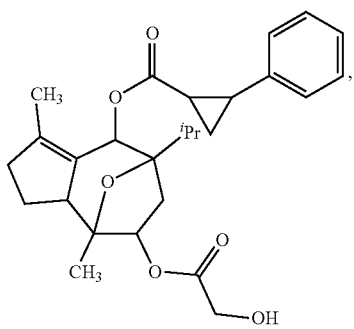
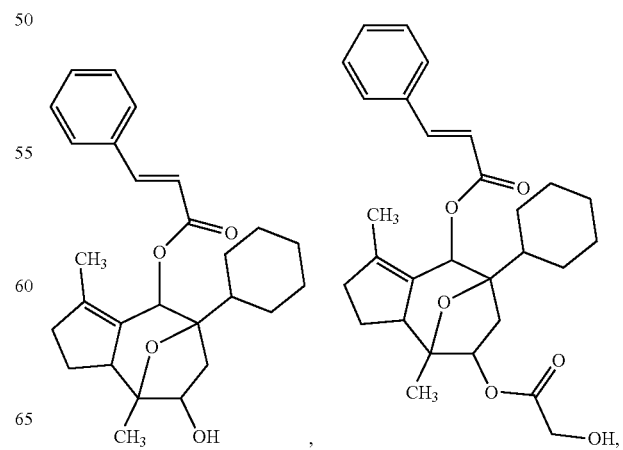

-continued
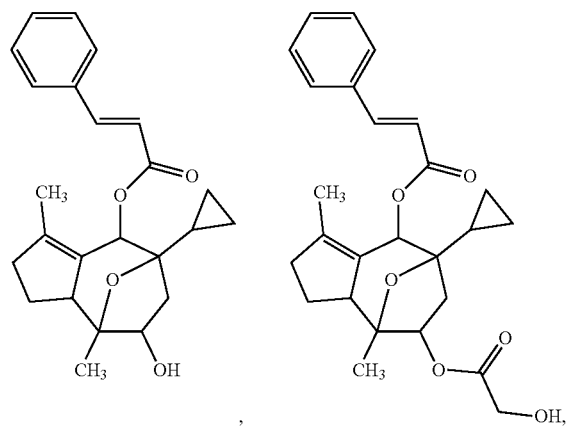
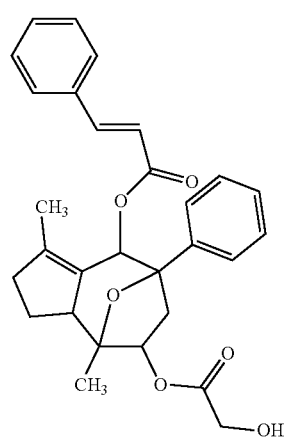
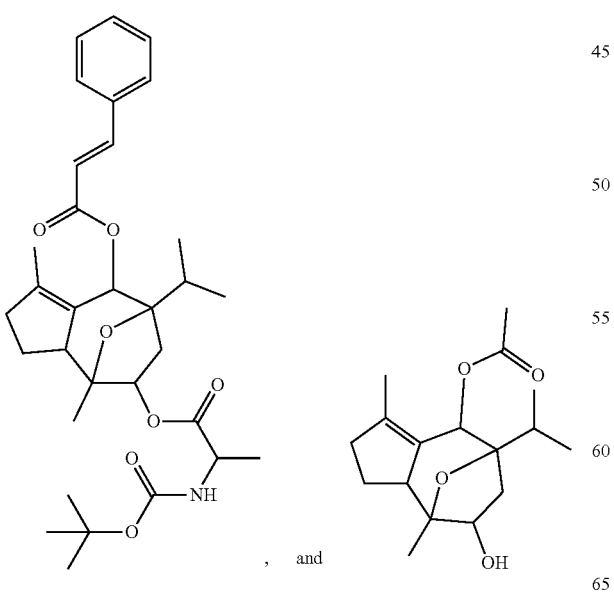
, and
or a pharmaceutically acceptable salt thereof.
Specific examples of the compound of formula (I') are:
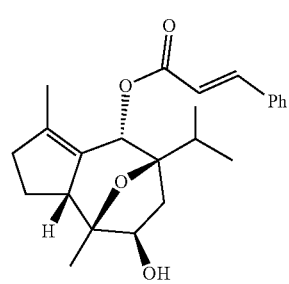
(Ia)
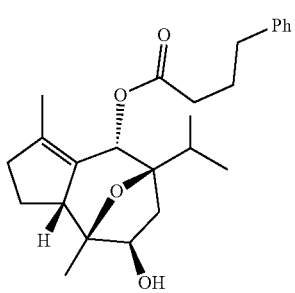
(Ib)
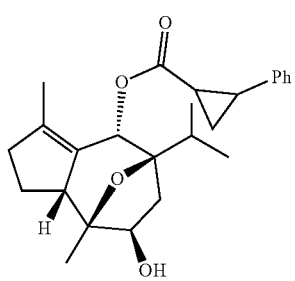
(Ic)
(Id)
(Ie)

(If)
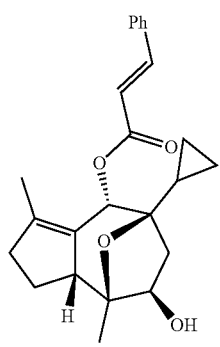
(Ig)
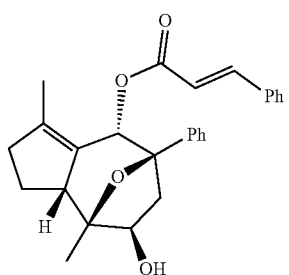
(Ih)
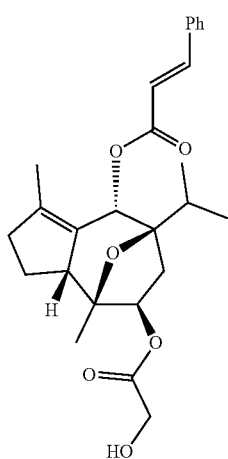
(Ii)
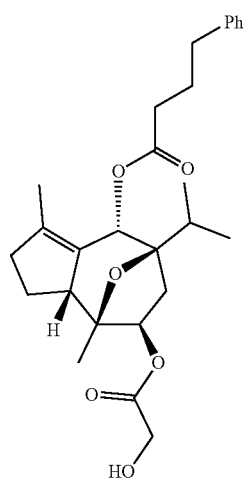
(Ij)
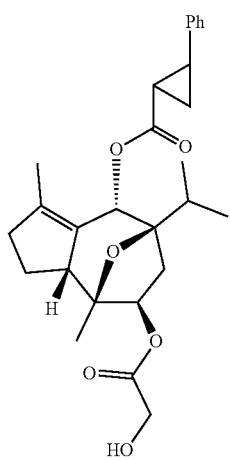
(Ik)
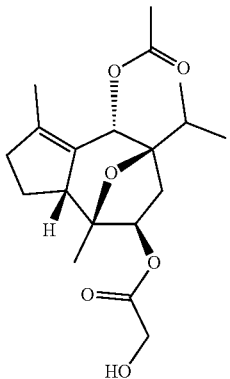
(Il)
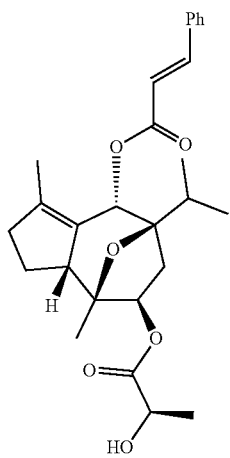

13
-continued
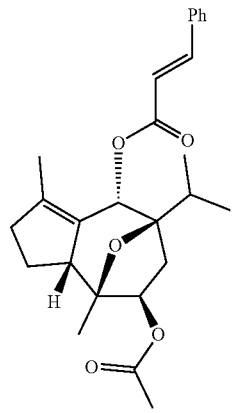
(Im)
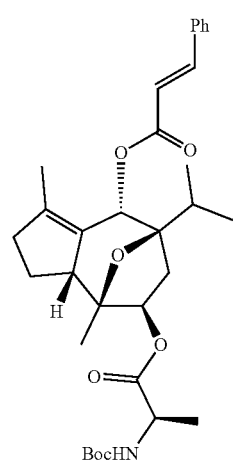
(In)
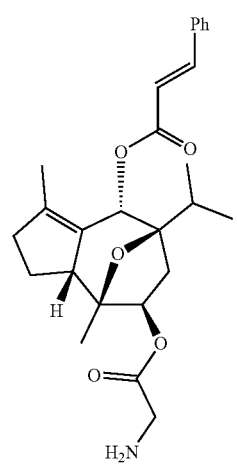
(Io)
14
-continued
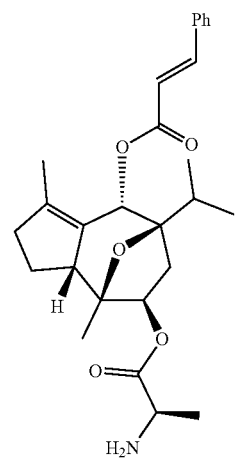
(Ip)
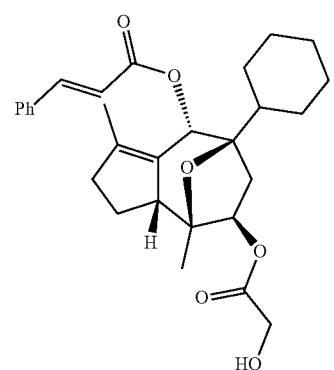
(Iq)
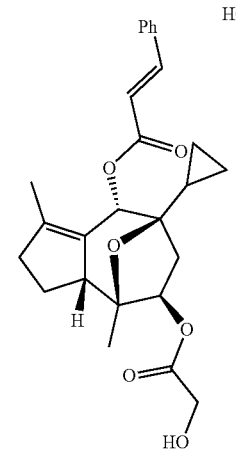
(Ir)
and
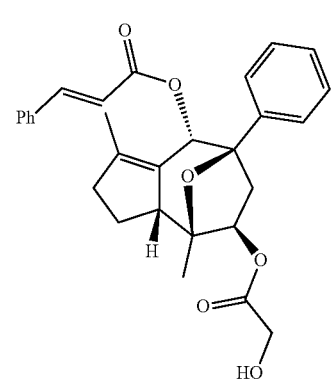
(Is)
or a pharmaceutically acceptable salt thereof.

Exemplary compounds of formula (I) are the compound of formulae (Ih), (Ij), (II), (Im), (Iq), (Ir), and (Is).

In any of the embodiments above, the term "alkyl" implies a straight-chain or branched alkyl substituent containing from, for example, from about 1 to about 6 carbon atoms, e.g., from about 1 to about 4 carbon atoms or about 1 to about 3 carbons. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., fluoro $C_1$-$C_6$ alkyl. The alkyl can be substituted or unsubstituted, as described herein.

In any of the embodiments above, the term "alkenyl," as used herein, means a linear alkenyl substituent containing from, for example, 2 to about 6 carbon atoms (branched alkenyls are about 3 to about 6 carbons atoms), e.g., from about 3 to about 6 carbon atoms (branched alkenyls are about 3 to about 6 carbons atoms). In accordance with an embodiment, the alkenyl group is a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like. The alkenyl can be substituted or unsubstituted, as described herein.

In any of the embodiments above, the term "cycloalkyl," as used herein, means a cyclic alkyl moiety containing from, for example, 3 to 6 carbon atoms or from 5 to 6 carbon atoms. Examples of such moieties include cyclopropyl, cyclobutyl, cyclopentyl, cyclohexyl, and the like. The cycloalkyl can be substituted or unsubstituted, as described herein.

The term "heterocycloalkyl" means a stable, saturated, or partially unsaturated monocyclic, bicyclic, and spiro ring system containing 3 to 7 ring members of carbon atoms and other atoms selected from nitrogen, sulfur, and/or oxygen. In an aspect, a heterocycloalkyl is a 5, 6, or 7-membered monocyclic ring and contains one, two, or three heteroatoms selected from nitrogen, oxygen, and sulfur. The heterocycloalkyl may be attached to the parent structure through a carbon atom or through any heteroatom of the heterocycloalkyl that results in a stable structure. Examples of such heterocycloalkyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl. The heterocycloalkyl can be substituted or unsubstituted, as described herein.

In any of the embodiments above, the term "hydroxy" refers to the group —OH.

In any of the embodiments above, the terms "alkoxy" and "aryloxy" embrace linear or branched alkyl and aryl groups that are attached to a divalent oxygen. The alkyl and aryl groups are the same as described herein.

In any of the embodiments above, the term "halo" refers to a halogen selected from fluorine, chlorine, bromine, and iodine.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise 4n+2 π electrons, according to Hückel's Rule, wherein n=1, 2, or 3. The aryl can be substituted or unsubstituted, as described herein.

In any of the embodiments above, the term "heteroaryl" refers to an aryl as defined above in which at least one, preferably 1 or 2, of the carbon atoms of the aromatic carbocyclic ring is replaced by N, O, or S atoms. Examples of heteroaryl include pyridyl, furanyl, pyrrolyl, quinolinyl, thiophenyl, indolyl, imidazolyl, and the like.

In other aspects, any substituent that is not hydrogen (e.g., $C_1$-$C_6$ alkyl, $C_2$-$C_6$ alkenyl, $C_3$-$C_6$ cycloalkyl, or aryl) can be an optionally substituted moiety. The substituted moiety typically comprises at least one substituent (e.g., 1, 2, 3, 4, 5, 6, etc.) in any suitable position (e.g., 1-, 2-, 3-, 4-, 5-, or 6-position, etc.). When a group, such alkyl, cycloalkyl, aryl, heteroaryl, etc., is substituted with a substituent, e.g., halo, amino, alkyl, OH, alkoxy, cyano, nitro, and others, a hydrogen on the group is replaced with the substituent and this can take place in any of the available hydrogens, e.g., 2, 3, 4, 5, and/or 6-position wherein the 1-position is the point of attachment of the group in the compound of the present invention. Suitable substituents include, e.g., halo, alkyl, alkenyl, alkynyl, hydroxy, nitro, cyano, amino, alkylamino, alkoxy, aryloxy, aralkoxy, carboxyl, carboxyalkyl, carboxyalkyloxy, amido, alkylamido, haloalkylamido, aryl, heteroaryl, and heterocycloalkyl. In some instances, the substituent is one or more (e.g., 1 or 2) moiety selected from alkyl, halo, and/or haloalkyl.

In any of the embodiments above, whenever a range of the number of atoms in a structure is indicated (e.g., a $C_{1-6}$, or $C_{1-4}$ alkyl, $C_3$-$C_6$ cycloalkyl, etc.), it is specifically contemplated that any sub-range or individual number of carbon atoms falling within the indicated range also can be used. Thus, for instance, the recitation of a range of 1-6 carbon atoms (e.g., $C_1$-$C_6$), 1-4 carbon atoms (e.g., $C_1$-$C_4$), 1-3 carbon atoms (e.g., $C_1$-$C_3$), or 2-6 carbon atoms (e.g., $C_2$-$C_6$) as used with respect to any chemical group (e.g., alkyl, cycloalkyl, etc.) referenced herein encompasses and specifically describes 1, 2, 3, 4, 5, and/or 6 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 2-3 carbon atoms, 2-4 carbon atoms, 2-5 carbon atoms, 2-6 carbon atoms, 3-4 carbon atoms, 3-5 carbon atoms, 3-6 carbon atoms, 4-5 carbon atoms, 4-6 carbon atoms, etc., as appropriate).

The subscripts "m" and "n" represent the number of substituents (e.g., "$(CR^6R^7)$," "$(CR^9R^{10})$," or "$(CR^{12}=CR^{13})$"), in which each instance of a particular substituent (e.g., "$(CR^6R^7)$," "$(CR^9R^{10})$," or "$(CR^{12}=CR^{13})$") can be the same or different. The subscripts m and n can be the same or different and each is either 0 or an integer from 1-3 (i.e., 1, 2, or 3). When m or n is 0, then the corresponding substituent (e.g., "$(CR^6R^7)$," "$(CR^9R^{10})$," or "$(CR^{12}=CR^{13})$") is not present in the compound of formula (I).

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, nonaqueous media such as ether, ethyl acetate, ethanol, isopropanol, or acetonitrile are typical. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

Figure 2:
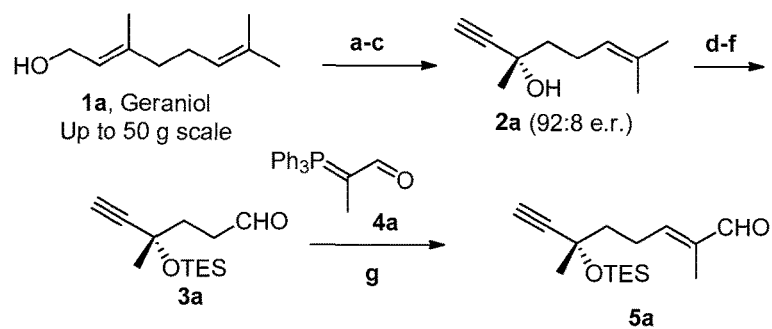
Figure 3A:
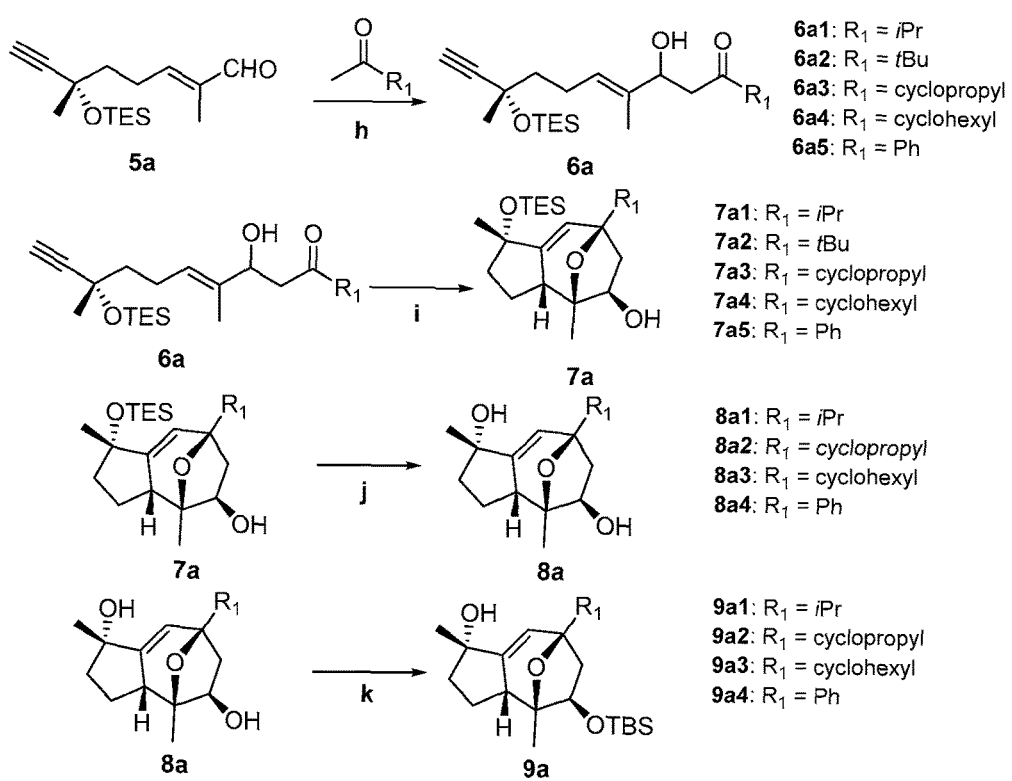
Figure 3B:
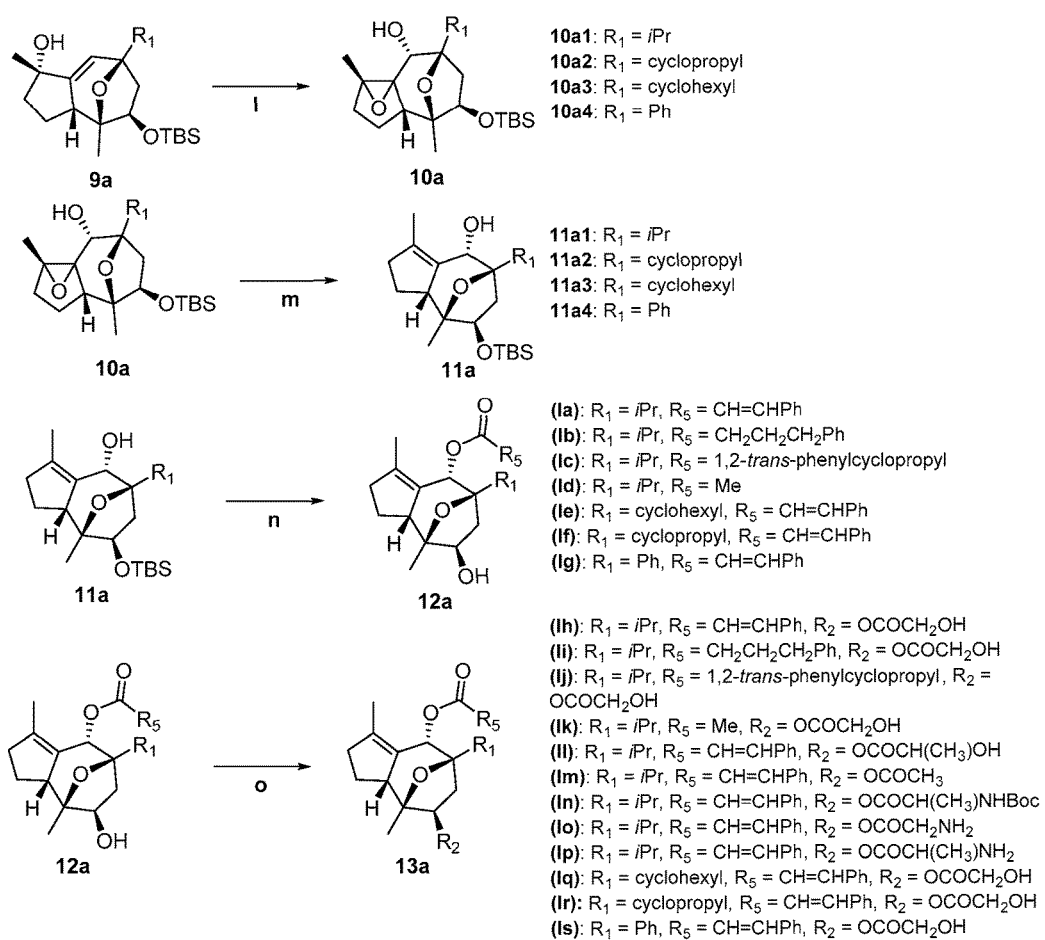
FIG. 3B shows steps l-o.
Figure 4A:
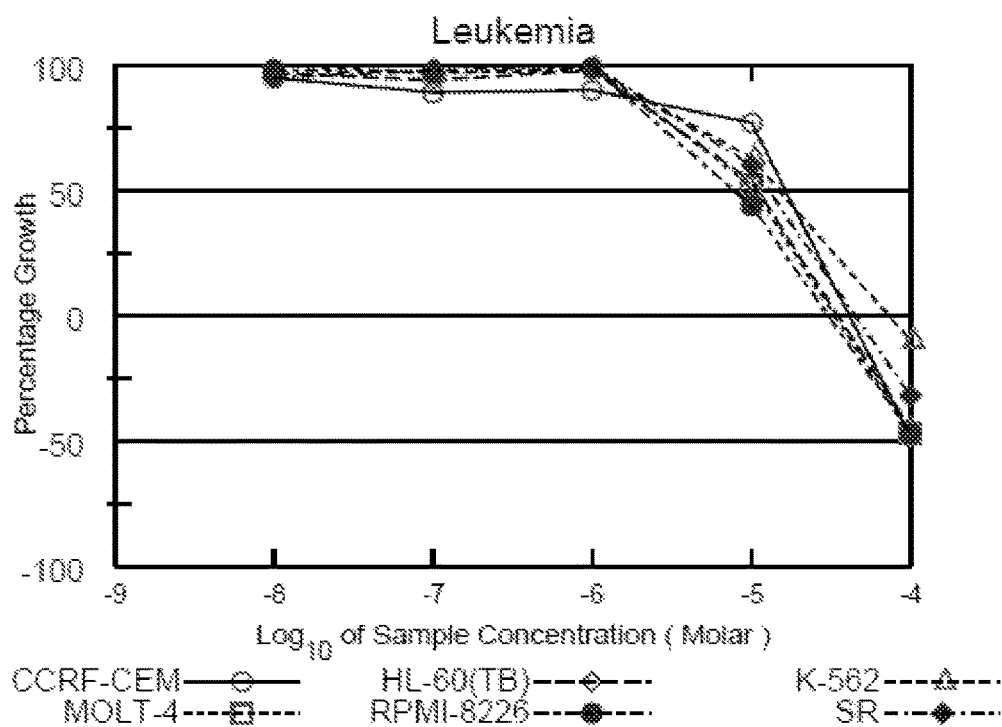
FIGS. 4A-4I depict the dose response curves for a compound formula (I) (i.e., (II)) against various cancer cell lines in the standard NCI 60-cell test.
Figure 4B:
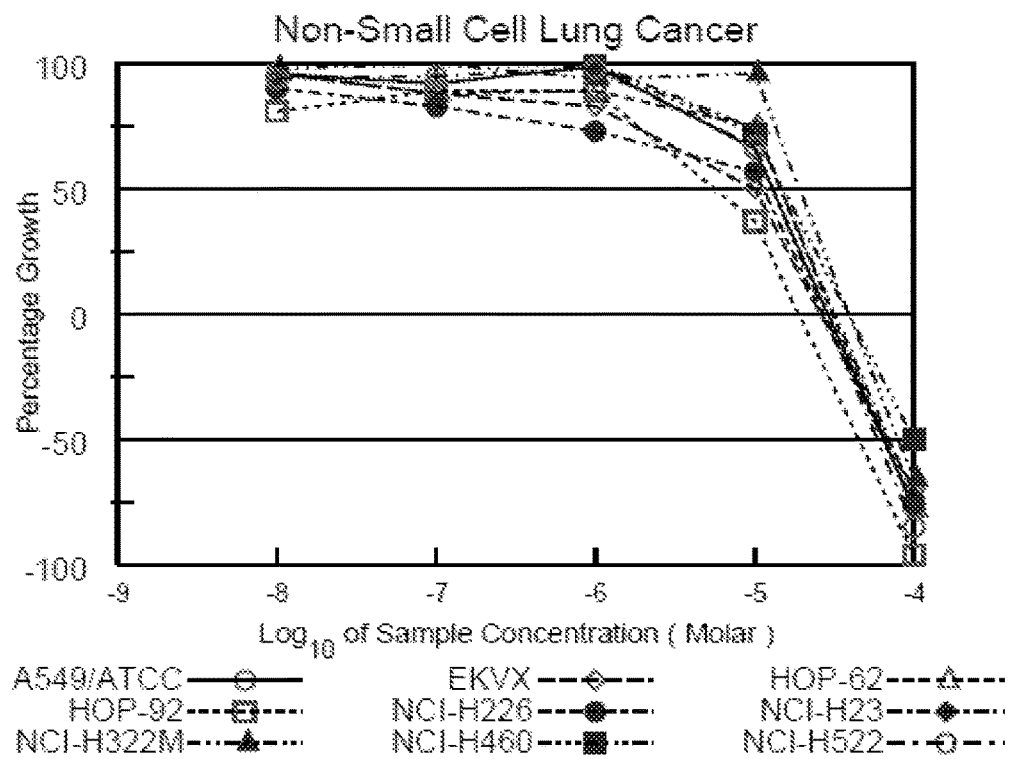
Figure 4C:
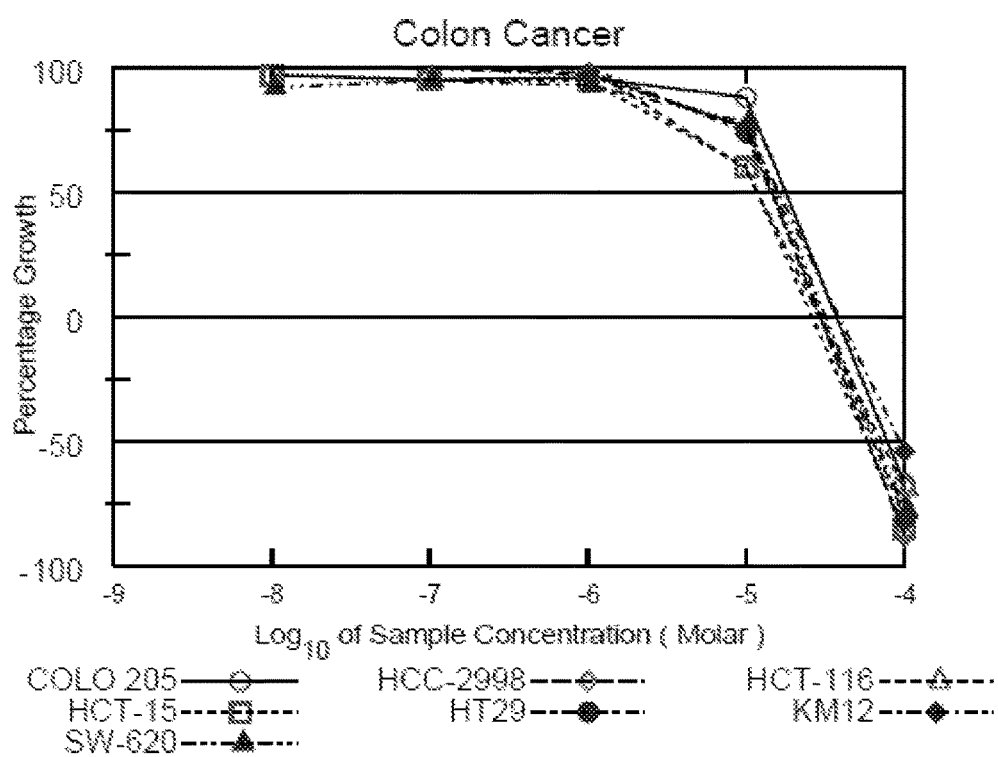
Figure 4D:
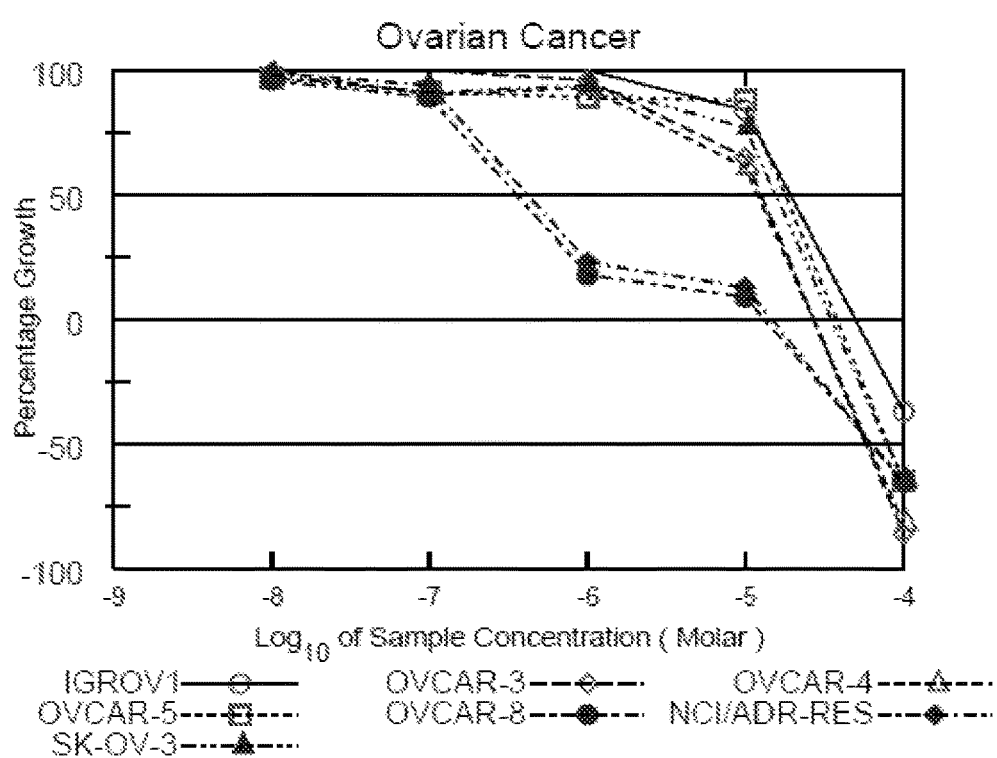
Figure 4E:
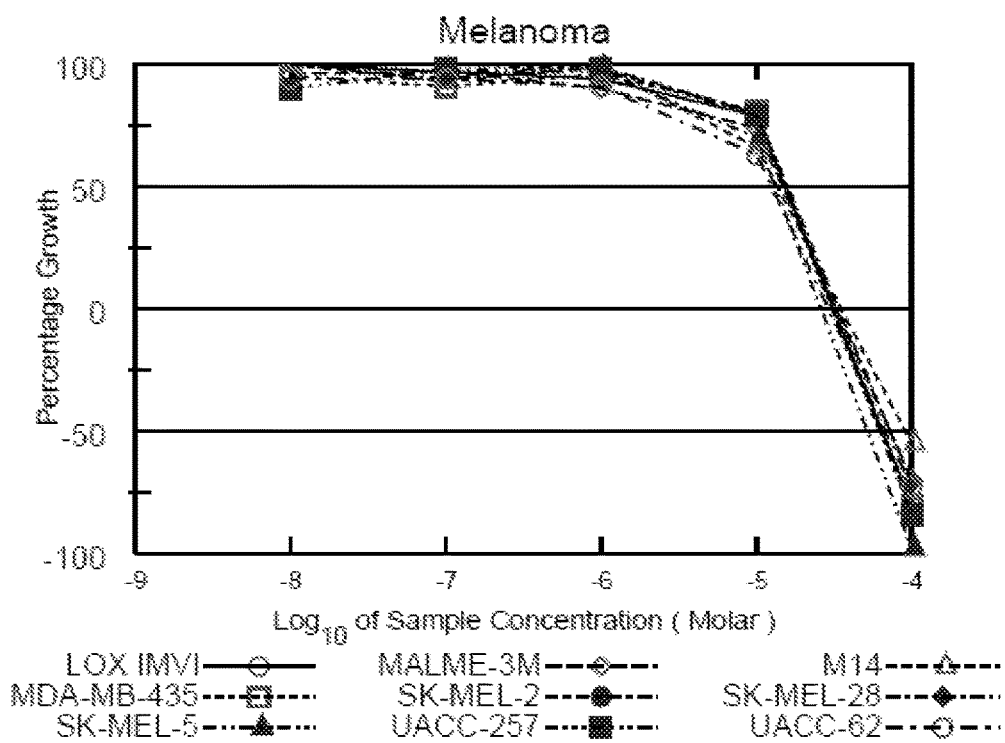
Figure 4F:
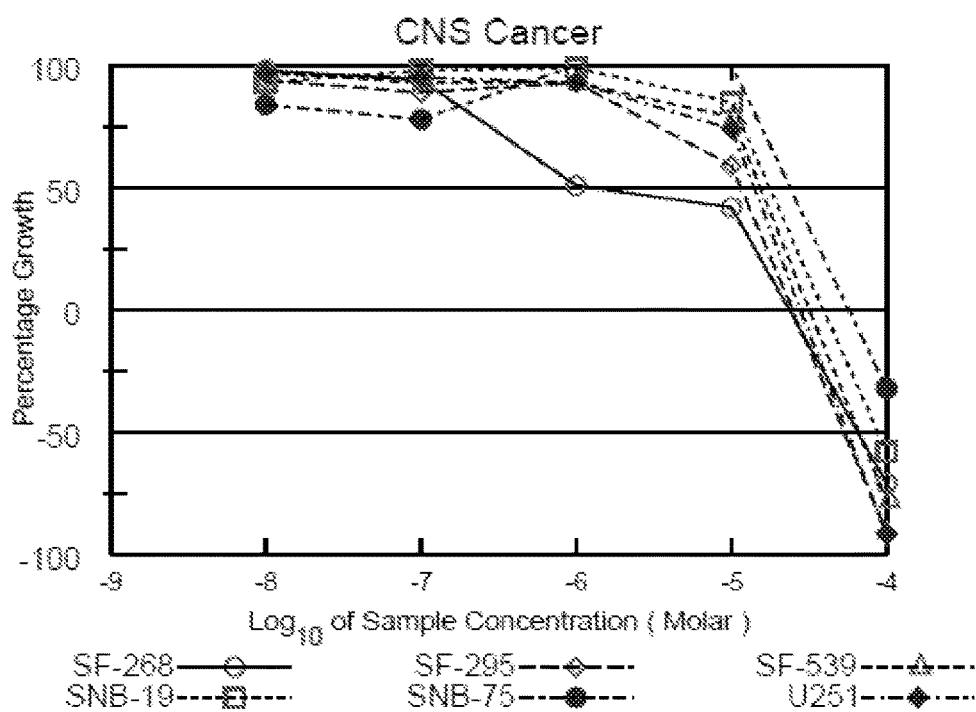
Figure 4G:
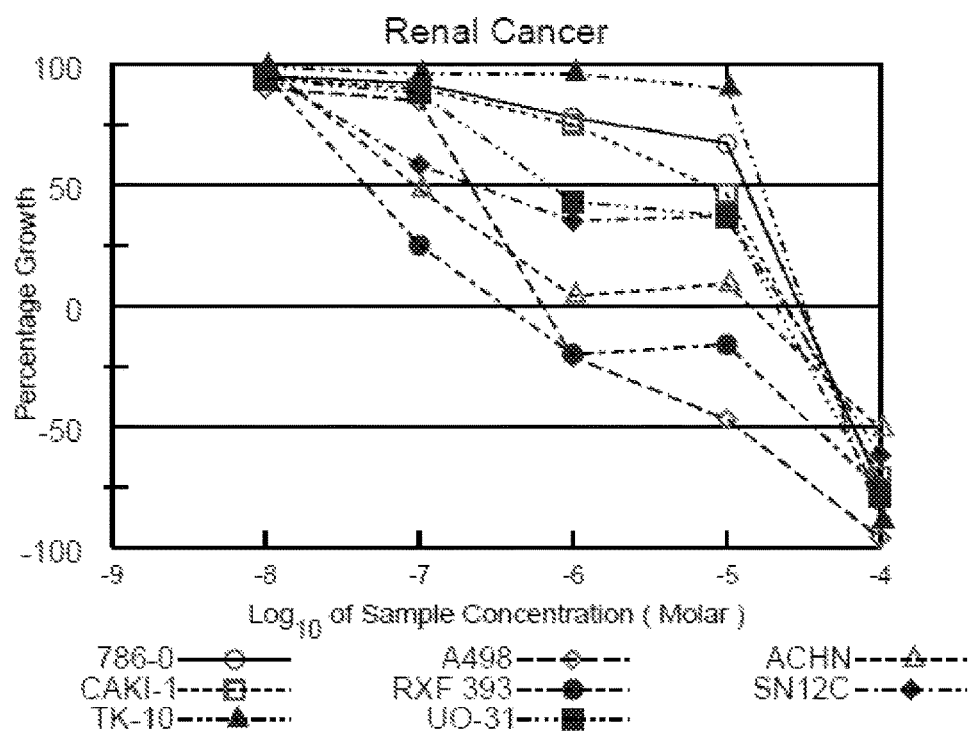
Figure 4H:
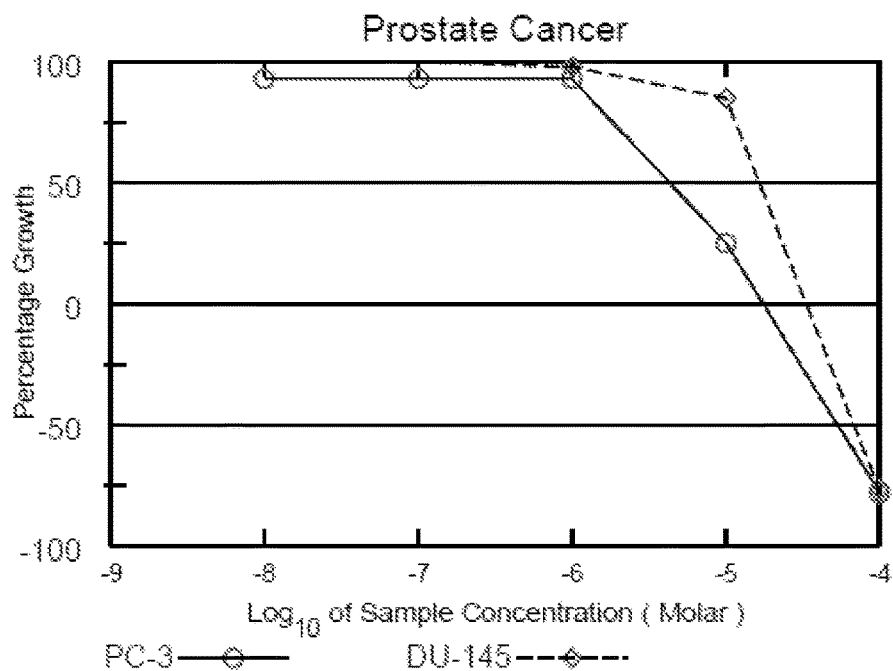
Figure 4I:
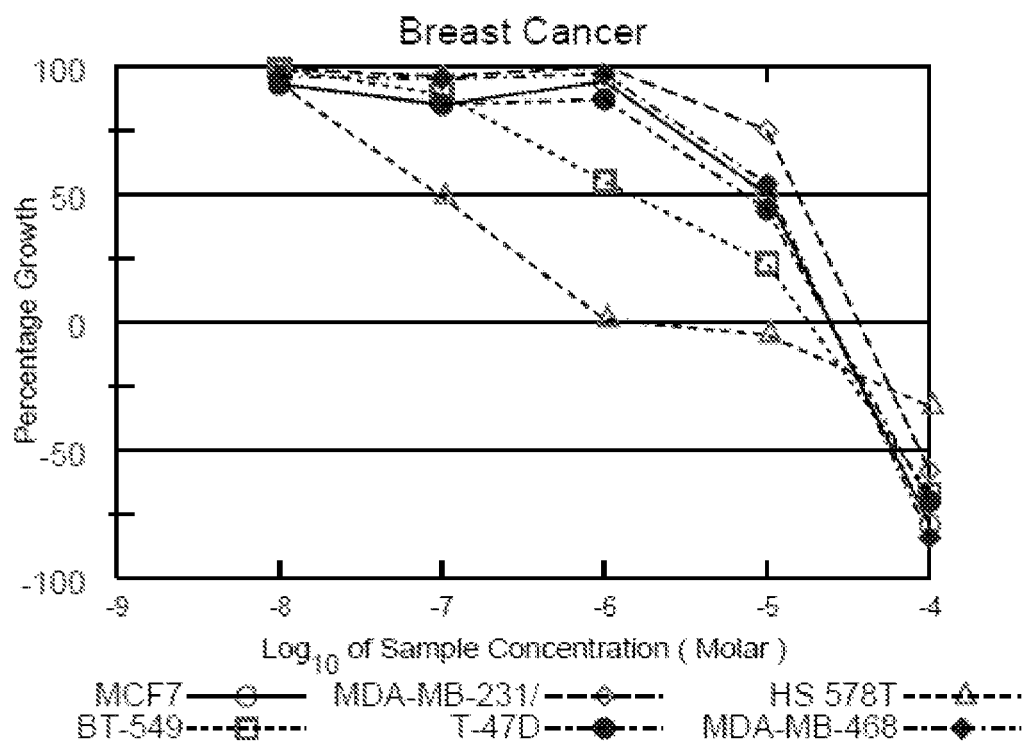
Figure 5A:
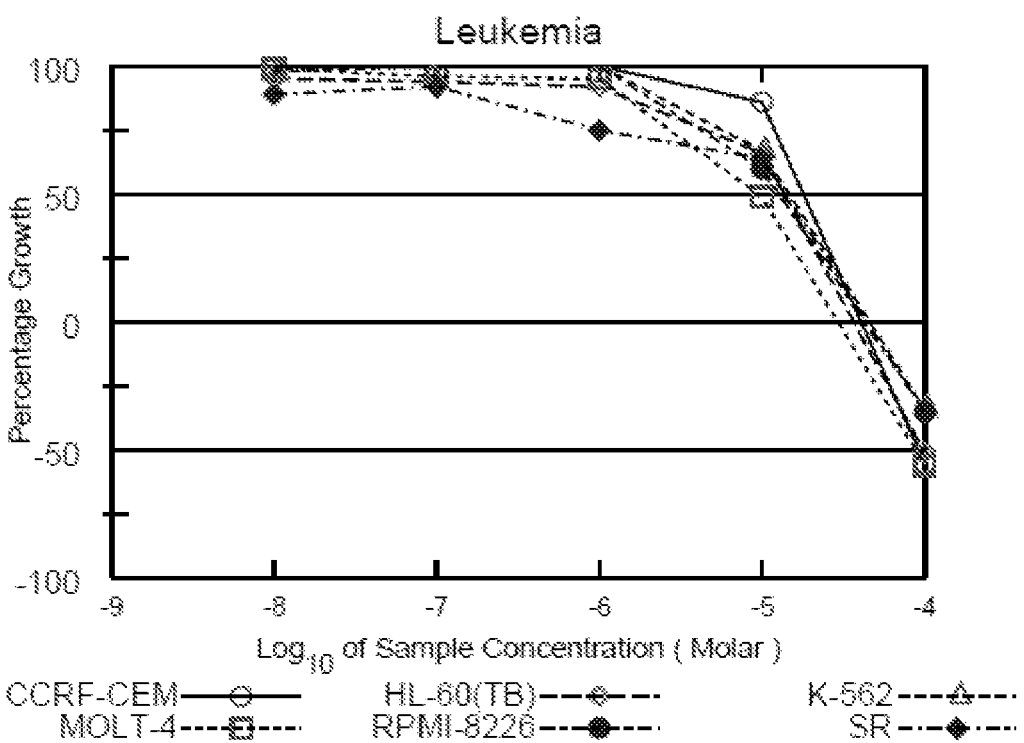
FIGS. 5A-5I depict the dose response curves for a compound formula (I) (i.e., (Ij)) against various cancer cell lines in the NCI 60-cell test.
Figure 5B:
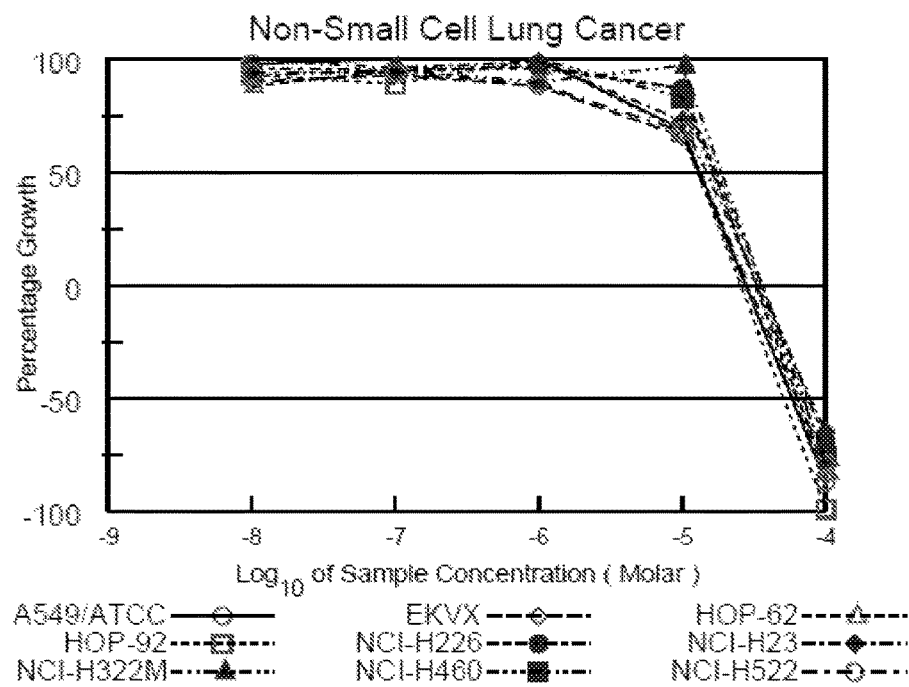
Figure 5C:
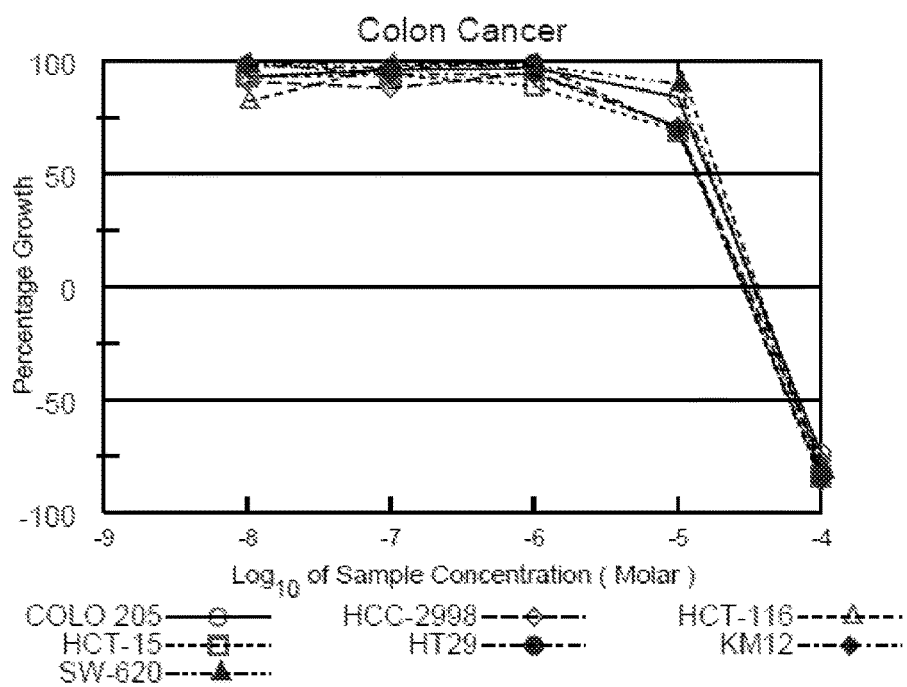
Figure 5D:
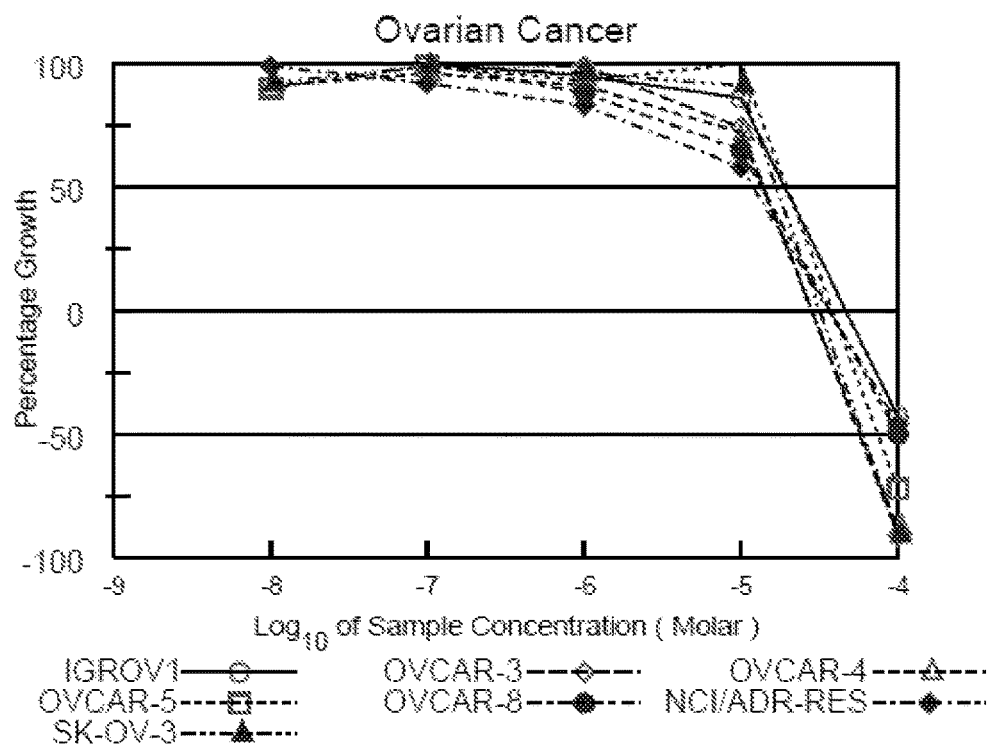
Figure 5E:
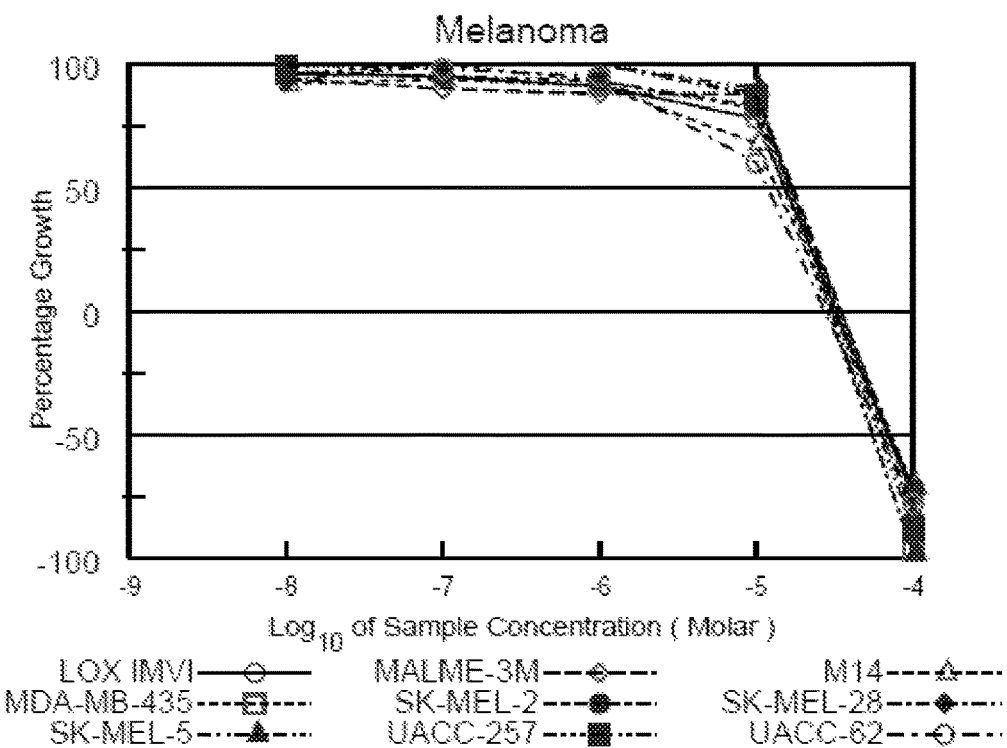
Figure 5F:
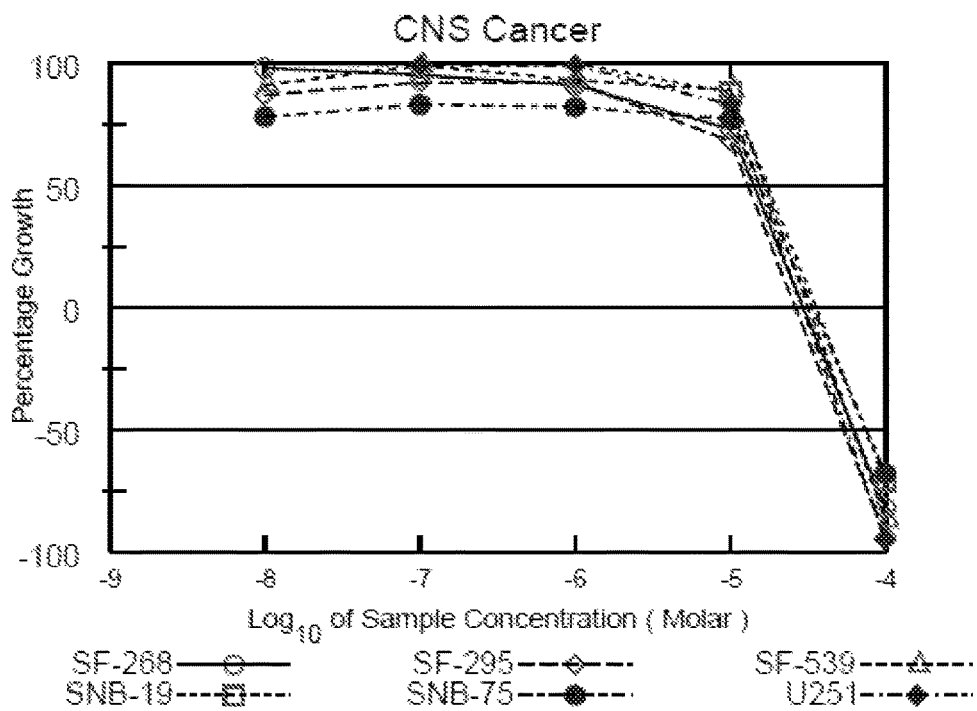
Figure 5G:
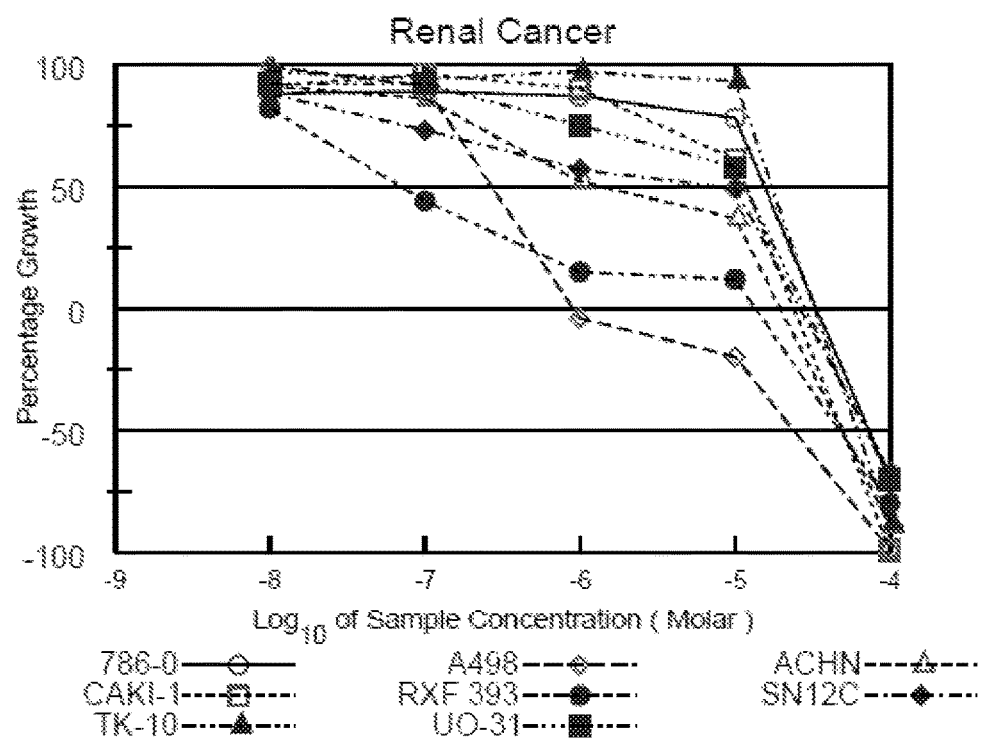
Figure 5H:
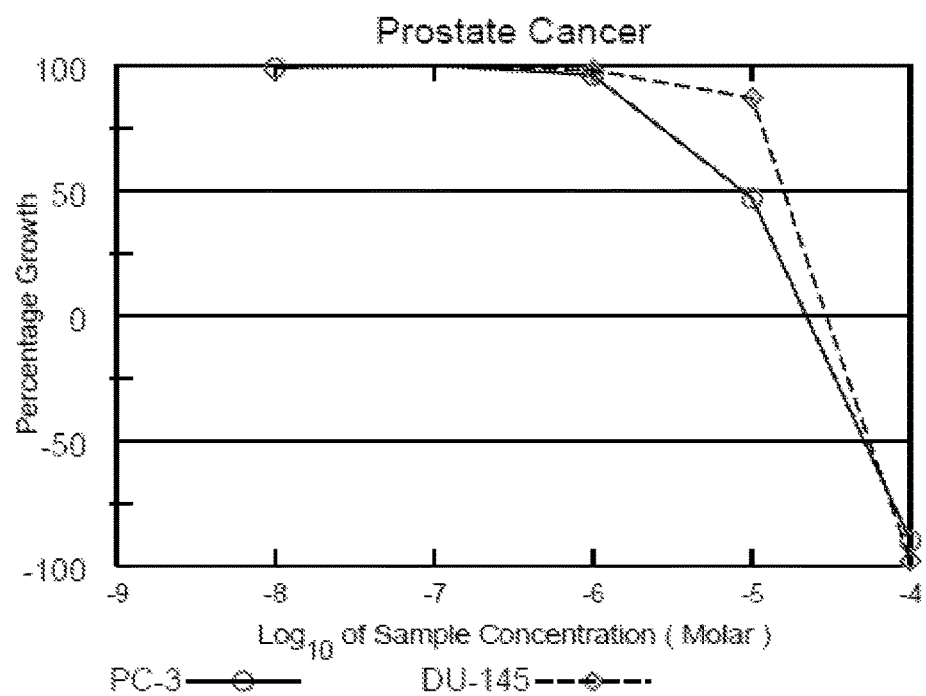
Figure 5I:
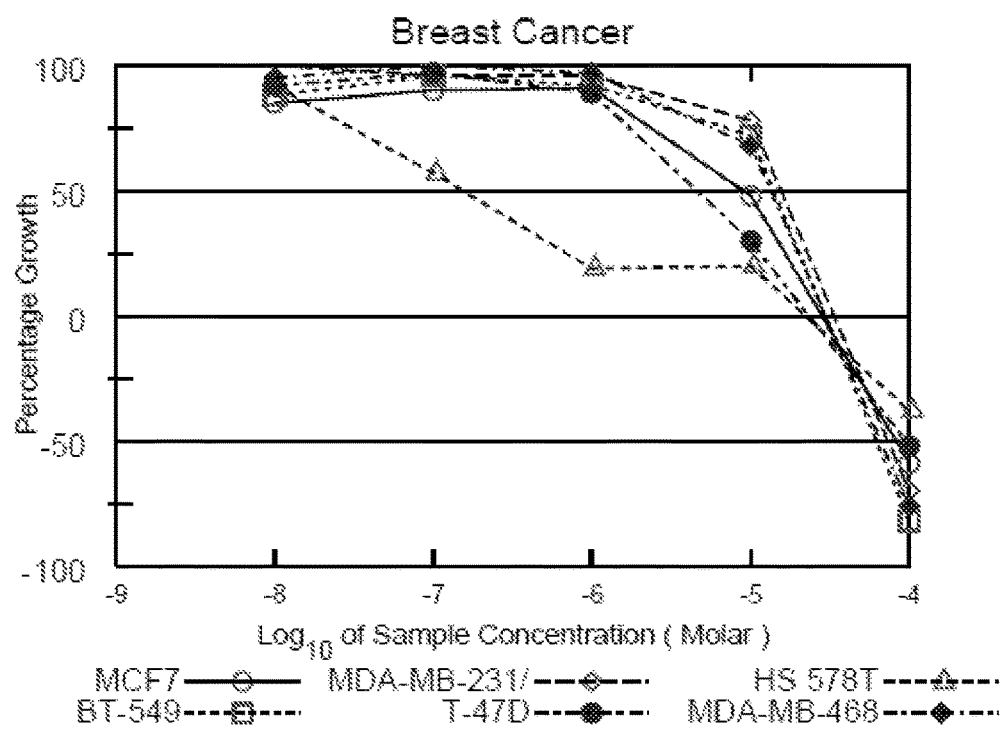
Figure 6A:
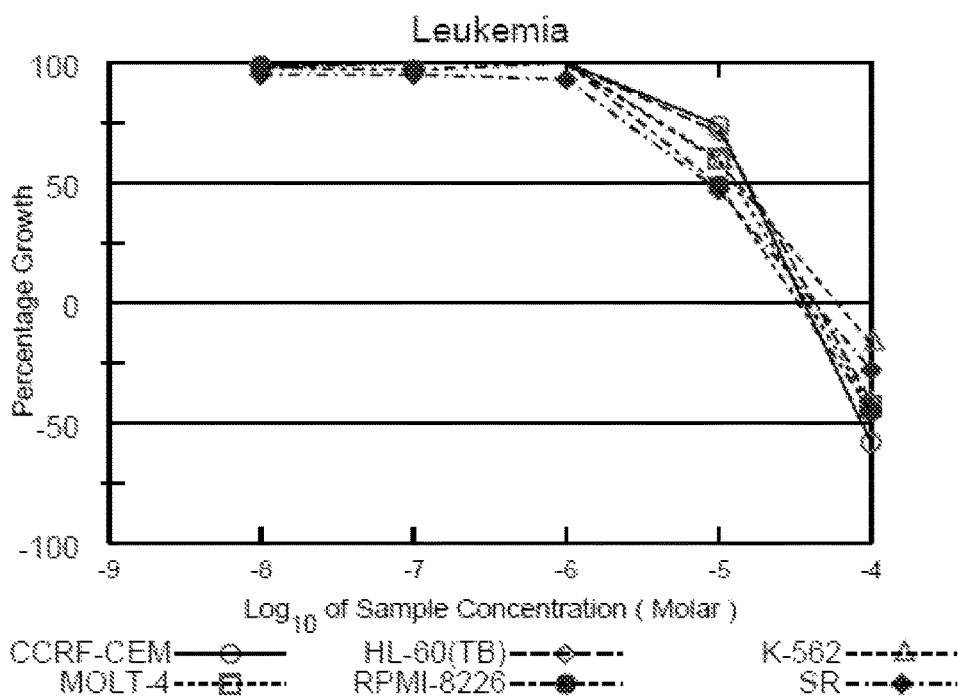
FIGS. 6A-6I depict the dose response curves for a compound formula (I) (i.e., (Iq)) against various cancer cell lines in the NCI 60-cell test.
Figure 6B:
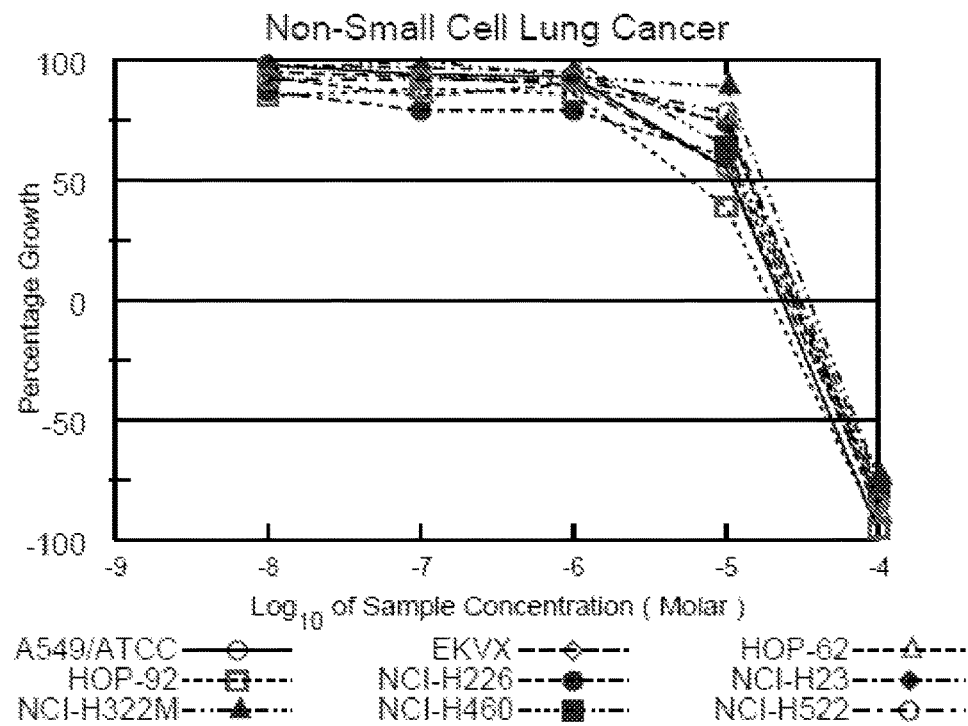
Figure 6C:
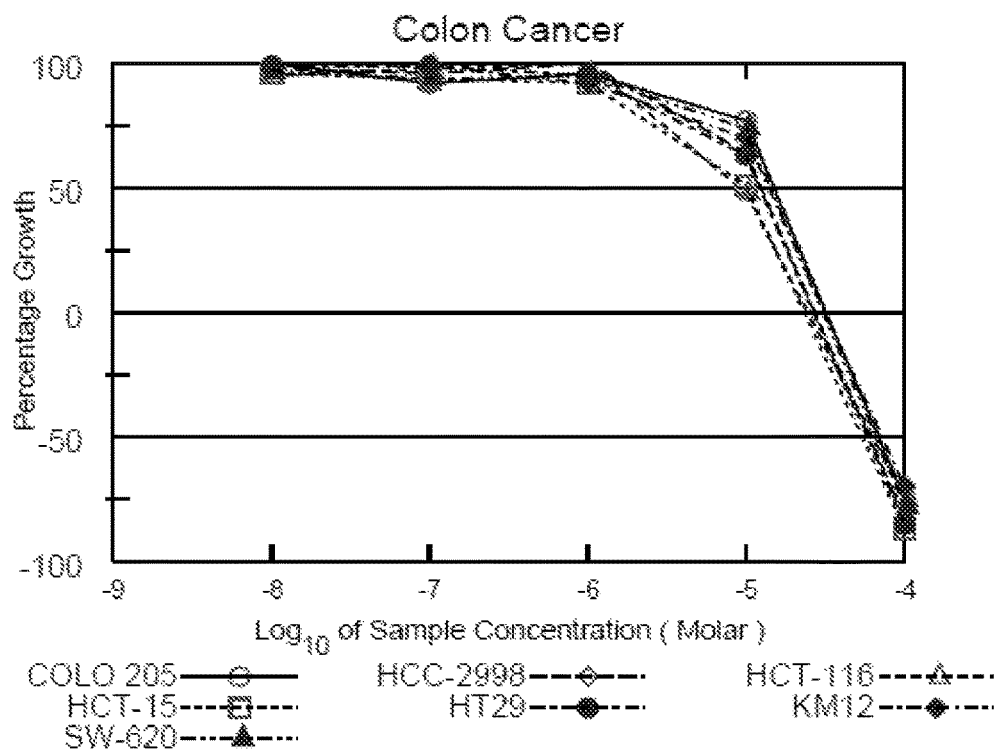
Figure 6D:
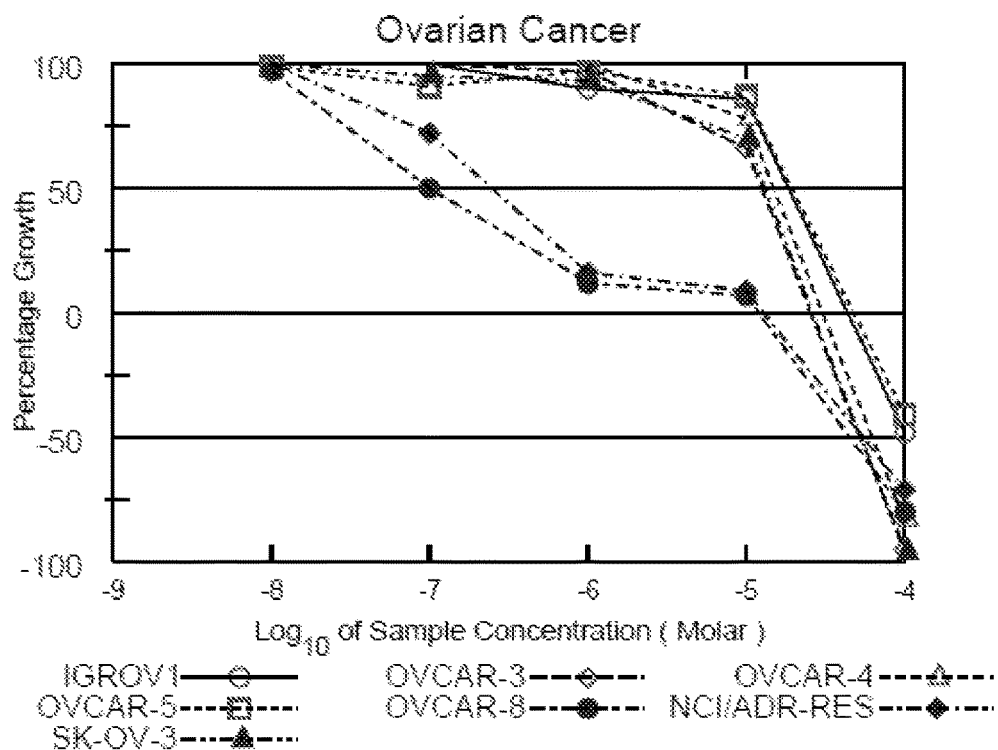
Figure 6E:
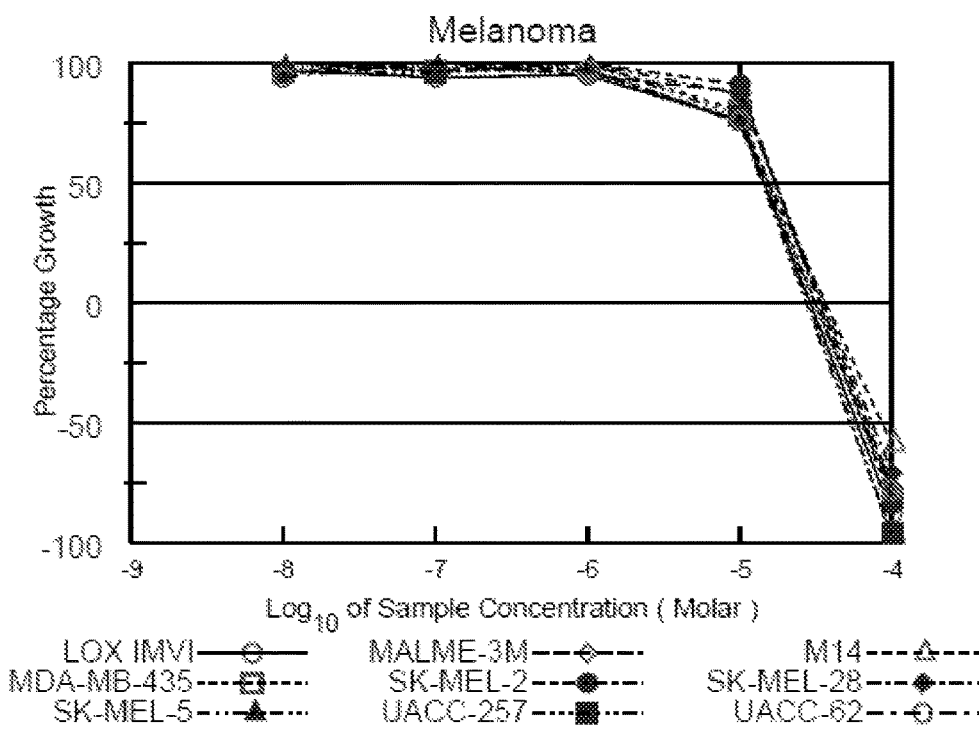
Figure 6F:
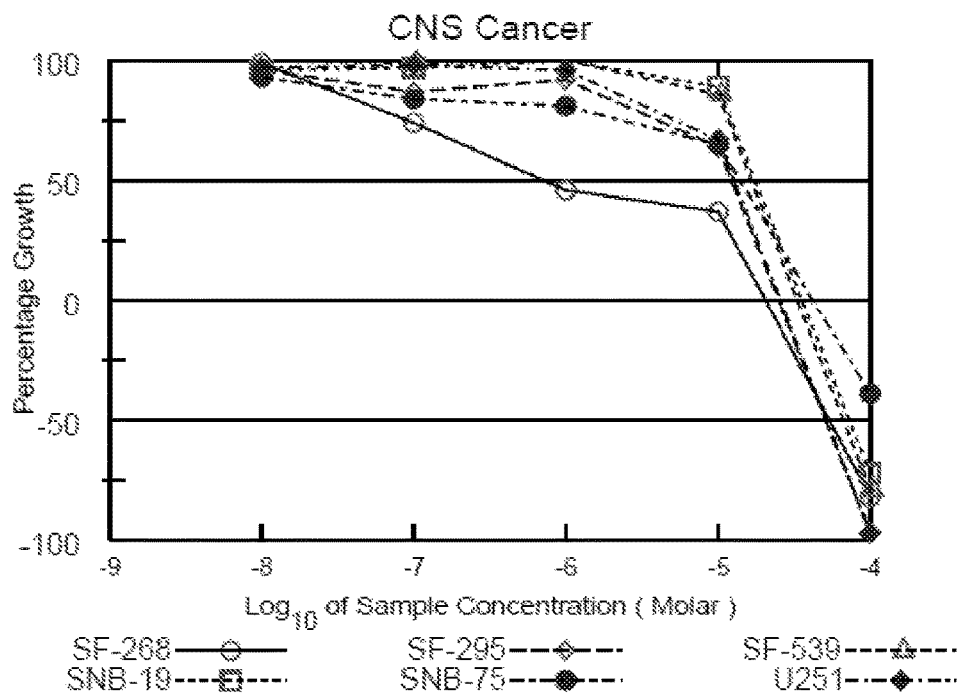
Figure 6G:
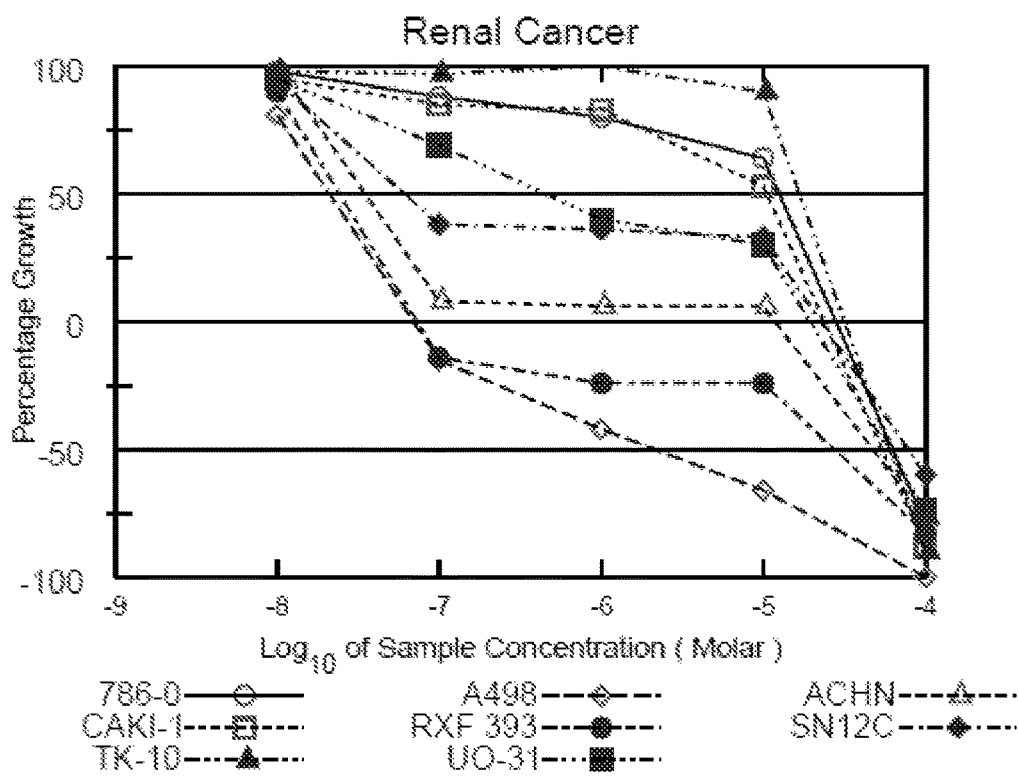
Figure 6H:
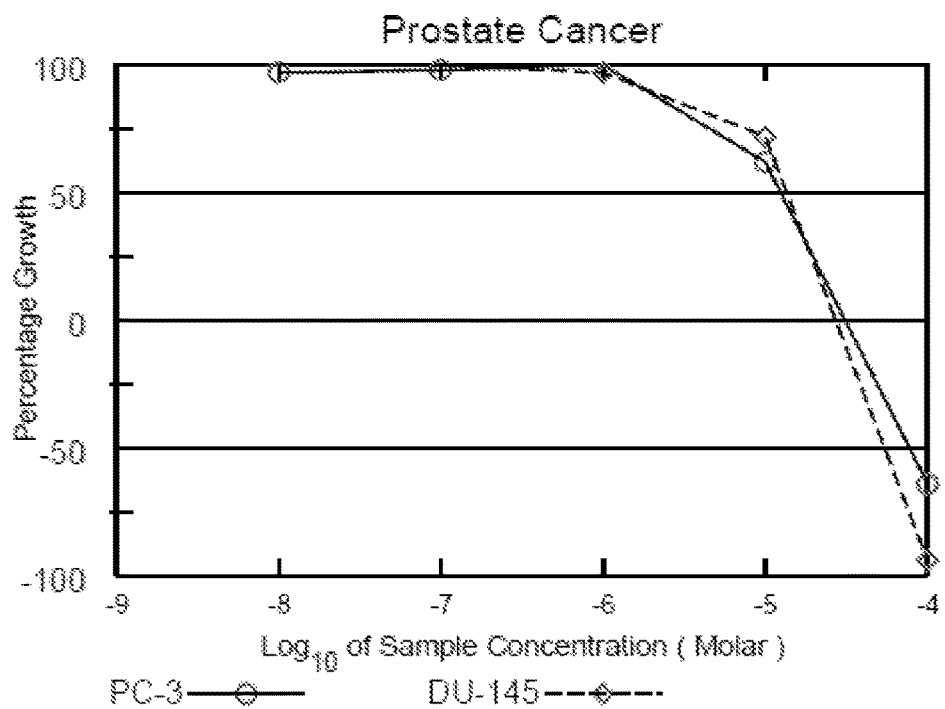
Figure 6I:
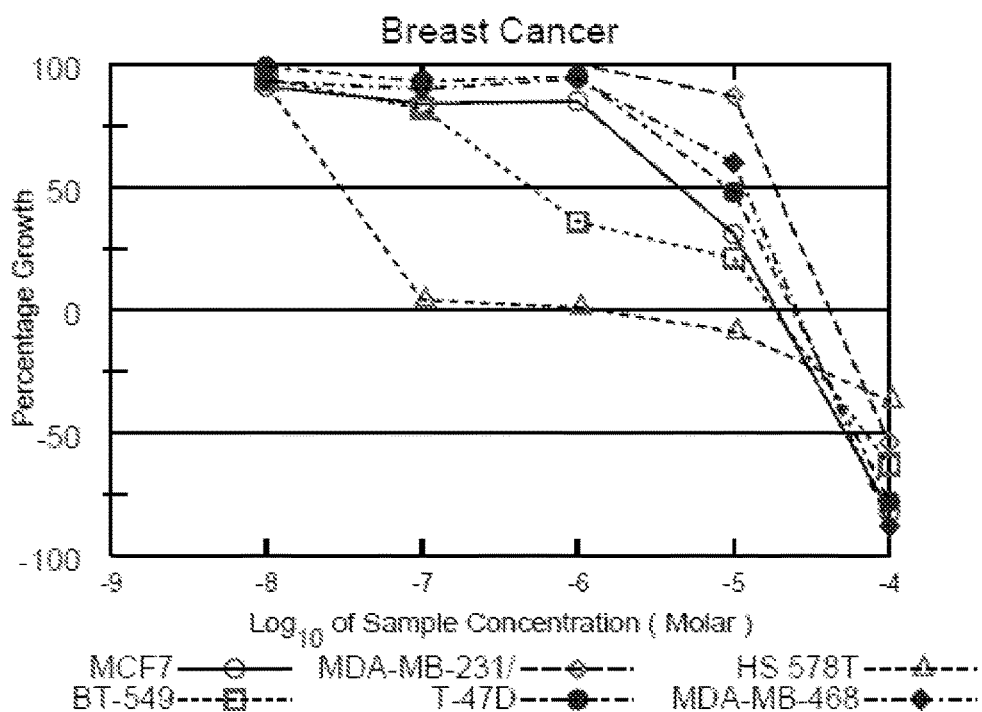
Figure 7A:
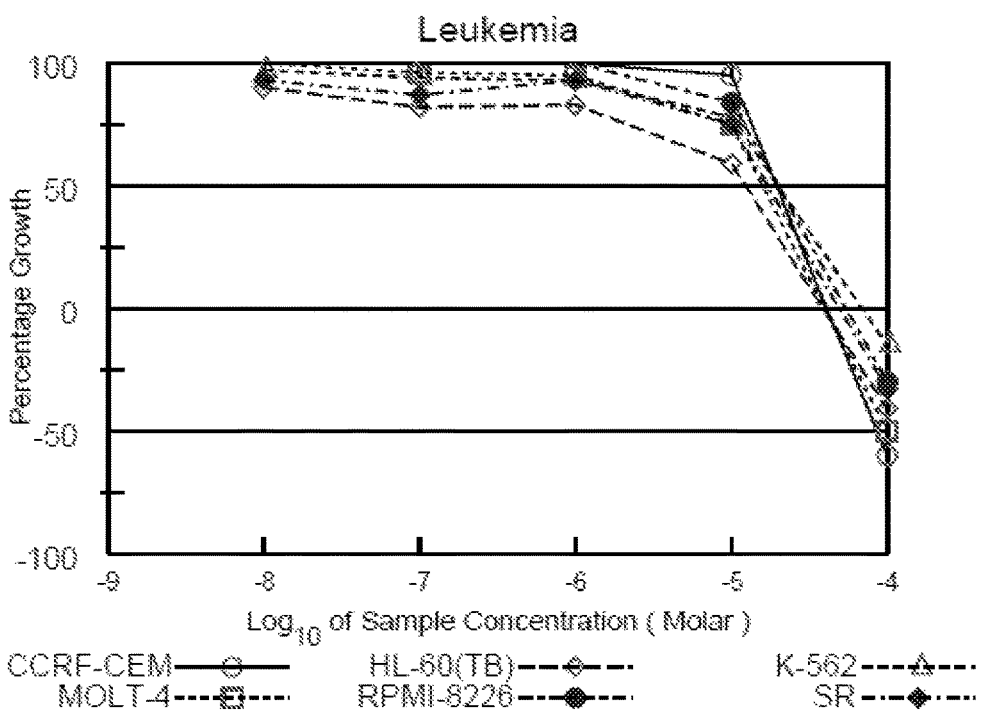
Figure 7B:
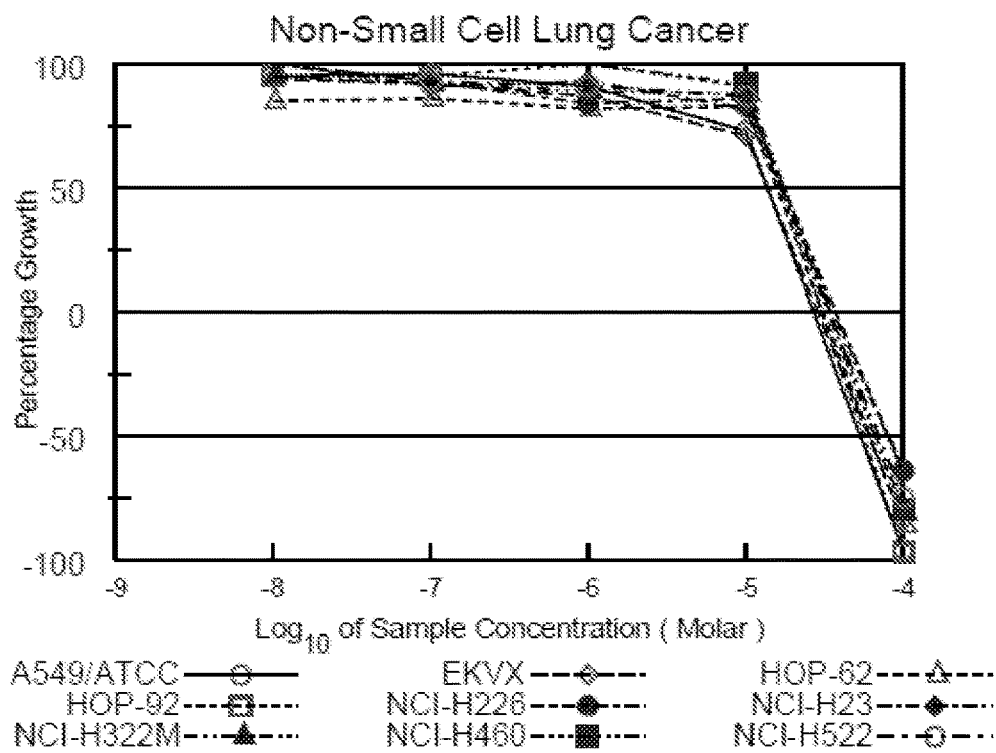
Figure 7C:
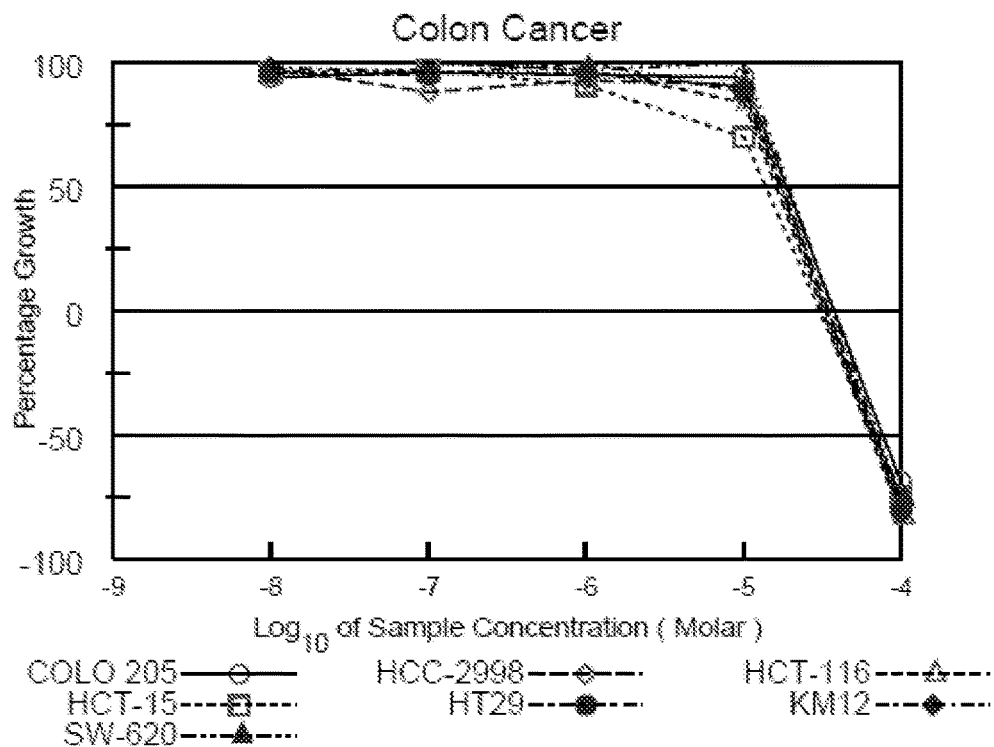
Figure 7D:
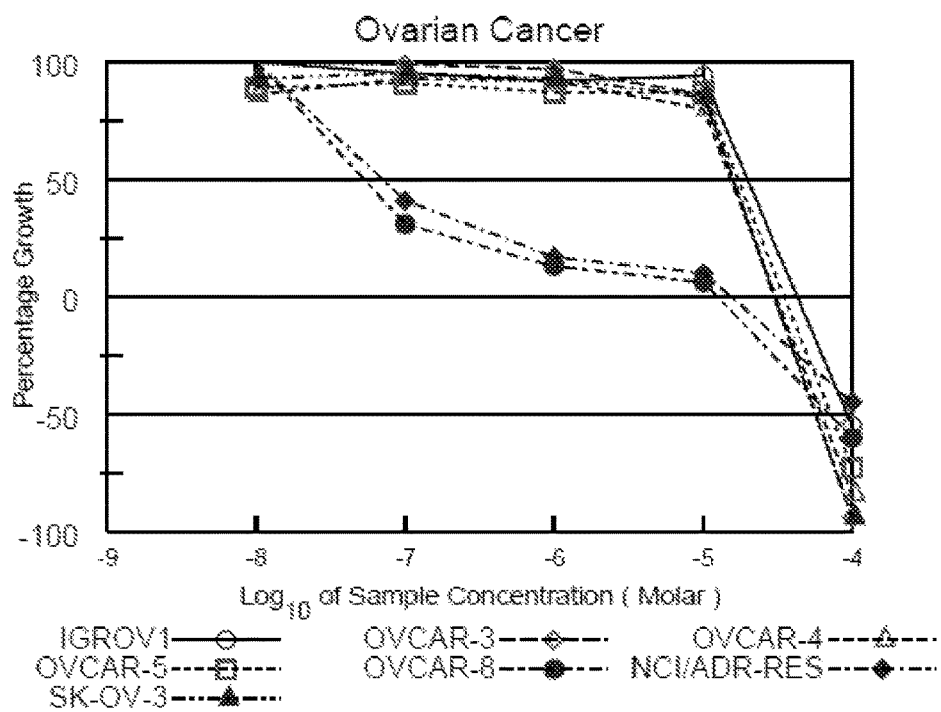
Figure 7E:
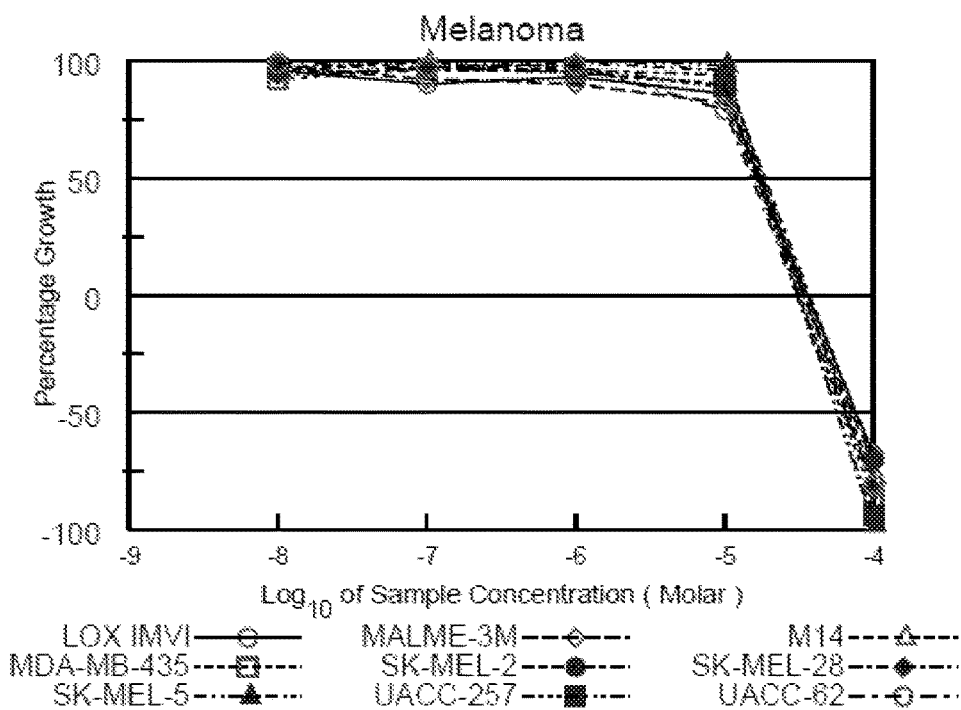
Figure 7G:
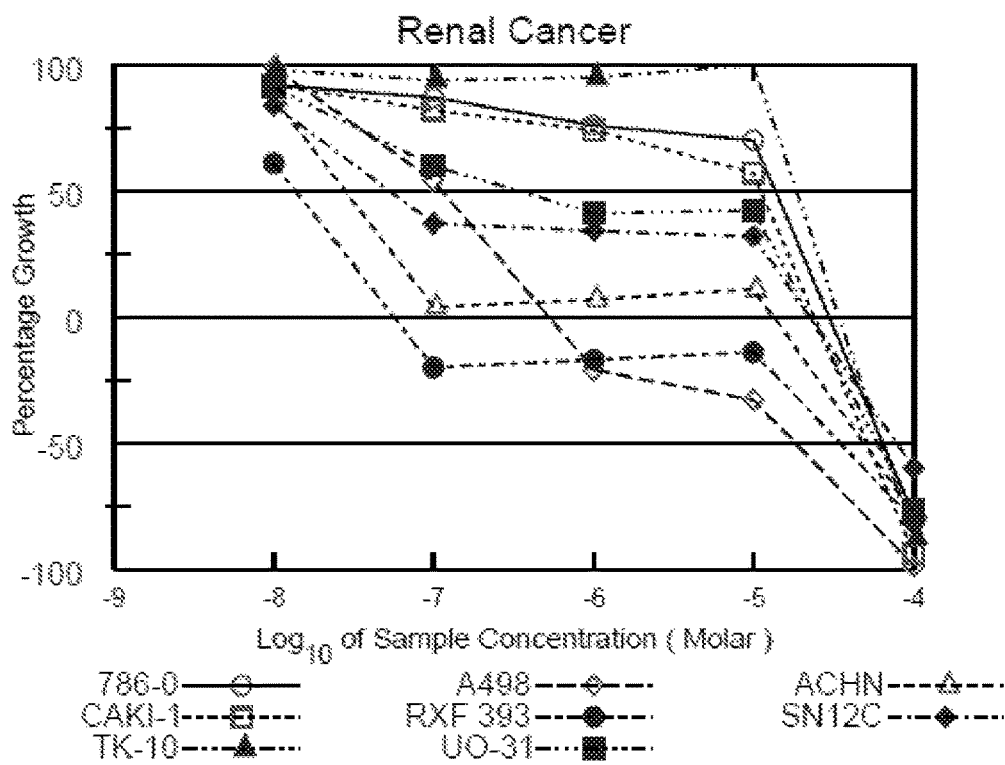
Figure 7H:
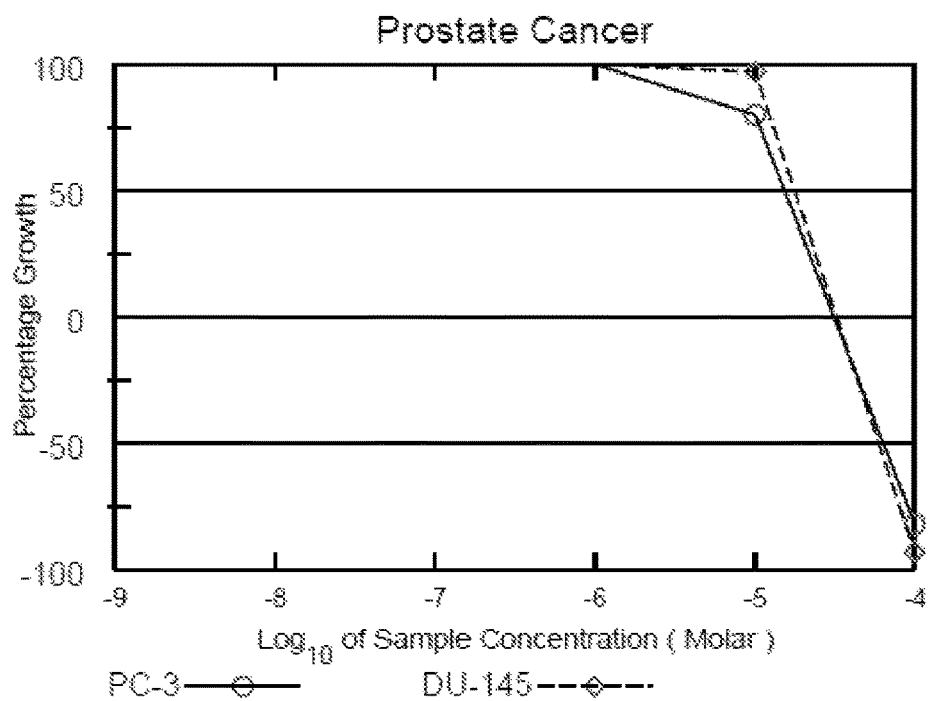
Figure 7I:
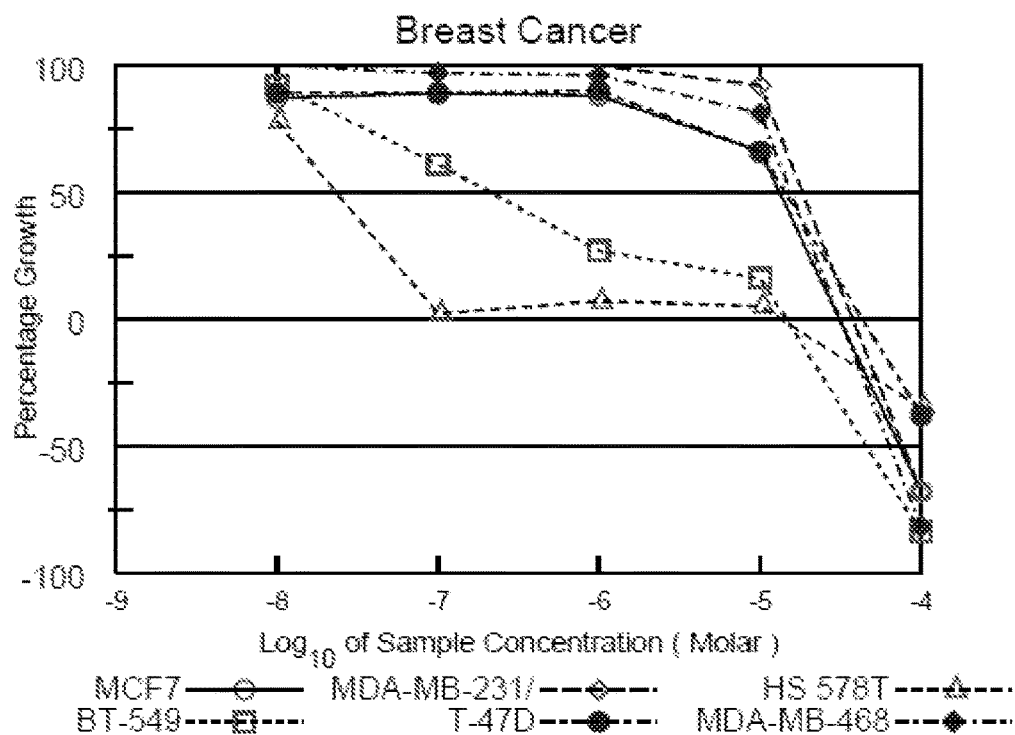
Figure 8A:
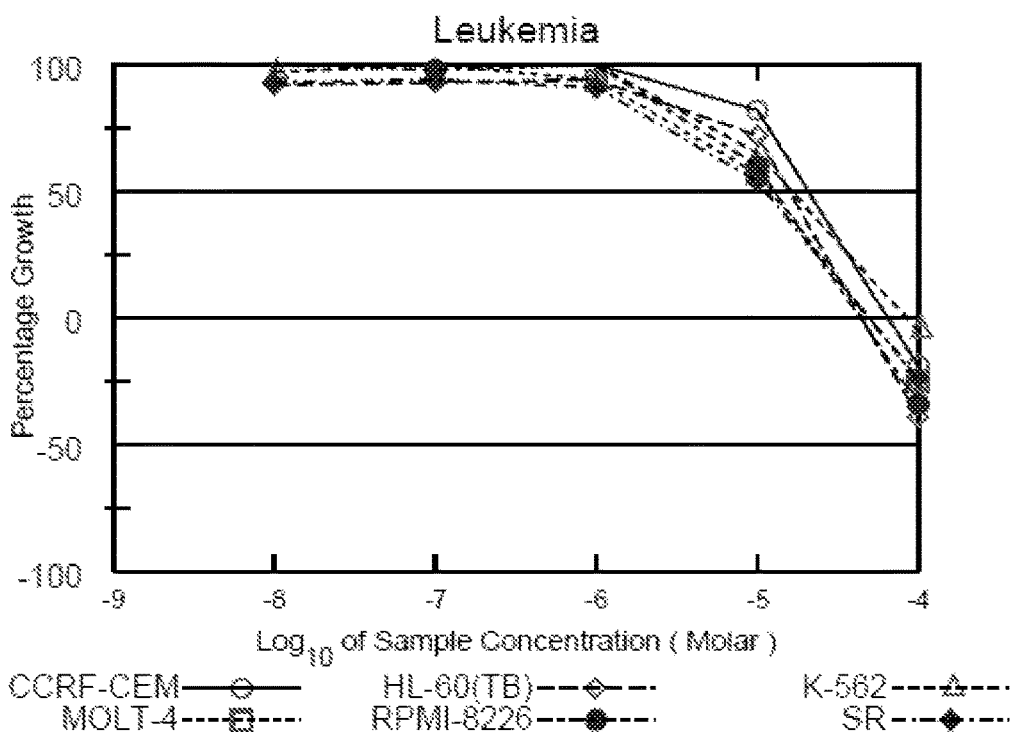
FIGS. 8A-8I depict the dose response curves for a compound formula (I) (i.e., (Ir)) against various cancer cell lines in the NCI 60-cell test.
Figure 8B:
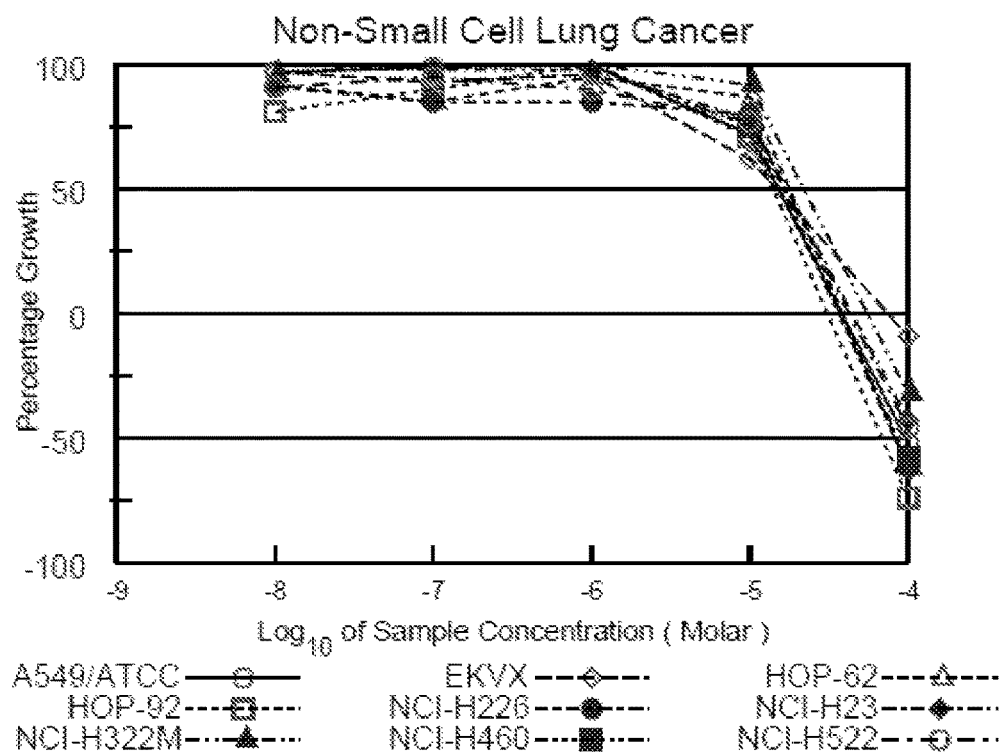
Figure 8C:
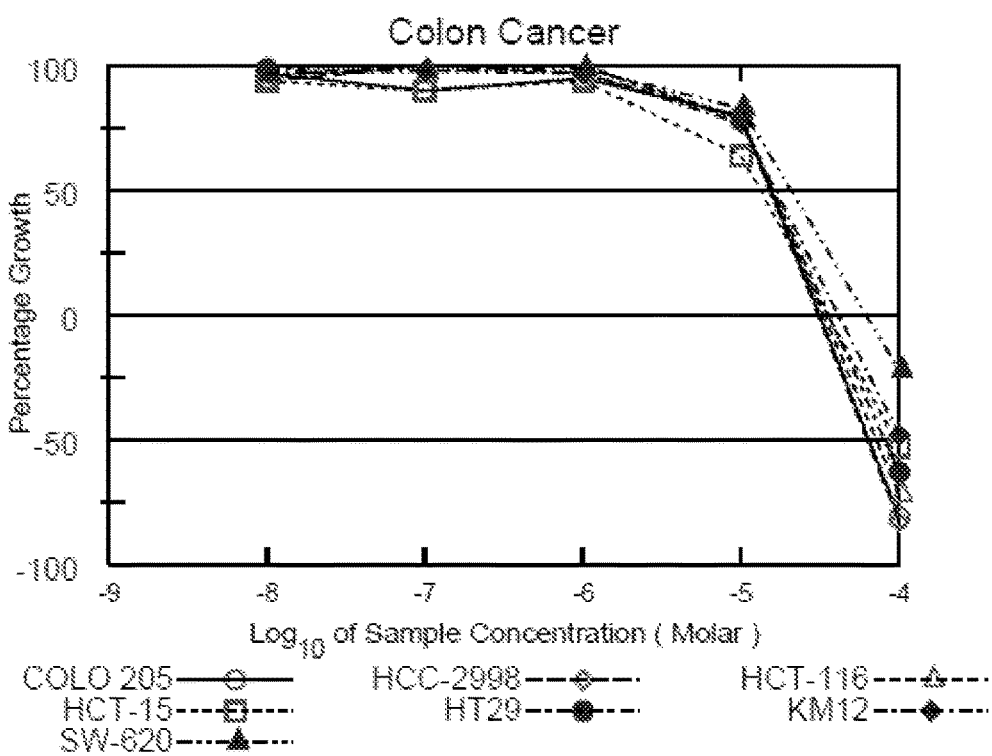
Figure 8D:
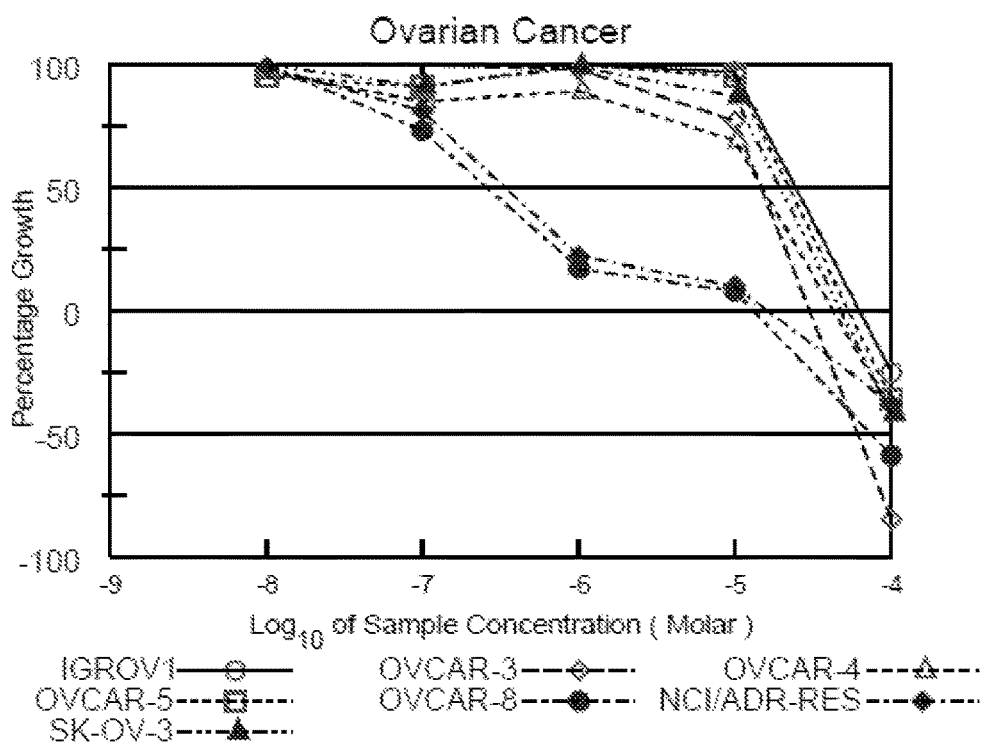
Figure 8E:
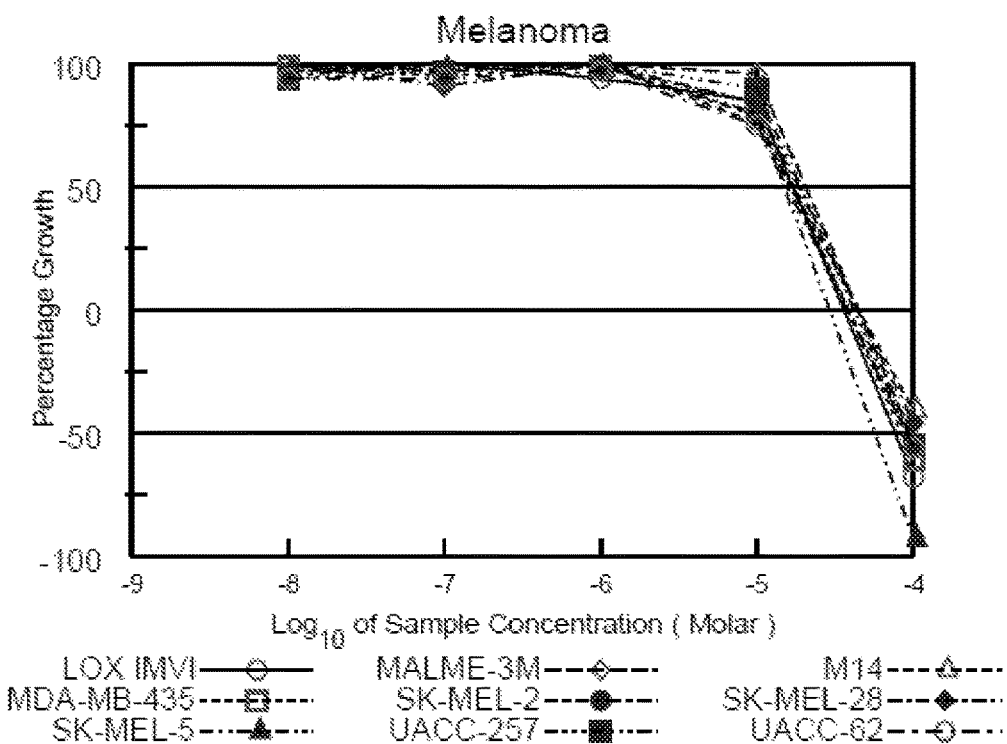
Figure 8F:
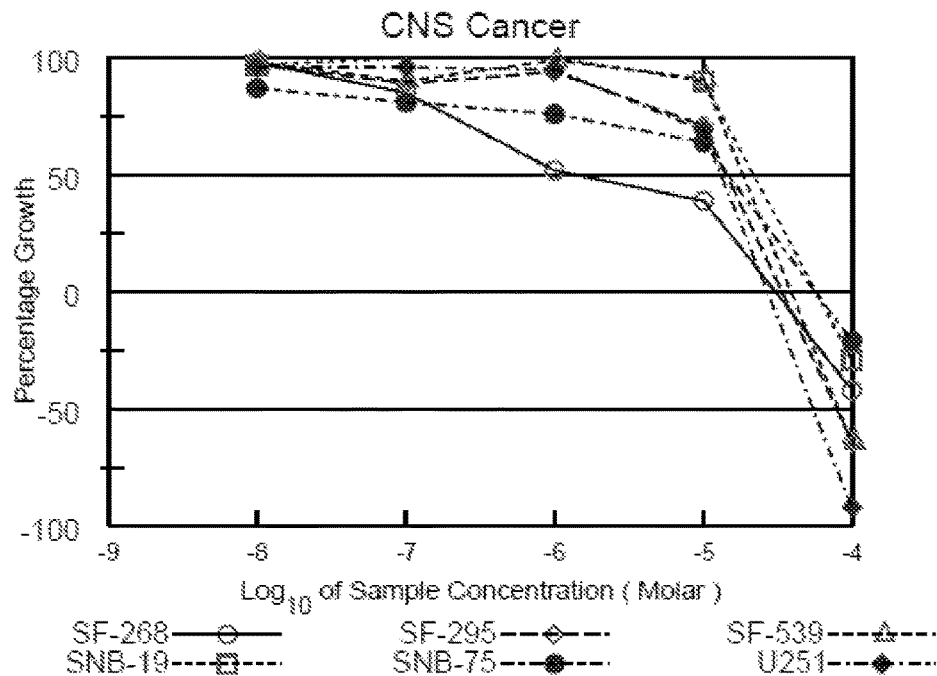
Figure 8G:
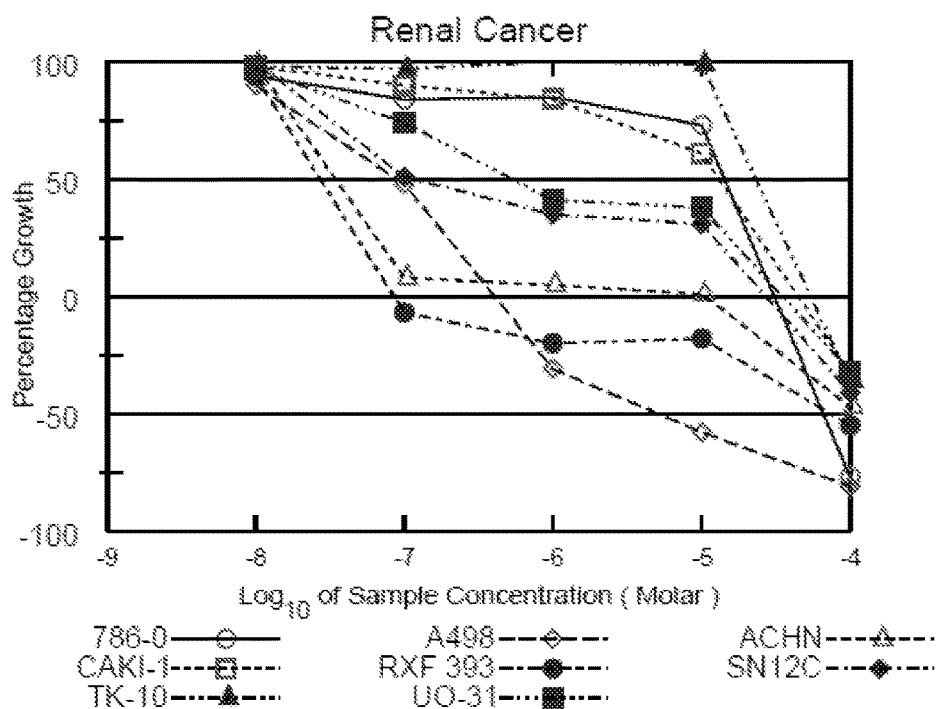
Figure 8H:
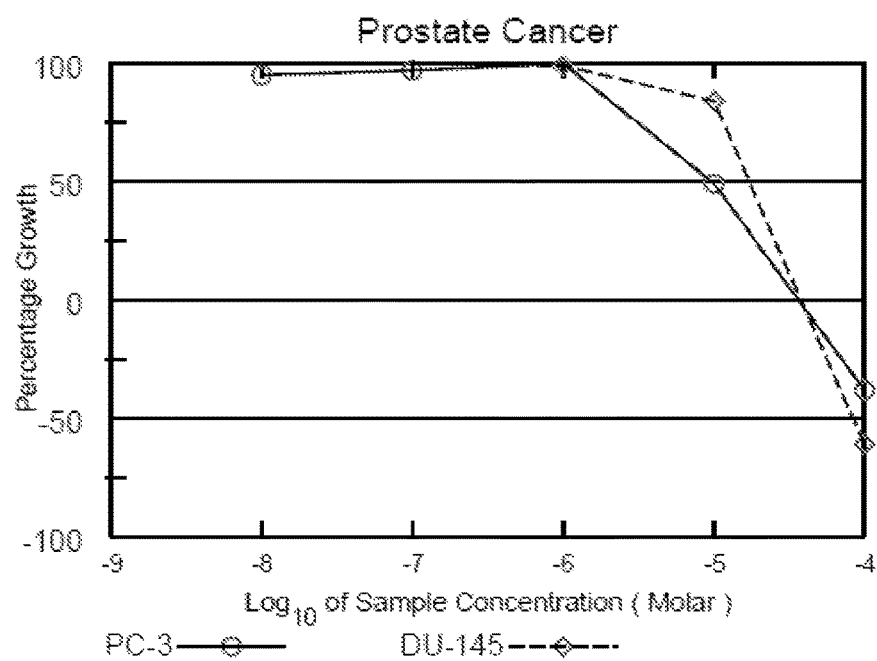
Figure 8I:
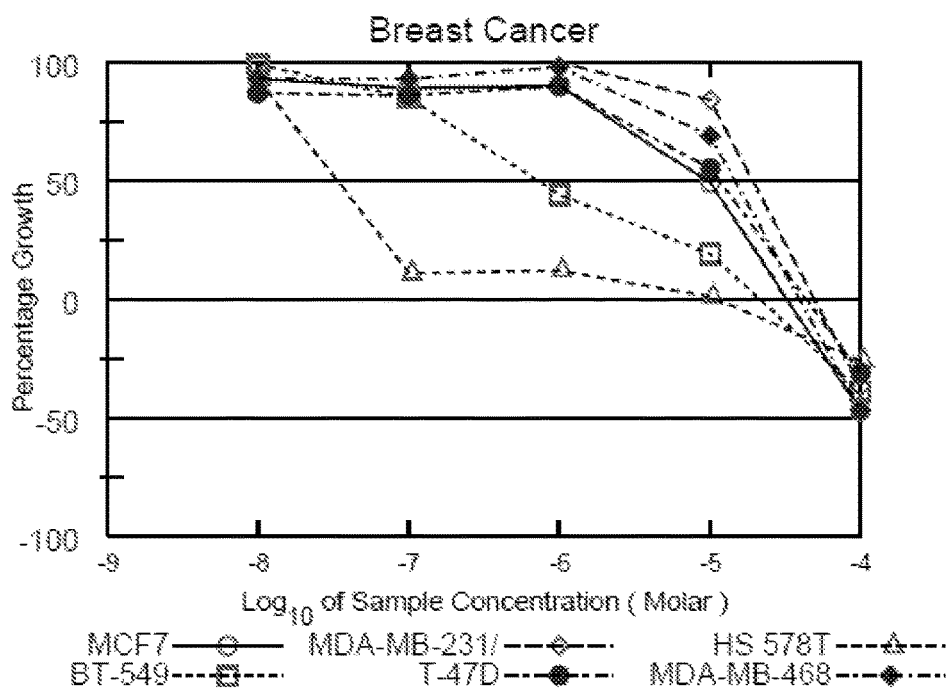

The compounds of formula (I), including a compound of formula (I'), can be prepared by any suitable synthetic methodology. Suitable methods are set forth in the general procedures described below, FIGS. 1-3, and the examples.

The methods described herein comprise administering a compound of formula (I), including a compound of formula (I'), or a pharmaceutically acceptable salt thereof in the form of a pharmaceutical composition. In particular, a pharmaceutical composition will comprise at least one compound of formula (I) or (I') or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I), including a compound of formula (I'), or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or (I') or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the compound of formula (I) in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compound of formula (I), including a compound of formula (I'), can be made into an injectable formulation. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I), including a compound of formula (I'), or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

It will be appreciated by a person of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.* 1980, 9, 467 and U.S. Pat. Nos. 4,235,871, 4,501,728, 4,837,028, and 5,019,369.

The dose administered to the mammal, particularly a human and other mammals, in accordance with the present invention should be sufficient to affect the desired response.

One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

The inventive methods comprise administering an effective amount of a compound of formula (I), including a compound of formula (I'), or a pharmaceutically acceptable salt thereof. An "effective amount" means an amount sufficient to show a meaningful benefit in an individual, e.g., promoting at least one aspect of tumor cell cytotoxicity (e.g., inhibition of growth, inhibiting survival of a cancer cell, reducing proliferation, reducing size and/or mass of a tumor (e.g., solid tumor)), or treatment, healing, prevention, delay of onset, inhibiting, halting, or amelioration of other relevant medical condition(s) and/or symptom associated with a particular disease (e.g., cancer, such as renal cancer, prostate cancer, or Ewing's sarcoma, diabetes, or human immunodeficiency virus (HIV)). The meaningful benefit observed in the mammal can be to any suitable degree (e.g., 10%, 20%, 30%, 40%, 50%, 60%, 70%, 80%, 90%, 95%, 99% or more). In some aspects, one or more symptoms of the disease (e.g., cancer, diabetes, or HIV) is prevented, reduced, ameliorated, inhibited, halted, or eliminated subsequent to administration of a compound of formula (I), including a compound of formula (I'), or a pharmaceutically acceptable salt thereof, thereby effectively treating the disease (e.g., cancer, diabetes, or HIV) to at least some degree.

Effective amounts may vary depending upon the biological effect desired in the individual, condition to be treated, and/or the specific characteristics of the compound of formula (I) or (I') or a pharmaceutically acceptable salt thereof, and the individual (e.g., a 70 kg patient on average). In this respect, any suitable dose of the compound of formula (I) or (I') or a pharmaceutically acceptable salt thereof can be administered to the mammal (e.g., human), according to the type of disease (e.g., cancer, diabetes, HIV) to be treated. Various general considerations taken into account in determining the "effective amount" are known to those of skill in the art and are described, e.g., in Gilman et al., eds., Goodman And Gilman's: *The Pharmacological Bases of Therapeutics*, 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or (I') or a pharmaceutically acceptable salt thereof desirably comprises about 0.001 mg per kilogram (kg) of the body weight of the mammal (mg/kg) to about 400 mg/kg. The minimum dose is any suitable amount, such as about 0.001 mg/kg, about 0.005 mg/kg, about 0.0075 mg/kg, about 0.01 mg/kg, about 0.05 mg/kg, about 0.075 mg/kg, about 0.1 mg/kg, about 0.15 mg/kg, about 0.2 mg/kg, about 0.4 mg/kg, about 0.75 mg/kg, about 1 mg/kg, about 2 mg/kg, about 3 mg/kg, about 5 mg/kg, about 10 mg/kg, about 15 mg/kg, about 20 mg/kg, about 30 mg/kg, about 50 mg/kg, about 60 mg/kg, about 75 mg/kg, about 100 mg/kg, about 150 mg/kg, about 175 mg/kg, about 200 mg/kg, about 250 mg/kg, about 275 mg/kg, or about 300 mg/kg). The maximum dose is any suitable amount, such as about 350 mg/mg, about 300 mg/kg, about 275 mg/kg, about 250 mg/kg, about 200 mg/kg, about 175 mg/kg, about 150 mg/kg, about 100 mg/kg, about 75 mg/kg, about 60 mg/kg, about 50 mg/kg, about 30 mg/kg, about 20 mg/kg, about 15 mg/kg, about 10 mg/kg, about 5 mg/kg, about 3 mg/kg, about 2 mg/kg, about 1 mg/kg, about 0.75 mg/kg, about 0.4 mg/kg, or about 0.2 mg/kg). Any two of the foregoing minimum and maximum doses can be used to define a close-ended range or can be used singly to define an open-ended range.

The invention also provides a method of treating cancer in a mammal comprising administering to the mammal an effective amount of a compound of formula (I), including a compound of formula (I'), or a pharmaceutically acceptable salt thereof. The cancer can be any suitable cancer, such as a highly glycolytic cancer (e.g., a highly glycolytic solid tumor). Suitable cancers include cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's sarcoma (tumor), leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001).

In some aspects, the cancer is leukemia, non-small cell lung cancer, colon cancer, melanoma, prostate cancer, renal cancer, breast cancer, CNS cancer, ovarian cancer, or Ewing's sarcoma, particularly renal cancer, prostate cancer, or Ewing's sarcoma.

In accordance with an embodiment of the invention, the compounds of formula (I), including compounds of formula (I'), are active against, e.g., decrease the growth of, renal cancer cell lines, e.g., 786-0, A-498, ACHN, CAKI-1, RXF 393, SN 12C, TK-10, and UO-31. For example, these compounds have a $GI_{50}$ or $IC_{50}$ of 1 μM or less, preferably 0.1 μM or less. Accordingly, the compounds of formula (I) are considered useful in treating renal cancer in a subject, particularly renal cancer that exhibits characteristics of a renal cancer cell line selected from 786-0, A-498, ACHN, CAKI-1, RXF 393, SN 12C, TK-10, and UO-31.

It is contemplated that a compound of formula (I), including a compound of formula (I'), can lower blood glucose levels. Without wishing to be bound by any theory, it is believed that a compound of formula (I) can increase expression of heat shock protein (HSP70), a marker of cell stress, and activate heat shock factor 1 (HSF1) in a PKCθ dose-dependent manner. Since PKCθ activation has been related to inducement of insulin resistance, it is contemplated that activation of HSP70 counteracts the insulin resistance induced by PKCθ activation. Accordingly, the invention further provides a method of treating diabetes (e.g., type 1 and/or type 2, particularly type 2) in a mammal in need thereof comprising administering to the mammal an effective amount of a compound of formula (I), including a compound of formula (I'), or a pharmaceutically acceptable salt thereof. The method of treating diabetes includes, e.g., treating or preventing insulin resistance, activating the transcriptional activity of heat shock factor 1 (HSF1), and/or inducing the expression of heat shock protein 70 (HSP70).

It is further contemplated that a compound of formula (I) can activate signaling pathways that are usually weakened in latent reservoirs of human immunodeficiency virus (HIV)-infected cells in vitro. Without wishing to be bound by any theory, it is believed that a compound of formula (I), including a compound of formula (I'), may sensitize HIV-infected patients to Highly Active Antiretroviral Therapy (HAART) by selectively activating viral replication in T cells, and with potentially limited toxicity due to the selectivity of a compound of formula (I) towards PKCθ, which is selectively expressed in tumors and immune cells (e.g., T cells). Thus, compounds of formula (I), including a compound of formula (I'), may be useful as an adjuvant therapy for a mammal infected with HIV or AIDS.

Accordingly, in accordance with an embodiment, a method of treating HIV in a mammal in need thereof comprising administering to the mammal an effective amount of a compound of formula (I), including a compound of formula (I'), or a pharmaceutically acceptable salt thereof is provided. In another embodiment, the invention provides a method of activating protein kinase C theta (PKCθ) in an HIV-infected mammal comprising administering to the mammal an effective amount of a compound of formula (I), including a compound of formula (I'), or a pharmaceutically acceptable salt thereof.

In accordance with some embodiments, the compound of formula (I), including a compound of formula (I'), or a pharmaceutically acceptable salt thereof is administered in combination with an anti-viral agent or combination of agents. For example, in some embodiments, the combinatorial formulation may include one or more compounds from a HAART protocol in combination with a compound of formula (I). Other combinatorial formulations may, for example, include a compound of formula (I) and/or compounds effective in treating the opportunistic infections of AIDS. In other embodiments, the combinatorial formulation may include one or more additional chemotherapeutic agents.

A compound of formula (I) or a pharmaceutically acceptable salt thereof can be administered, simultaneously or sequentially, in a coordinate treatment protocol with one or more of the secondary or adjunctive therapeutic agents contemplated herein. Thus, in certain embodiments compound of formula (I), including a compound of formula (I'), or a pharmaceutically acceptable salt thereof is administered coordinately with a different agent, or any other secondary or adjunctive therapeutic agent contemplated herein, using separate formulations or a combinatorial formulation as described above (i.e., comprising both compound of formula (I) or a pharmaceutically acceptable salt thereof and another therapeutic agent). This coordinate administration may be done simultaneously or sequentially in either order, and there may be a time period while only one or both (or all) active therapeutic agents individually and/or collectively exert their biological activities.

In one embodiment, such coordinate treatment methods may, for example, follow or be derived from various HAART protocols and include regimens such as, but not limited to, two nucleoside analogue reverse transcriptase inhibitors plus one or more protease inhibitor or non-nucleoside analogue reverse transcriptase inhibitor with a compound of formula (I), including a compound of formula (I'), or a pharmaceutically acceptable salt thereof. Other coordinate treatment methods may, for example, include a compound of formula (I) or a pharmaceutically acceptable salt thereof and/or treatments for opportunistic infections as well as compounds from HAART protocols. A distinguishing aspect of all such coordinate treatment methods is that the compound of formula (I) exerts at least some activity, which yields a favorable clinical response in conjunction with a complementary AIDS symptom decreasing, or distinct, clinical response provided by the secondary or adjunctive therapeutic agent. Often, the coordinate administration of the compound of with the secondary or adjunctive therapeutic agent will yield improved therapeutic or prophylactic results in the subject beyond a therapeutic effect elicited by the compound of formula (I), including a compound of formula (I'), or a pharmaceutically acceptable salt thereof, or the secondary or adjunctive therapeutic agent administered alone. This qualification contemplates both direct effects, as well as indirect effects.

Within exemplary embodiments, a compound of formula (I), including a compound of formula (I'), or a pharmaceutically acceptable salt thereof will be coordinately administered (simultaneously or sequentially, in combined or separate formulation(s)), with one or more secondary treating agents, or other indicated or adjunctive therapeutic agents, e.g., selected from, for example, protease inhibitors (e.g., saquinavir, indinavir, ritonavir, nelfinavir, atazanavir, darunavir, fosamprenavir, tipranavir and amprenavir); nucleoside reverse transcriptase inhibitors (e.g., zidovudine, didanosine, stavudine, lamivudine, zalcitabine, emtricitabine, tenofovir disoproxil fumarate, AVX754, and abacavir); non-nucleoside reverse transcriptase inhibitors (e.g., nevaripine, delavirdine, calanolide A, TMC125, and efavirenz); combination drugs (e.g., efavirenz/emtricitabine/tenofovir disoproxil fumarate, lamivudine/zidovudine, abacavir/lamivudine, abacavir/lamivudine/zidovudine, emtricitabine/tenofovir disoproxil fumarate, sulfamethoxazole/trimethoprim, and lopinavir/ritonavir); entry and fusion inhibitors (e.g., enfuvirtide, AMD070, BMS-488043, fozivudine tidoxil, GSK-873,140, PRO 140, PRO 542, Peptide T, SCH-D, TNX-355, and UK-427,857); treatments for opportunistic infections and other conditions associated with AIDS and HIV including (e.g., acyclovir, adefovir dipivoxil, aldesleukin, amphotericin b, azithromycin, calcium hydroxylapatite, clarithromycin, doxorubicin, dronabinol, entecavir, epoetin alfa, etoposide, fluconazole, ganciclovir, immunoglobulins, interferon alfa-2, ionomycine, isoniazid, itraconazole, megestrol, paclitaxel, peginterferon alfa-2, pentamidine, poly-1-lactic acid, ribavirin, rifabutin, rifampin, somatropin, testosterone, trimetrexate, and valganciclovir); integrase inhibitors (e.g., GS 9137, MK-0518); microbicides (e.g., BMS-378806, C31G, carbopol 974P, carrageenan, cellulose sulfate, cyanovirin-N, dextran sulfate, hydroxyethyl cellulose, PRO 2000, SPL7013, tenofovir, UC-781, and IL-2).

As used herein, the term "treat" does not necessarily imply complete elimination of a disease (e.g., cancer, diabetes, or HIV). Rather, there are varying degrees of treatment of which a person of ordinary skill in the art recognizes as having a benefit or therapeutic effect. In this respect, the cancer, diabetes, or HIV can be treated to any extent through the present inventive method. For example, in a method of treating cancer, at least 10% (e.g., at least 20%, 30%, or 40%) of the growth of a cancerous tumor desirably is inhibited upon administration of a compound described herein. Preferably, at least 50% (e.g., at least 60%, 70%, or 80%) of the growth of a cancerous tumor is inhibited upon administration of a compound described herein. More preferably, at least 90% (e.g., at least 95%, 99%, or 100%) of the growth of a cancerous tumor is inhibited upon administration of a compound described herein. In addition or alternatively, the inventive method may be used to inhibit metastasis of a cancer.

For purposes of the present invention, the subject to be treated typically is a mammal. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swine (pigs) or of the order Perssodactyla, including Equines (horses). In some aspects, the mammals are of the order Primates, Ceboids, or Simioids (monkeys) or of the order Anthropoids (humans and apes). In embodiments of the invention, the mammal is a human.

The following examples further illustrate the invention but, of course, should not be construed as in any way limiting its scope.

EXAMPLES

All reactions were carried out under argon unless otherwise specified. Solvents were dried using a Solvent Purification System (SPS) or using standard procedures. All catalysts were synthesized according to literature procedures (Amijs et al., *J. Org. Chem.* 2008, 73, 7721-7730; Ferrer et al., *Tetrahedron* 2007, 63, 6306-6316). The rest of the reagents were used directly as provided from the commercial sources. Analytical thin layer chromatography (TLC) was carried out using TLC aluminum sheets with 0.2 mm of silica gel (Merk $GF_{234}$). Flash chromatography purifications were carried out using flash grade silica gel (SDS Chromatogel 60 ACC, 40-60 µm) or using a COMBIFLASH™ Rf (Teledyne Isco, Lincoln, Nebr.) apparatus with REDISEP™ Rf (Teledyne Isco, Lincoln, Nebr.) normal phase silica columns. NMR (nuclear magnetic resonance) spectra were recorded at 23° C. on the following spectrometers: Bruker Avance 400 Ultrashield (400 MHz for $^1$H, and 101 MHz for $^{13}$C), and Bruker Avance 500 Ultrashield (500 MHz for $^1$H, and 126 MHz for $^{13}$C) (Bruker Corp., Billerica, Mass.). For some compounds $^{13}$C DEPT NMR spectra were provided instead of standard $^{13}$C NMR spectra. ESI (electrospray ionization) mass spectra were recorded on a Waters LCT Premier spectrometer (Waters Corp., Milford, Mass.). Optical rotations were measured on a P-1030 polarimeter (Jasco Inc., Easton, Md.). Chiral HPLC (high performance liquid chromatography) analysis was performed on an Agilent 1100 or Agilent 1200 apparatus (Agilent Technologies, Santa Clara, Calif.) using a CHIRALPAK™ IA column (4.6×250 mm) or a CHIRALPAK™ IC column (4.6×250 mm) (Daicel Corp., Osaka, Japan). Melting points were determined using a Mettler Toledo MP70 melting point apparatus (Mettler Toledo, Columbus, Ohio) and are uncorrected.

The compounds of the invention can be prepared following the general synthetic scheme shown in FIG. 1. The reagents and conditions for the chemical scheme of FIG. 1 are as follows: a) L-(+)-diethyl tartrate, Ti(OiPr)$_4$, tert-butylhydroperoxide, CH$_2$Cl$_2$, −40° C., 4 h, 9:1 e.r.; b) CCl$_4$, PPh$_3$, 80° C., 6 h; c) nBuLi (3.5 equiv), THF, −40° C., 2 h; d) TESOTf, Et$_3$N, CH$_2$Cl$_2$, 23° C., 3 h; e) AD-mix-α, tBuOH/H$_2$O (1:1), 23° C., 10 h.; f) NaIO$_4$/SiO$_2$, CH$_2$Cl$_2$, 23° C., 10 h; g) 4 (1.6 equiv), benzene, reflux, 2 days. h) LDA, R$_1$COMe, THF, −78° C., 15 h; i) [IPrAuNCPh]SbF$_6$ (3 mol %), CH$_2$Cl$_2$, 23° C., 5 h; j) TBAF, THF, 23° C., 12 h; k) DMAP, imidazole, TBDMSCl, 23° C.; l) CrO$_3$, pyridine, CH$_2$Cl$_2$, 23° C., 1 h and CeCl$_3$(H$_2$O)$_7$, NaBH$_4$, MeOH, 23° C., 5 min; m) WCl$_6$ (2 equiv), nBuLi (4 equiv), THF, 0 to 50° C., 2 h; n) R$_5$COCl, DMAP, Et$_3$N, CH$_2$Cl$_2$, 45° C. 4-12 h and TBAF, THF, 23° C., 12 h; o) R$_2$COOH, DMAP, NEt$_3$, 2,4,6-trichlorobenzoyl chloride, toluene, 23° C., 1 h and TBAF, AcOH, THF, 4 h, 23° C.

The following examples describe the preparation of compounds of formula (I), in which X$_1$ is O, R$_3$ is methyl, and R$_4$ is methyl. As will become apparent to the skilled in the art person, the careful selection of the starting materials will allow for the preparation of other compounds of formula (I).

Preparative Example 1

This example demonstrates the scale up to 50 g of the first steps (a-g) of the synthesis by the introduction of minor changes to the previously described syntheses (Molawi et al., *Angew. Chem. Int. Ed.* 2010, 122, 3595-3597; Mohapatra et al., *Eur. J. Org. Chem.* 2007, 5059-5063) in an embodiment of the invention. See FIG. 2.

Steps a) through g) are set forth in detail below.
Step a)

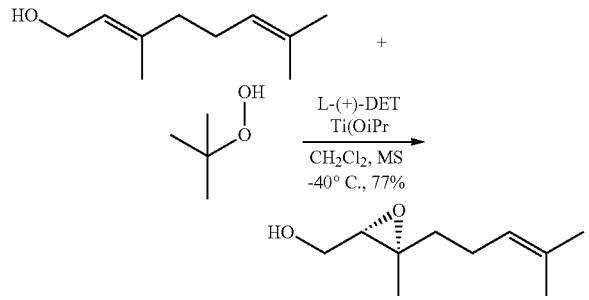

Dry CH$_2$Cl$_2$ (350 mL) was added to a flame-dried three-necked 1 L flask containing activated 4 Å molecular sieves (powder) and provided with an Argon inlet, an addition funnel and a thermometer. After cooling to −20° C., previously distilled L-(+)-diethyl tartrate (8.0 mL, 0.47 mol) was added dropwise through the addition funnel. Then, the addition funnel was rinsed with dry CH$_2$Cl$_2$ (10 mL) before being charged with previously distilled titanium (IV) isopropoxide (9.3 mL, 31.8 mmol), after its dropwise addition the same operation was repeated with tert-butyl hydroperoxide (solution 5.5 M in decane, 235 mL, 1.3 mol). The mixture was stirred at this temperature for 20 min before being cooled to −40° C., then a solution of previously distilled geraniol (50 g, 0.32 mol) in CH$_2$Cl$_2$ (80 mL) was slowly added by an addition funnel and the final mixture was left reacting at this stated temperature for 4 h. After this time TLC analysis showed no starting material left. Water (100 mL) was slowly added and the reaction was left to reach room temperature. Then an aqueous solution containing NaOH (30%) and NaCl (5%) was added, the mixture was left stirring for 1 h before being filtered by a three layers bed of silica+CELITE™+silica eluting with extra CH$_2$Cl$_2$. The filtrated was transferred to a separation funnel and the layers separated. The aqueous layer was further extracted with CH$_2$Cl$_2$ (×3) and the combined organic layers washed with water and brine, then dried over anhydrous Na$_2$SO$_4$, filtered and concentrated under reduced pressure. The crude was purified through vacuum distillation (1.7 mbar, 80-82° C.) affording the pure product as a colorless oil in 77% yield (42.4 g, 0.25 mol).

The enantiomeric ratio was determined by protection of the alcohol moiety with a tosyl group (following the procedure described by Nakatsuji et al. (*Org. Lett.* 2008, 10, 2131-2134) spectroscopic data of the product is in accordance with previously reported in Riou et al. (*J. Org. Chem.* 2008, 73, 7436-7439), its analysis by chiral HPLC showed an enantiomeric ratio of 9:1 (Agilent HPLC 1100, Chiral-Pack IA, room temperature 11.91 min (major), 14.57 min (minor) (Agilent Technologies, Santa Clara, Calif.)).
Step b)

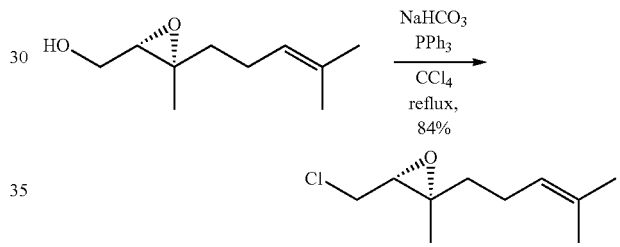

CCl$_4$ (430 mL, 4.4 mol) was added into a 3-necked 1 L flask connected to a refrigerant, an Argon inlet and a thermometer, containing ((2S, 3S)-3-methyl-3-(4-methylpen-3-en-1yl)oxiran-2-yl)methanol (35 g, 0.20 mol). Triphenylphosphine (64.7 g, 0.25 mol) and sodium hydrogen carbonate (3.45 g, 41.1 mmol) were added portionwise and the mixture was heated to reflux (82° C. internal temperature) during 5 h. TLC control showed no starting material left. Cyclohexane (100 mL) was added and the crude filtered through a pad of CELITE™. Then the solvent was evaporated under reduced pressure and washed again with cyclohexane (100 mL) and filtered through CELITE™. After solvent evaporation the pure product was afforded as colorless oil in 84% yield (32.5 g, 0.17 mol) by vacuum distillation (0.9 mbar, 74-76° C.).
Step c)

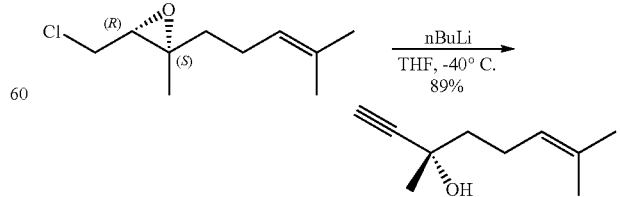

(2S,3R)-3-(chloromethyl)-2-methyl-2-(4-methylpent-3-en-1yl)oxirane (32.5 g, 0.17 mol) was dissolved in 240 mL of dry THF and the solution was transferred to a 3-necked 1 L flask connected to an addition funnel. The flask was refrigerated to −40° C. and then 320 mL of nBuLi (1.3 M solution in hexanes, 0.42 mol) were added dropwise through the addition funnel. After the addition (ca. 1 h) the mixture was left stirring for 30 min. The reaction was quenched by careful addition of aqueous saturated NH$_4$Cl solution (200 mL) at −40° C. Then the mixture was allowed to reach room temperature and the layers were separated, the aqueous layer was further extracted with Et$_2$O (twice) and the combined organic layers washed with saturated NH$_4$Cl solution and brine, dried over anhydrous Na$_2$SO$_4$, filtered and concentrated under vacuum. The resulting crude was distilled under reduced pressure (72° C., 1.8 mbar) affording a pale yellow oil in 88% yield (23.1 g, 0.15 mol).

Step d)

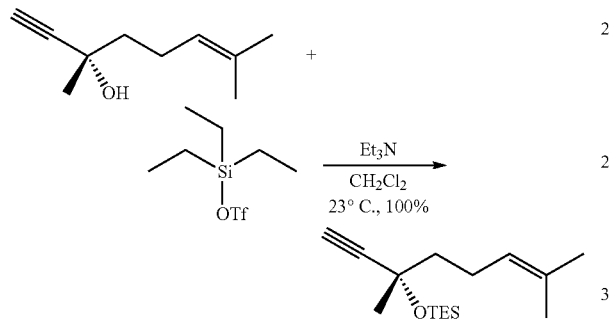

(S)-3,7-dimethyloct-6-en-1-yn-3-ol (23.0 g, 0.15 mol) was dissolved in dry CH$_2$Cl$_2$ (230 mL), Et$_3$N (38 mL, 0.27 mol) was added and the solution was cooled to 0° C. in an ice bath. Then TESOTf (37.6 mL, 0.17 mol) was added dropwise through an addition funnel. After the addition, the reaction was left to reach room temperature (22° C.) and left stirring for 12 h. Aqueous saturated NH$_4$Cl solution (100 mL) was added and the layers separated. The aqueous layer was further extracted twice with CH$_2$Cl$_2$, the combined organic layers washed with brine, dried over Na$_2$SO$_4$, and concentrated in vacuo. The crude was purified by filtration through a silica column eluting with cyclohexane. 40.3 g of a pale yellow oil were obtained (quant., 0.15 mol).

Step e)

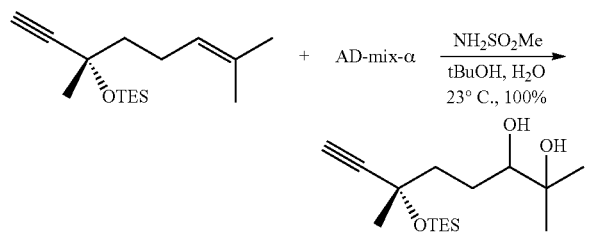

A solution of (S)-(3-7-dimethyloct-6-en-1-yn-3-yloxy)triethylsilane (40 g, 0.15 mol) in tert-butanol (40 mL) was added at 0° C. to a stirring solution of AD-mix-α (210 g) and methanesulfonamide (14.3 g, 0.15 mol) in a mixture of tert-butanol (520 mL) and water (520 mL). After the addition the reaction was left stirring at room temperature (23° C.) for 12 h. Na$_2$SO$_3$ (200 g) was added at 0° C., and the mixture was left stirring for 3 extra hours. Then the two layers were separated. The aqueous layer was further extracted with EtOAc (×3) and the combined organic layers washed twice with KOH (2M) solution and dried over anhydrous Na$_2$SO$_4$. After solvent evaporation, a yellow oil was obtained (45.0 g, 100%, 0.15 mol) and used without further purification.

Steps f) and g)

Steps f) and g) for the synthesis of products 3a and 5a were reproduced at 10 g scale as already previously described (Molawi et al., *Angew. Chem. Int. Ed.* 2010, 122, 3595-3597).

Preparative Example 2

This example demonstrates the general procedures for derivatizing the C7-position of the englerin core in an embodiment of the invention. See FIG. 3.

Step h)

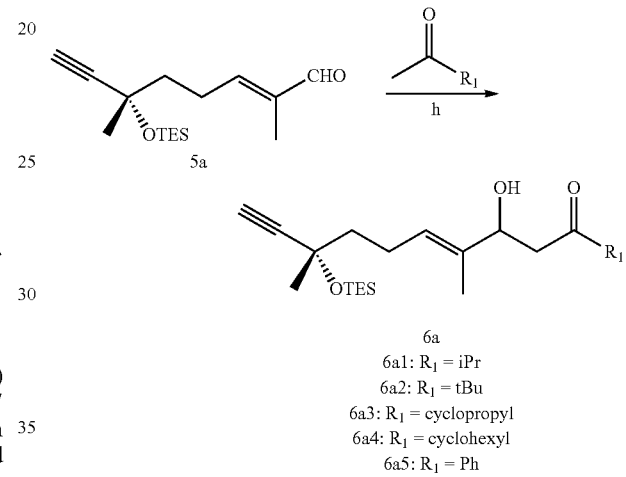

6a
6a1: R$_1$ = iPr
6a2: R$_1$ = tBu
6a3: R$_1$ = cyclopropyl
6a4: R$_1$ = cyclohexyl
6a5: R$_1$ = Ph General procedure A (aldol reaction): a solution of diisopropylamine (1.8 equiv) in THF (0.25 M) was cooled to 0° C. in a water-ice bath. Then a solution of nBuLi in hexanes (1.4 M, 1.6 equiv) was added through a syringe pump over 30 minutes. The mixture was stirred in the water-ice bath for 30 extra min and then cooled to −78° C. At this temperature a solution of the methylketone of formula R$_1$COMe (1.5 equiv) in THF (0.25 M) was added dropwise over 30 min (syringe pump, internal temperature kept under −70° C. at all times). The solution was stirred at −78° C. for 2 h before a solution of (S,E)-2,6-dimethyl-6-(triethylsilyloxy)oct-2-en-7-ynal (5a) (1 equiv) in THF (0.1 M) was added dropwise over 10 min. The resulting mixture was stirred 15 h at −78° C. and then quenched at the same temperature with saturated aqueous NH$_4$Cl solution (7 mL for mmol), added slowly over 30 min, keeping temperature under −30° C. After complete addition, the mixture was allowed to reach room temperature. EtOAc was added, and the layers were separated. The aqueous layer was extracted twice with EtOAc, and the combined organic layers were dried over Na$_2$SO$_4$, filtered, and concentrated under vacuum. The crude oil obtained was purified by silica flash chromatography.

Preparative Example 2-1

This example demonstrates the synthesis of (10S,E)-5-hydroxy-2,6,10-trimethyl-10-((triethylsilyl)oxy)dodec-6-en-11-yn-3-one (6a1) in an embodiment of the invention. See FIG. 3.

The desired product was synthesized according to general procedure A from 3-methyl-2-butanone (3.1 mL, 29.0 mmol) and (S,E)-2,6-Dimethyl-6-(triethylsilyloxy)oct-2-en-7-ynal (5a) (5.22 g, 18.6 mmol). The crude oil obtained was purified by column chromatography (cyclohexane:EtOAc: Et$_3$N, 20:1:0.1) to yield the enynone product as a pale yellow oil (5.35 g, 78%).

$^1$H-NMR (400 MHz, CDCl$_3$) δ 5.50 (t, J=7.2 Hz, 1H), 4.46 (dd, J=5.6, 2.8 Hz, 1H), 3.00 (dd, J=2.8, 0.8 Hz, 1H), 2.71-2.61 (m, 3H), 2.43 (s, 1H), 2.30-2.20 (m, 2H), 1.70-1.65 (m, 2H), 1.67 (s, 3H), 1.48 (s, 3H), 1.13 (d, J=7.2 Hz, 6H), 0.97 (t, J=8.0 Hz, 9H), 0.71-0.66 (m, 6H). $^{13}$C-NMR (101 MHz, CDCl$_3$) δ 215.6, 135.7, 126.9, 88.0, 72.9, 71.8, 68.7, 45.3, 44.7, 41.5, 30.9, 22.9, 17.96, 17.93, 11.9, 6.9, 6.0.

Preparative Example 2-2

This example demonstrates the synthesis of (10S,E)-5-hydroxy-2,2,6,10-tetramethyl-10-((triethylsilyl)oxy)dodec-6-en-1-yn-3-one (6a2) in an embodiment of the invention. See FIG. 3.

Use of 2,2-dimethyl-3-butanone (0.61 mL, 4.68 mmol) in general procedure A provided access to product 6a2, which was obtained as a yellow oil (930 mg, 80%) after purification by flash chromatography on silica (+1% NEt$_3$) eluting with cyclohexane:EtOAc mixtures from 9:1 to 8:2.

$^1$H-NMR (400 MHz, CDCl$_3$) δ 5.50 (m, 1H), 4.43 (m, 1H), 3.18 (d, J=2.0 Hz, 1H), 2.70 (d, J=6.0 Hz, 2H), 2.43 (s, 1H), 2.40-2.22 (m, 2H), 1.70-1.60 (m, 1H), 1.66 (s, 3H), 1.48 (s, 3H), 1.17 (s, 9H), 0.98 (t, J=8.0 Hz, 9H), 0.72-0.66 (m, 6H). $^{13}$C-NMR (101 MHz, CDCl$_3$) δ 217.3, 135.7, 125.9, 88.1, 72.9, 71.8, 68.7, 44.7, 44.4, 41.8, 30.9, 26.2, 22.9, 12.1, 6.9, 6.0. HRMS-ESI calculated for C$_{22}$H$_{40}$O$_3$SiNa (M+Na)$^+$: 403.2639; found: 403.2642.

Preparative Example 2-3

This example demonstrates the synthesis of (8S,E)-1-cyclopropyl-3-hydroxyl-4,8-dimethyl-8-((triethylsilyl)oxy)dec-4-en-9-yn-1-one (6a3) in an embodiment of the invention. See FIG. 3.

The desired product was obtained from 1-cyclopropyl-heptanone (0.21 mL, 2.13 mmol) and (S,E)-2,6-dimethyl-6-(triethylsilyloxy)oct-2-en-7-ynal 5a (0.4 g, 1.43 mmol) according to general procedure A. The product was obtained as a colorless oil in 91% yield (504 mg) after purification by flash chromatography on silica (+1% NEt$_3$) eluting with cyclohexane:EtOAc mixtures from 95:5 to 8:2.

$^1$H-NMR (500 MHz, CDCl$_3$) δ 5.45-5.55 (m, 1H), 4.48 (dt, J=7.7, 3.3 Hz, 1H), 3.00 (d, J=2.7 Hz, 1H), 2.87-2.70 (m, 3H), 2.41 (s, 1H), 2.27-2.16 (m, 2H), 1.96-1.91 (m, 1H), 1.69-1.62 (m, 2H), 1.66 (s, 3H), 1.46 (s, 3H), 1.10-1.06 (m, 2H), 0.99-0.91 (m, 12H), 0.71-0.66 (m, 6H). $^{13}$C-NMR (126 MHz, CDCl$_3$) δ 211.6, 135.6, 126.0, 88.1, 72.9, 71.8, 68.7, 48.3, 44.7, 30.9, 22.9, 21.3, 12.0, 11.3, 11.1, 7.0, 6.1. HRMS-ESI calculated for C$_{21}$H$_{36}$O$_3$SiNa (M+Na)$^+$: 387.2326; found: 387.2333.

Preparative Example 2-4

This example demonstrates the synthesis of (8S,E)-1-cyclohexyl-3-hydroxy-4,8-dimethyl-8-((triethylsilyl)oxy)-4-en-9-yn-1-one (6a4) in an embodiment of the invention. See FIG. 3.

Compound 6a4 was obtained following general procedure A from cyclohexyl methyl ketone (0.68 mL, 4.69 mmol) and (S,E)-2,6-dimethyl-6-(triethylsilyloxy)oct-2-en-7-ynal (5a) (0.9 g, 3.13 mmol). A yellow oil was obtained in 78% yield (962 mg) after purification on silica gel (+1% Et$_3$N, mixtures cyclohexane:EtOAc, 9:1 to 8:2).

$^1$H-NMR (400 MHz, CDCl$_3$) δ 5.47 (m, 1H), 4.43 (dt, J=8.4, 2.8 Hz, 1H), 3.02 (d, J=2.4 Hz, 1H), 2.56-2.70 (m, 2H), 2.42 (s, 1H), 2.39-2.30 (m, 1H), 2.26-2.16 (m, 2H), 1.89-1.79 (m, 4H), 1.70-1.63 (m, 3H), 1.65 (s, 3H), 1.48 (s, 3H), 1.38-1.20 (m, 5H), 0.98 (t, J=8.0 Hz, 9H), 0.72-0.66 (m, 6H). $^{13}$C-NMR (101 MHz, CDCl$_3$) δ 215.1, 135.7, 125.9, 88.1, 72.9, 71.8, 68.7, 51.5, 45.6, 44.7, 30.9, 28.3, 25.8, 25.6, 22.9, 12.0, 7.0, 6.1. HRMS-ESI calculated for C$_{24}$H$_{42}$O$_3$SiNa (M+Na)$^+$: 429.2795; found: 429.2798.

Preparative Example 2-5

This example demonstrates the synthesis of (8S,E)-3-hydroxy-4,8-dimethyl-1-phenyl-8-((triethylsilyl)oxy)dec-4-en-9-yn-1-one (6a5) in an embodiment of the invention. See FIG. 3.

General procedure A using acetophenone (0.36 mL, 3.13 mmol), and other reagents amounts recalculated accordingly, afforded the desired product 6a5 as a yellow oil after purification (560 mg, 70%).

$^1$H-NMR (400 MHz, CDCl$_3$) δ 8.0-7.97 (m, 2H), 7.62-7.58 (m, 1H), 7.52-7.47 (m, 2H), 5.56 (t, J=7.2 Hz, 1H), 4.67-4.64 (m, 1H), 3.22-3.12 (m, 1H), 3.11 (d, J=0.8 Hz, 1H), 2.44 (s, 1H), 2.30-2.23 (m, 2H), 1.74 (s, 3H), 1.72-1.60 (m, 2H), 1.44 (s, 3H), 1.00 (t, J=8.0 Hz, 9H), 0.74-0.67 (m, 6H). $^{13}$C-NMR (101 MHz, CDCl$_3$) δ 200.6, 136.8, 135.7, 133.4, 128.6, 128.12, 126.2, 88.1, 73.0, 71.8, 68.7, 44.7, 43.8, 30.9, 22.9, 12.1, 7.0, 6.1. HRMS-ESI calculated for C$_{24}$H$_{36}$O$_3$SiNa (M+Na)$^+$: 423.2326; found: 423.2306.

Preparative Example 3

Step i)

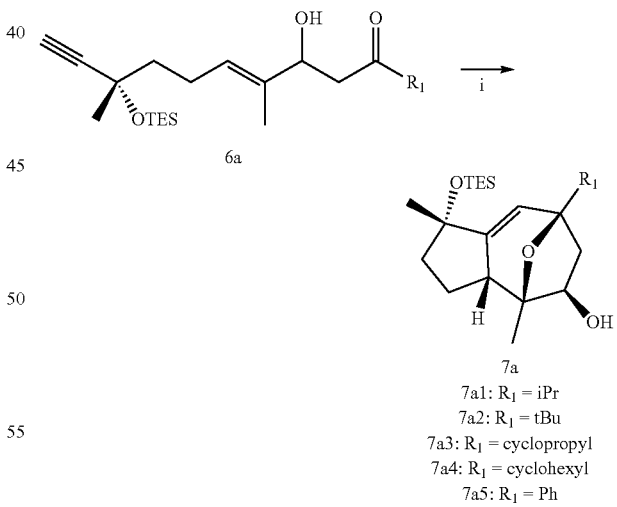

6a 7a
7a1: R$_1$ = iPr
7a2: R$_1$ = tBu
7a3: R$_1$ = cyclopropyl
7a4: R$_1$ = cyclohexyl
7a5: R$_1$ = Ph General procedure B (gold(I)-catalyzed cyclization): [IPrAuNCPh][SbF6] (Amijs et al., J. Org. Chem. 2008, 73, 7721-7730) (0.03 equiv) was added at room temperature to a solution of the corresponding enynone 6a in dry CH2Cl2 (0.1 M) (Molawi et al., Angew. Chem. Int. Ed. 2010, 122, 3595-3597) containing 3 Å molecular sieves under argon atmosphere. The reaction was stirred under completion (3-8 h) and then quenched with Et$_3$N. After solvent evaporation under vacuum, the crude was purified by silica chromatography (mixtures cyclohexane:EtOAc, 9:1 to 1:1) to obtain the pure tricycle compound as a single diastereoisomer.

Preparative Example 3-1

This example demonstrates the synthesis of (1S,3aR,4S,5R,7R)-1, (1S,3aR,4S,5R,7R)-7-isopropyl-1,4-dimethyl-1-((triethylsilyl)oxy)-1,2,3,3a,4,5,6,7-octahydro-4,7-epoxyazulen-5-ol (7a1) in an embodiment of the invention. See FIG. 3.

Compound 7a1 was obtained as a colorless oil following general procedure B from (8S,E)-1-cyclohexyl-3-hydroxy-4,8-dimethyl-8-(triethylsilyloxy)-4-en-9-yn-1-one (6a1) as previously described in Molawi et al., *Angew. Chem. Int. Ed.* 2010, 122, 3595-3597.

Preparative Example 3-2

This example demonstrates the synthesis of (1S,3aR,4S,5R,7R)-7-(tert-butyl)-1,4-dimethyl-1-((triethylsilyl)oxy)-1,2,3,3a,4,5,6,7-octahydro-4,7-epoxyazulen-5-ol (7a2) in an embodiment of the invention. See FIG. 3.

Use of (10S,E)-5-Hydroxy-2,2,6,10-tetramethyl-10-(triethylsilyloxy)dodec-6-en-11-yn-3-one, 6a2 (507.2 mg, 1.33 mmol) following the general procedure B allowed the access to (1S,3aR,4S,5R,7R)-7-(tert-butyl)-1,4-dimethyl-1-((triethylsilyl)oxy)-1,2,3,3a,4,5,6,7-octahydro-4,7-epoxyazulen-5-ol (7a2) as a colorless oil (56.7 mg, 11% yield).

$^{1}$H-NMR (500 MHz, CDCl$_3$) δ 5.73 (d, J=3.0 Hz, 1H), 4.11 (t, J=6.6 Hz, 1H), 2.74-2.68 (m, 1H), 2.59-2.54 (m, 1H), 1.75-1.68 (m, 3H), 1.50-1.30 (m, 2H), 1.30 (s, 3H), 1.28 (s, 3H), 0.99-0.94 (m, 9H), 0.98 (s, 9H), 0.63-0.54 (m, 6H). $^{13}$C-NMR (126 MHz, CDCl$_3$) δ 147.3, 119.4, 85.4, 84.8, 79.5, 74.2, 47.6, 47.3, 40.9, 34.2, 28.6, 25.4, 22.8, 20.4, 7.3, 6.9. HRMS-ESI calculated for C$_{22}$H$_{40}$O$_3$SiNa (M+Na)$^+$: 403.2639; found: 403.2633.

Preparative Example 3-3

This example demonstrates the synthesis of (1S,3aR,4S,5R,7R)-7-cyclopropyl-1,4-dimethyl-1-((triethylsilyloxy)-1,2,3,3a,4,5,6,7-octahydro-4,7-epoxyazulen-5-ol (7a3) in an embodiment of the invention. See FIG. 3.

Compound 7a3 was synthesized as a colorless oil in 19% yield (72 mg) following the general procedure B from (8S,E)-1-cyclopropyl-3-hydroxyl-4,8-dimethyl-8-((triethylsilyl)oxy)dec-4-en-9-yn-1-one, 6a3 (374 mg, 1.02 mmol).

$^{1}$H-NMR (500 MHz, CDCl$_3$) δ 5.33 (d, J=2.8 Hz, 1H), 4.12 (dt, J=10.7, 5.0 Hz, 1H), 2.77 (td, J=8.9, 2.8 Hz, 1H), 2.39 (dd, J=11.9, 7.4 Hz, 1H), 1.77-1.68 (m, 3H), 1.51 (dd, J=11.9, 5.9 Hz, 1H), 1.44-1.39 (m, 1H), 1.36-1.34 (m, 1H), 1.31 (s, 3H), 1.29 (s, 3H), 1.14-1.08 (m, 1H), 0.94 (t, J=7.9 Hz, 9H), 0.59-0.55 (m, 6H), 0.52-0.49 (m, 2H), 0.47-0.43 (m, 1H), 0.37-0.33 (m, 1H). $^{13}$C-NMR (126 MHz, CDCl$_3$) δ 148.6, 118.8, 85.0, 80.9, 79.4, 73.9, 51.3, 47.4, 40.9, 28.5, 22.7, 20.2, 15.9, 7.2, 6.8, 1.3, 0.7. HRMS-ESI calculated for C$_{21}$H$_{36}$O$_3$SiNa (M+Na)$^+$: 387.2326; found: 387.2325.

Preparative Example 3-4

This example demonstrates the synthesis of (1S,3aR,4S,5R,7R)-1, (1S,3aR,4S,5R,7R)-7-cyclohexyl-1,4-dimethyl-1-((triethylsilyl)oxy)-1,2,3,3a,4,5,6,7-epoxyazulen-5-ol (7a4) in an embodiment of the invention. See FIG. 3.

Compound 7a4 was obtained as a colorless oil (127.6 mg, 32% yield) following general procedure B from (8S,E)-1-cyclohexyl-3-hydroxy-4,8-dimethyl-8-(triethylsilyloxy)-4-en-9-yn-1-one (6a4) (400 mg, 0.98 mmol).

$^{1}$H-NMR (500 MHz, CDCl$_3$) δ 5.60 (d, J=2.5 Hz, 1H), 4.13 (t, J=6.5 Hz, 1H), 2.77-2.73 (m, 1H), 2.46 (dd, J=12.0, 7.5 Hz, 1H), 1.89-1.86 (m, 1H), 1.80-1.60 (m, 9H), 1.59-1.55 (m, 1H), 1.53 (dd, J=12.0, 6.0 Hz, 1H), 1.31 (s, 3H), 1.30 (s, 3H), 1.29-1.24 (m, 2H), 1.20-1.10 (m, 2H), 0.97 (t, J=8.0 Hz, 9H), 0.62-0.57 (m, 6H). $^{13}$C-NMR (126 MHz, CDCl$_3$) δ 147.4, 118.9, 84.5, 83.0, 79.2, 73.7, 50.5, 47.5, 44.3, 40.7, 28.4, 27.7, 27.6, 26.50, 26.48, 26.1, 22.6, 20.2, 7.1, 6.7. HRMS-ESI calculated for C$_{24}$H$_{42}$O$_3$SiNa (M+Na)$^+$: 429.2795; found: 429.2796.

Preparative Example 3-5

This example demonstrates the synthesis of 4-dimethyl-7-phenyl-1-((triethylsilyl)oxy)-1,2,3,3a,4,5,6,7-octahydro-4,7-epoxyazulen-5-ol (7a5) in an embodiment of the invention. See FIG. 3.

Following the general procedure B, [IPrAuNCPh][SbF$_6$] (23.8 mg, 0.03 mmol) was added to a solution of (10S,E)-5-Hydroxy-2,2,6,10-tetramethyl-10-(triethylsilyloxy)dodec-6-en-11-yn-3-one (6a5) (206.1 mg, 0.51 mmol) in dichloromethane (7.2 mL). The product was obtained as a colorless oil (49.4 mg, 24% yield) after chromatographic purification (cyclohexane:EtOAc mixtures 9:1 to 1:1).

$^{1}$H-NMR (500 MHz, CDCl$_3$) δ 7.52-7.30 (m, 5H), 5.81 (d, J=2.7 Hz, 1H), 4.31 (t, J=6.6 Hz, 1H), 2.99-2.88 (m, 1H), 1.95-1.85 (m, 1H), 1.80-1.75 (m, 2H), 1.70-1.50 (m, 3H), 1.28 (s, 3H), 1.28 (s, 3H), 1.00-0.90 (m, 9H), 0.64-0.56 (m, 6H). $^{13}$C-NMR (126 MHz, CDCl$_3$) δ 147.4, 142.0, 128.3, 127.3, 125.4, 121.5, 85.3, 81.2, 79.3, 74.0, 53.7, 47.0, 40.7, 26.9, 22.6, 20.1, 7.0, 6.4. HRMS-ESI calculated for C$_{24}$H$_{36}$O$_3$SiNa (M+Na)$^+$: 423.2326; found: 423.2324.

Preparative Example 4

Step j)

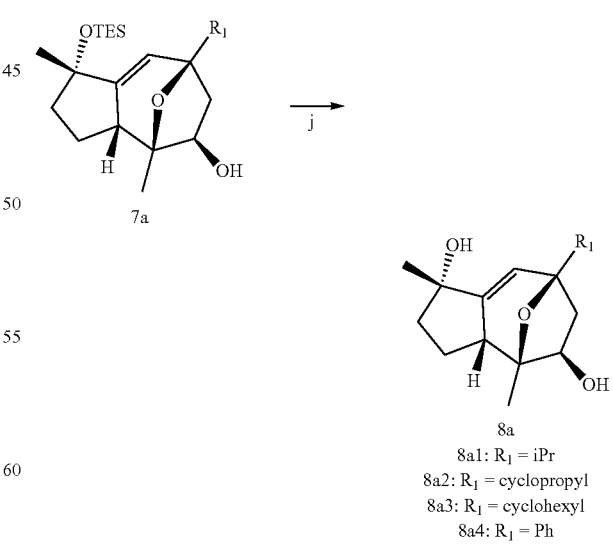

8a1: R$_1$ = iPr
8a2: R$_1$ = cyclopropyl
8a3: R$_1$ = cyclohexyl
8a4: R$_1$ = Ph General procedure C (triethyl silyl ether deprotection): the corresponding 1-triethylsilyloxy tricyclic compound 7a (1 equiv) was dissolved in dry THF (0.1 M) under argon atmosphere and the solution was cooled to 0° C. in an ice bath, then TBAF solution was added dropwise (1.2 equiv, 1 M in THF). After the addition reaction was left stirring at 23° C. for 12 h before being quenched with a saturated NH₄Cl solution. EtOAc was added and the layers separated, then the aqueous layer further extracted with EtOAc twice. The combined organic layers were dried with anhydrous Na₂SO₄, filtered and concentrated under vacuum. The crude was purified by silica flash chromatography using a mixture of cyclohexane:EtOAc 1:1 as eluent.

Preparative Example 4-1

This example demonstrates the synthesis of (1S,3aR,4S,5R,7R)-7-isopropyl-1,4-dimethyl-1,2,3,3a,4,5,6,7-octahydro-4,7-epoxyazulene-1,5-diol (8a1) in an embodiment of the invention. See FIG. 3.

General procedure C afforded compound 8a1 from the corresponding TES protected starting material 7a1 as previously described in Molawi et al., Angew. Chem. Int. Ed. 2010, 122, 3595-3597.

Preparative Example 4-2

This example demonstrates the synthesis of (1S,3aR,4S,5R,7R)-7-cyclopropyl-1,4-dimethyl-1,2,3,3a,4,5,6,7-octahydro-4,7-epoxyazulene-1,5-diol (8a2) in an embodiment of the invention. See FIG. 3.

General procedure C afforded compound 8a2 as a yellowish gum in 82% yield (93 mg) from the corresponding TES protected starting material 7a3 (165 mg, 0.45 mmol).

$^1$H-NMR (500 MHz, CDCl₃) δ 5.48 (d, J=2.8 Hz, 1H), 4.16 (dd, J=7.5, 5.9 Hz, 1H), 2.81-2.77 (m, 1H), 2.39 (dd, J=7.5, 5.9 Hz, 1H), 1.81-1.70 (m, 4H), 1.56-1.47 (m, 1H), 1.46-1.40 (m, 1H), 1.35 (s, 3H), 1.33 (s, 3H), 0.53-0.51 (m, 2H), 0.50-0.47 (m, 1H), 0.36-0.32 (m, 1H). $^{13}$C-NMR (126 MHz, CDCl₃) δ 149.2, 120.4, 84.8, 80.6, 77.5, 73.4, 51.0, 50.0, 41.1, 28.0, 23.6, 20.3, 15.8, 1.3, 0.8. HRMS-ESI calculated for C₁₅H₂₂O₃Na (M+Na)⁺: 273.1461; found: 273.1471.

Preparative Example 4-3

This example demonstrates the synthesis of (1S,3aR,4S,5R,7R)-7-(cyclohexyl)-1,4-dimethyl-1,2,3,3a,4,5,6,7-octahydro-4,7-epoxyazulene-1,5-diol (8a3) in an embodiment of the invention. See FIG. 3.

Compound 8a3 was obtained from 7a4 (187 mg, 0.48 mmol) following the general procedure C for the deprotection of the triethylsilyl group. The desired product was obtained as a white solid after purification by silica chromatography (81 mg, 58%).

M.p.: 63-65° C. $^1$H-NMR (400 MHz, CDCl₃) δ 5.72 (d, J=2.4 Hz, 1H), 4.15 (t, J=6.0 Hz, 1H), 2.80-2.73 (m, 1H), 2.49-2.43 (m, 1H), 1.89-1.85 (m, 2H), 1.76-1.72 (m, 9H), 1.59-1.43 (m, 2H), 1.36 (s, 3H), 1.32 (s, 3H), 1.30-1.17 (m, 4H), 1.10-1.02 (m, 1H). $^{13}$C-NMR (101 MHz, CDCl₃) δ 148.5, 120.4, 84.5, 83.0, 77.5, 73.4, 50.7, 50.3, 44.4, 41.1, 28.0, 27.9, 27.8, 26.6, 26.5, 26.2, 23.6, 20.4. HRMS-ESI calculated for C₁₈H₂₈O₃Na (M+Na)⁺: 318.1931; found: 315.1932.

Preparative Example 4-4

This example demonstrates the synthesis of (1S,3aR,4S,5R,7R)-1,4-dimethyl-7-phenyl-1,2,3,3a,4,5,6,7-octahydro-4,7-epoxyazulene-1,5-diol (8a4) in an embodiment of the invention. See FIG. 3.

Compound 8a4 was obtained as a colorless oil (35 mg, 30%) according to general procedure C from tricycle 7a5 (160 mg, 0.40 mmol).

$^1$H-NMR (500 MHz, CDCl₃) δ 7.49-7.46 (m, 2H), 7.37-7.34 (m, 2H), 7.29-7.26 (m, 1H), 5.89 (d, J=2.7 Hz, 1H), 4.31 (dd, J=7.4, 6.0 Hz, 1H), 2.95-2.89 (m, 2H), 1.94 (ddd, J=12.0, 7.0, 6.0 Hz, 1H), 1.86-1.75 (m, 3H), 1.54-1.48 (m, 1H), 1.42 (s, 3H), 1.35 (s, 3H). $^{13}$C-NMR (126 MHz, CDCl₃) δ 148.1, 141.9, 128.6, 127.6, 125.4, 123.2, 85.3, 81.2, 77.6, 73.8, 53.9, 49.9, 41.0, 28.0, 23.7, 20.4. HRMS-ESI calculated for C₁₈H₂₂O₃Na (M+Na)⁺: 309.1461; found: 309.1455.

Preparative Example 5

Step k)

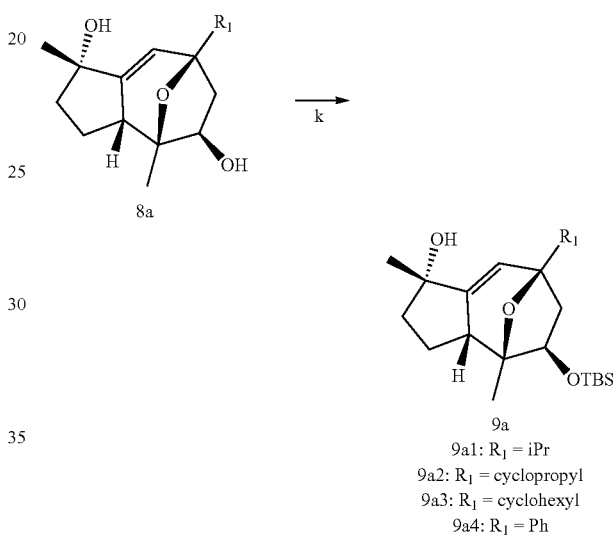

9a
9a1: R₁ = iPr
9a2: R₁ = cyclopropyl
9a3: R₁ = cyclohexyl
9a4: R₁ = Ph

General procedure D (alcohol protection with tert-butyldimethylsilyl): the corresponding tricyclic diol 8a (1 equiv) was dissolved in dry CH₂Cl₂ (0.05 M), N,N-dimethylpyridin-4-amine (0.1 equiv) and 1H-imidazole (3 equiv) were added followed by tert-butylchlorodimethylsilane (1.3 equiv). The mixture was left stirring at 23° C. under N₂ atmosphere between 6 and 10 h until full conversion was observed by TLC. Then, the reaction was stopped by addition of HCl (1 M) solution followed by extractive work up with CH₂Cl₂. The combined organic layers were dried with anhydrous Na₂SO₄ and concentrated in vacuo. Purification of the crude by silica gel chromatography afforded the pure product.

Preparative Example 5-1

This example demonstrates the synthesis of (1S,3aR,4S,5R,7S)-5-((tert-butyldimethylsilyl)oxy)-7-isopropyl-1,4-dimethyl-1,2,3,3a,4,5,6,7-octahydro-4,7-epoxyazulen-1-ol (9a1) in an embodiment of the invention. See FIG. 3.

(1S,3aR,4S,5R,7R)-7-(isopropyl)-1,4-dimethyl-1,2,3,3a,4,5,6,7-octahydro-4,7-epoxyazulene-1,5-diol, 8a1 (35 mg, 0.12 mmol) was protected with TBSCl according to the general procedure D, the final product was obtained as a colorless oil after purification by silica gel as previously described in Molawi et al., Angew. Chem. Int. Ed. 2010, 122, 3595-3597.

Preparative Example 5-2

This example demonstrates the synthesis of (1S,3aR,4S,5R,7S)-5-((tert-butyldimethylsilyl)oxy)-7-cyclopropyl-1,4-dimethyl-1,2,3,3a,4,5,6,7-octahydro-4,7-epoxyazulen-1-ol (9a2) in an embodiment of the invention. See FIG. 3.

Compound 9a2 was prepared as colorless oil (92 mg, 69%) according to general procedure D from (1S,3aR,4S,5R,7R)-7-cyclopropyl-1,4-dimethyl-1,2,3,3a,4,5,6,7-octahydro-4,7-epoxyazulene-1,5-diol, 8a2 (92 mg, 0.38 mmol).

$^1$H-NMR (500 MHz, CDCl$_3$) δ 5.41 (d, J=2.8 Hz, 1H), 4.08 (dd, J=7.3, 5.7 Hz, 1H), 2.75 (td, J=8.3, 7.8, 3.7 Hz, 1H), 2.20 (dd, J=11.7, 7.3 Hz, 1H), 1.77-1.65 (m, 3H), 1.54 (dd, J=11.8, 5.8 Hz 1H), 1.35 (tdd, J=11.2, 8.2, 4.8 Hz, 1H), 1.30 (s, 3H), 1.24 (s, 3H), 1.09 (tt, J=8.4, 5.3 Hz, 1H), 0.84 (s, 9H), 0.49-0.45 (m, 2H), 0.44-0.40 (m, 1H), 0.32-0.26 (m, 1H), −0.02 (s, 3H), −0.03 (s, 3H). $^{13}$C-NMR (126 MHz, CDCl$_3$) δ 149.1, 120.1, 85.3, 80.6, 77.4, 73.2, 51.3, 50.0, 41.0, 28.1, 25.8, 23.5, 20.7, 18.1, 15.8, 1.2, 0.6, −4.4, −4.9. HRMS-ESI calculated for C$_{21}$H$_{36}$O$_3$SiNa (M+Na)$^+$: 387.2326; found: 387.2325.

Preparative Example 5-3

This example demonstrates the synthesis of (1S,3aR,4S,5R,7S)-5-((tert-butyldimethylsilyl)oxy)-7-cyclohexyl-1,4-dimethyl-1,2,3,3a,4,5,6,7-octahydro-4,7-epoxyazulen-1-ol (9a3) in an embodiment of the invention. See FIG. 3.

(1S,3aR,4S,5R,7R)-7-(Cyclohexyl)-1,4-dimethyl-1,2,3,3a,4,5,6,7-octahydro-4,7-epoxyazulene-1,5-diol, 8a3 (35 mg, 0.12 mmol) was protected with TBSCl according to the general procedure D, the final product was obtained as a colorless oil after purification by silica gel (41 mg, 84%, cyclohexane:EtOAc 8:2 to 1:1 mixtures).

$^1$H-NMR (400 MHz, CDCl$_3$) δ 5.72 (d, J=2.8 Hz, 1H), 4.13 (dd, J=7.2, 5.6 Hz, 1H), 2.80-2.75 (m, 1H), 2.33 (dd, J=12.0, 7.2 Hz, 1H), 1.78-1.73 (m, 1H), 1.70-1.60 (m, 8H), 1.59-1.53 (m, 2H), 1.37 (s, 3H), 1.27 (s, 3H), 1.20-1.15 (m, 3H), 1.02-0.90 (m, 2H), 0.88 (s, 9H), 0.03 (s, 3H), 0.02 (s, 3H). $^{13}$C-NMR (101 MHz, CDCl$_3$) δ 148.5, 120.2, 85.0, 83.0, 77.5, 73.3, 51.2, 50.3, 44.6, 41.2, 28.1, 27.9, 27.8, 26.6, 26.2, 25.9, 23.6, 20.9, 18.2, −4.4, −4.8. HRMS-ESI calculated for C$_{24}$H$_{42}$O$_3$SiNa (M+Na)$^+$: 429.2795; found: 429.2803.

Preparative Example 5-4

This example demonstrates the synthesis of (1S,3aR,4S,5R,7S)-5-((tert-butyldimethylsilyl)oxy)-1,4-dimethyl-7-phenyl-1,2,3,3a,4,5,6,7-octahydro-4,7-epoxyazulen-1-ol (9a4) in an embodiment of the invention. See FIG. 3.

(1S,3aR,4S,5R,7R)-1,4-dimethyl-7-phenyl-1,2,3,3a,4,5,6,7-octahydro-4,7-epoxyazulene-1,5-diol, 8a4 (35 mg, 0.12 mmol) was protected with TBS according to procedure D in order to prepare 9a4 as a colorless oil in 67% yield (33 mg) after chromatographic purification (cyclohexane:EtOAc, 8:2) of the crude material.

$^1$H-NMR (500 MHz, CDCl$_3$) δ 7.52-7.50 (m, 2H), 7.40-7.36 (m, 2H), 7.31-7.28 (m, 1H), 5.92 (d, J=2.5 Hz, 1H), 4.32 (t, J=6.5 Hz, 1H), 2.95-2.90 (m, 1H), 2.80 (dd, J=11.5, 6.5 Hz, 1H), 1.99 (dd, J=11.5, 6.0 Hz, 1H), 1.86-1.78 (m, 3H), 1.52-1.50 (m, 1H), 1.39 (s, 3H), 1.38 (s, 3H), 0.91 (s, 9H), 0.08 (s, 3H), 0.06 (s, 3H). $^{13}$C-NMR (126 MHz, CDCl$_3$) δ 148.1, 142.3, 128.5, 127.4, 125.4, 123.2, 123.2, 85.8, 81.2, 77.6, 73.6, 54.3, 49.9, 41.1, 28.1, 27.1, 25.9, 23.7, 20.9, 18.2, −4.3, −4.8. HRMS-ESI calculated for C$_{24}$H$_{36}$O$_3$SiNa (M+Na)$^+$: 423.2326; found: 423.2323.

Preparative Example 6

Step 1)

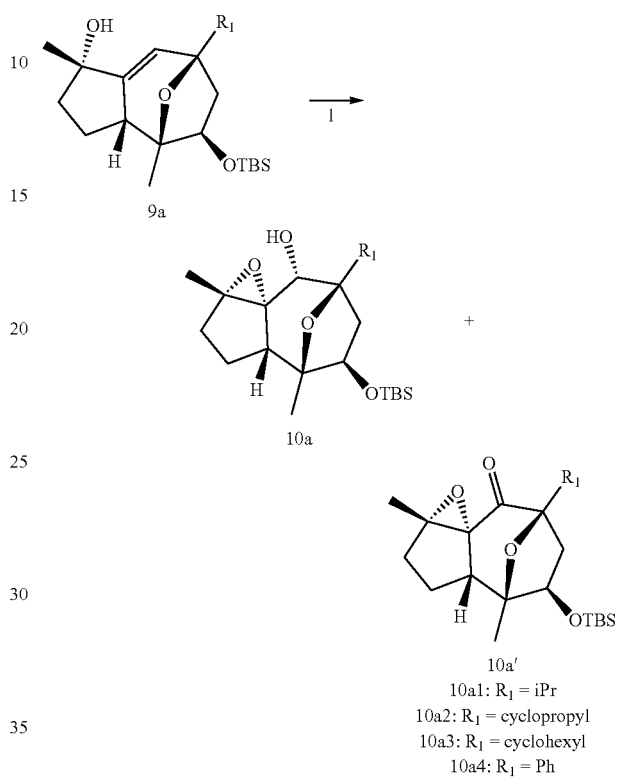

10a1: R$_1$ = iPr
10a2: R$_1$ = cyclopropyl
10a3: R$_1$ = cyclohexyl
10a4: R$_1$ = Ph General procedure E (oxidation with CrO$_3$): chromium (VI) oxide (6 equiv) was added to a solution of pyridine (12 equiv) in dry CH$_2$Cl$_2$ (0.05 M) at 0° C. and then warmed to room temperature while it turned a deep red solution. Then a solution of the corresponding alcohol compound 9a (1 equiv) in CH$_2$Cl$_2$ was added at once and the reaction was left stirring for 1 h at 23° C. After this time the crude was diluted with Et$_2$O and filtered through a pad of silica and evaporated to dryness. The crude was purified through silica column, eluting with cyclohexane:EtOAc from 98:2 to 95:5. Two fractions were obtained corresponding to the ketone 10a' and the desired epoxyalcohol 10a. The ketone 10a' was dissolved in MeOH (0.1 M), CeCl$_3$.(H$_2$O)$_7$ (0.1 equiv) was added followed by NaBH$_4$ (3 equiv). The reaction was vigorously stirred for 5 min before being quenched by with water. After extractive work up with EtOAc and purification by flash chromatography on silica (cyclohexane:EtOAc, 95:5) the desired epoxyalcohol was obtained and combined with the previous obtained fraction.

Preparative Example 6-1

This example demonstrates the synthesis of (1aS,3aS,4S,5R,7R,8R,8aS)-5-((tert-butyldimethylsilyl)oxy)-7-isopropyl-1a,4-dimethyloctahydro-3H-4,7-epoxyazuleno[1,8a-b]oxiren-8-ol (10a1) in an embodiment of the invention. See FIG. 3.

Compound 10a1 was obtained as a white solid following the general procedure E from (1S,3aR,4S,5R,7S)-5-((tert-butyldimethylsilyl)oxy)-7-cyclopropyl-1,4-dimethyl-1,2,3,3a,4,5,6,7-octahydro-4,7-epoxyazulen-1-ol, 10a1 as previously described in Molawi et al., *Angew. Chem. Int. Ed.* 2010, 122, 3595-3597.

Preparative Example 6-2

This example demonstrates the synthesis of (1aS,3aS,4S,5R,7R,8R,8aS)-5-((tert-butyldimethylsilyl)oxy)-7-cyclopropyl-1a,4-dimethyloctahydro-3H-4,7-epoxyazuleno[1,8a-b]oxiren-8-ol (10a2) in an embodiment of the invention. See FIG. 3.

Compound 10a2 was obtained as a white solid (43%, 40 mg) following the general procedure E from (1S,3aR,4S,5R,7S)-5-((tert-butyldimethylsilyl)oxy)-7-cyclopropyl-1,4-dimethyl-1,2,3,3a,4,5,6,7-octahydro-4,7-epoxyazulen-1-ol, 9a2 (90 mg, 0.25 mmol).

M.p.: 111-112° C. $^1$H-NMR (500 MHz, CDCl$_3$) δ 4.27 (dd, J=7.3, 2.8 Hz, 1H), 3.83 (dd, J=9.5, 1.4 Hz, 1H), 2.53 (dd, J=13.7, 7.3 Hz, 1H), 2.28 (d, J=9.8 Hz, 1H), 1.92-1.89 (m, 2H), 1.56-1.52 (m, 1H), 1.51 (s, 3H), 1.50-1.42 (m, 1H), 1.39-1.34 (m, 1H), 1.33-1.29 (m, 1H), 1.12 (s, 3H), 1.07-1.02 (m, 1H), 0.88 (s, 9H), 0.57-0.53 (m, 1H), 0.50-0.46 (m, 1H), 0.45-0.41 (m, 1H), 0.03 (s, 3H), 0.01 (s, 3H). $^{13}$C-NMR (126 MHz, CDCl$_3$) δ 85.7, 83.4, 72.6, 70.9, 69.9, 65.5, 49.4, 42.1, 32.8, 26.0, 25.9, 20.3, 19.4, 18.2, 15.7, 1.2, 1.1, −4.5, −4.9. HRMS-ESI calculated for C$_{21}$H$_{36}$O$_4$SiNa (M+Na)$^+$: 403.2275; found: 403.2279.

Preparative Example 6-3

This example demonstrates the synthesis of (1aS,3aS,4S,5R,7R,8R,8aS)-5-((tert-butyldimethylsilyl)oxy)-7-cyclohexyl-1a,4-dimethyloctahydro-3H-4,7-epoxyazuleno[1,8a-b]oxiren-8-ol (10a3) in an embodiment of the invention. See FIG. 3.

Compound 10a3 was synthesized following the general procedure E from (1S,3aR,4S,5R,7S)-5-((tert-butyldimethylsilyl)oxy)-7-cyclohexyl-1,4-dimethyl-1,2,3,3a,4,5,6,7-octahydro-4,7-epoxyazulen-1-ol, 9a3 (70 mg, 0.17 mmol). After separation and reduction of the ketone the combined fractions of the epoxyalcohol were purified by silica chromatography (cyclohexane:EtOAc, 95:5) to afford the final epoxyalcohol as a viscous colorless oil (45 mg, 62%).

$^1$H-NMR (400 MHz, CDCl$_3$) δ 4.30 (dd, J=7.3, 2.6 Hz, 1H), 4.08 (dd, J=10.2, 1.4 Hz, 1H), 2.54 (dd, J=13.9, 7.3 Hz, 1H), 2.21 (d, J=10.2 Hz, 1H), 1.96-1.92 (m, 1H), 1.91-1.83 (m, 3H), 1.79-1.76 (m, 3H), 1.63-1.57 (m, 2H), 1.52 (s, 3H), 1.47-1.39 (m, 2H), 1.28-1.18 (m, 5H), 1.15 (s, 3H), 1.06-1.00 (m, 1H), 0.88 (s, 9H), 0.04 (s, 3H), 0.02 (s, 3H). $^{13}$C-NMR (101 MHz, CDCl$_3$) δ 86.3, 85.9, 72.7, 71.2, 66.6, 65.4, 49.4, 44.2, 41.8, 32.9, 28.4, 27.4, 27.4, 26.9, 26.7, 26.0, 20.3, 19.5, 18.3, 15.2, −4.5, −4.8. HRMS-ESI calculated for C$_{24}$H$_{42}$O$_4$SiNa (M+Na)$^+$: 445.2745; found: 445.2737.

Preparative Example 6-4

This example demonstrates the synthesis of (1aS,3aS,4S,5R,7R,8R,8aS)-5-((tert-butyldimethylsilyl)oxy)-1a,4-dimethyl-7-phenyloctahydro-1aH-4,7-epoxyazuleno[1,8a-b]oxiren-8-ol (10a4) in an embodiment of the invention. See FIG. 3.

The desired product was obtained as a colorless oil in 70% yield (22 mg) following the general procedure E from (1S,3aR,4S,5R,7S)-5-((tert-butyldimethylsilyl)oxy)-1,4-dimethyl-7-phenyl-1,2,3,3a,4,5,6,7-octahydro-4,7-epoxyazulen-1-ol, 9a4 (30 mg, 0.08 mmol).

$^1$H-NMR (500 MHz, CDCl$_3$) δ 7.52-7.49 (m, 2H), 7.38-7.26 (m, 3H), 3.90 (dd, J=9.2, 1.6 Hz, 1H), 3.15 (dd, J=13.6, 7.6, 1H), 2.36 (d, J=8.8 Hz, 1H), 2.15-2.10 (m, 1H), 2.01-1.94 (m, 2H), 1.60-1.56 (m, 2H), 1.53 (s, 3H), 1.30 (s, 3H), 0.89 (s, 9H), 0.08 (s, 3H), 0.07 (s, 3H). $^{13}$C-NMR (126 MHz, CDCl$_3$) δ 143.3, 128.1, 127.3, 126.5, 86.4, 85.7, 72.8, 70.7, 65.7, 49.3, 44.3, 32.8, 26.0, 20.4, 18.3, 15.1, −4.5, −4.8. HRMS-ESI calculated for C$_{24}$H$_{36}$O$_4$SiNa (M+Na)$^+$: 439.2275; found: 439.2268.

Preparative Example 7

Step m)

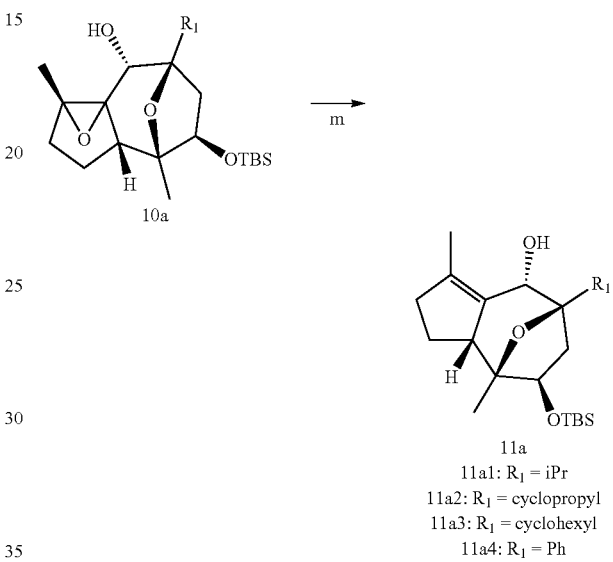

11a
11a1: R$_1$ = iPr
11a2: R$_1$ = cyclopropyl
11a3: R$_1$ = cyclohexyl
11a4: R$_1$ = Ph General procedure F (epoxide deoxygenation): nBuLi (4 equiv, 1.2 M in hexanes) was added dropwise to a solution of WCl$_6$ (2 equiv) in dry THF at −78° C. The solution was left to slowly reach room temperature for 1 h, then left 10 extra min stirring at room temperature before being cooled down again at 0° C. A solution of the epoxyalcohol 10a in THF (0.1 M final concentration) was then slowly added and the reaction was allowed to reach room temperature (23° C.) and then heated at 50° C. between 2-4 h until full conversion was achieved. The reaction was poured into a Rochelle salt:NaOH solution (1.5M:2M, 200 mL×mmol of substrate) and vigorously stirred for 10 min. Then Et$_2$O was added and the layers separated. The aqueous layer was further extracted with Et$_2$O twice, the combined organic layers washed with brine solution, dried over Na$_2$SO$_4$, filtered and concentrated under vacuum. The crude was purified by silica chromatography to provide the pure products.

Preparative Example 7-1

This example demonstrates the synthesis of (3aR,4S,5R,7R,8S)-5-((tert-butyldimethylsilyl)oxy)-7-cyclopropyl-1,4-dimethyl-2,3,3a,4,5,6,7,8-octahydro-4,7-epoxyazulen-8-ol (11a1) in an embodiment of the invention. See FIG. 3.

The named compound was synthesized following the general procedure F from 10a1 as previously described in Molawi et al., *Angew. Chem. Int. Ed.* 2010, 122, 3595-3597.

Preparative Example 7-2

This example demonstrates the synthesis of (3aR,4S,5R,7R,8S)-5-((tert-butyldimethylsilyl)oxy)-7-cyclopropyl-1,4-

39 dimethyl-2,3,3a,4,5,6,7,8-octahydro-4,7-epoxyazulen-8-ol (11a2) in an embodiment of the invention. See FIG. 3.

The named compound was synthesized following the general procedure F from 10a2 (40 mg, mmol). The desired allyl alcohol was obtained as the main component of a mixture of products, inseparable by flash chromatography, and used directly in the next reaction.

Preparative Example 7-3

This example demonstrates the synthesis of (3aR,4S,5R,7R,8S)-5-((tert-butyldimethylsilyl)oxy)-7-cyclohexyl-1,4-dimethyl-2,3,3a,4,5,6,7,8-octahydro-4,7-epoxyazulen-8-ol (11a3) in an embodiment of the invention. See FIG. 3.

Compound 11a3 was prepared following the general procedure F from (1aS,3aS,4S,5R,7R,8R,8aS)-5-((tert-butyldimethylsilyl)oxy)-7-cyclohexyl-1a,4-dimethyloctahydro-3H-4,7-epoxyazuleno[1,8a-b]oxiren-8-ol, 10a3 (45 mg, 0.11 mmol). After purification by silica flash chromatography (cyclohexane:EtOAc, 95:5) a pale yellow oil was obtained (32 mg, 74%).

$^1$H-NMR (400 MHz, CDCl$_3$) δ 4.41-4.38 (m, 1H), 3.89 (dd, J=7.4, 2.2 Hz, 1H), 2.71-2.62 (m, 1H), 2.38-2.17 (m, 2H), 2.13 (dd, J=13.6, 7.4 Hz, 1H), 1.88 (s, 3H), 1.84-1.76 (m, 4H), 1.67-1.64 (m, 1H), 1.60-1.53 (m, 2H), 1.43 (d, J=6.7 Hz, 1H), 1.35-1.17 (m, 7H), 1.11 (s, 3H), 0.89 (s, 9H), 0.04 (s, 3H), 0.02 (s, 3H). $^{13}$C-NMR (101 MHz, CDCl$_3$) δ 133.5, 132.8, 87.3, 85.7, 73.1, 73.0, 56.4, 42.3, 41.3, 39.1, 28.4, 27.4, 27.2, 26.7, 26.0, 26.0, 19.3, 18.3, 14.8, −4.4, −4.8. HRMS-ESI calculated for C$_{24}$H$_{42}$O$_3$SiNa (M+Na)$^+$: 429.2795; found: 429.2811.

Preparative Example 7-4

This example demonstrates the synthesis of (3aR,4S,5R,7R,8S)-5-((tert-butyldimethylsilyl)oxy)-1,4-dimethyl-7-phenyl-2,3,3a,4,5,6,7,8-octahydro-4,7-epoxyazulen-8-ol (11a4) in an embodiment of the invention. See FIG. 3.

Compound 11a4 was prepared according to general procedure F from 10a4 (22 mg, 0.05 mmol). The desired allyl alcohol was obtained as the main component of a mixture of products, inseparable by flash chromatography, and used directly in the next reaction.

Example 1

Step n)

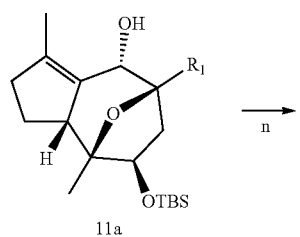

11a

40

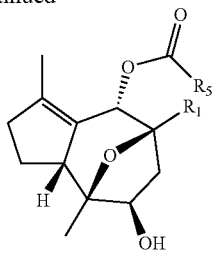

12a
(Ia): R$_1$ = iPr, R$_5$ = CHCHPh
(Ib): R$_1$ = iPr, R$_5$ = CH$_2$CH$_2$CH$_2$Ph
(Ic): R$_1$ = iPr, R$_5$ = 1,2-trans-phenylcyclopropyl
(Id): R$_1$ = iPr, R$_5$ = Me
(Ie): R$_1$ = cyclohexyl, R$_5$ = CHCHPh
(If): R$_1$ = cyclopropyl, R$_5$ = CHCHPh
(Ig): R$_1$ = Ph, R$_5$ = CHCHPh General procedure G (ester formation and tert-butyldimethylsilyl deprotection): a solution of the corresponding free alcohol, the compound of formula R$_5$COCl (3 equiv), DMAP (3 equiv) and NEt$_3$ (15 equiv) in dry CH$_2$Cl$_2$ (0.2 M) was stirred at reflux at 80° C. in a capped pressure tube for 4 h. After cooling to room temperature, the crude product was filtered through a pad of silica eluting with cyclohexane:EtOAc 9:1. After concentration, the obtained material was used directly in the deprotection of the tert-butyldimethylsilyl group. A TBAF solution (1.0 M in THF, 2 equiv) was added to a solution of the TBS-protected analogue in THF (0.1 M) at 0° C. Then, the reaction was allowed to stir at 23° C. for 10 h before being quenched with water. EtOAc was added to the mixture and the two layers separated, the aqueous layer was further extracted twice with EtOAc and then the combined organic layers were dried over Na$_2$SO$_4$, filtered and concentrated under vacuum. The crude was purified by silica chromatography.

Example 1-1

This example demonstrates the synthesis of (3aR,4S,5R,7R,8S)-5-hydroxy-7-isopropyl-1,4-dimethyl-2,3,3a,4,5,6,7,8-octahydro-4,7-epoxyazulen-8-yl cinnamate (Ia) in an embodiment of the invention.

According to general procedure G, a solution of 11a1 (37.7 mg, 0.10 mmol), cinnamoyl chloride (49.5 mg, 0.30 mmol) and DMAP (36.3 mg, 0.30 mmol) in dichloromethane (2 mL) and Et$_3$N (0.2 mL, 1.49 mmol) was stirred at 45° C. for 4 h. After this time, solvents were evaporated, and the crude was used directly in the TBS deprotection with TBAF solution (1.0 M in THF, 71 μL, 0.071 mmol). Chromatographic purification (hexane:EtOAc, 5:1) of the crude material yielded product (Ia) as a colorless oil (12.8 mg, 45% 2 steps).

[α]$_D^{25}$=0.8 (c=0.17, CHCl$_3$). $^1$H-NMR (400 MHz, CDCl$_3$) δ 7.75 (d, J=16.0 Hz, 1H), 7.59-7.56 (m, 2H), 7.44-7.28 (m, 3H), 6.50 (d, J=16.0 Hz, 1H), 5.65 (d, J=1.2 Hz, 1H), 4.03 (bs, 1H), 2.88-2.86 (m, 1H), 2.50 (dd, J=14.0, 7.2 Hz, 1H), 2.42-2.39 (m, 1H), 2.30-2.27 (m, 1H), 1.97-1.88 (m, 2H), 1.74-1.70 (m, 1H), 1.61 (s, 3H), 1.44-1.35 (m, 2H), 1.25 (s, 3H), 1.05 (d, J=6.8 Hz, 3H), 1.01 (d, J=7.2 Hz, 3H). $^{13}$C-NMR (100 MHz, CDCl$_3$) δ 166.4, 145.9, 134.3, 133.5, 130.7, 129.1, 128.8, 128.4, 117.9, 87.4, 85.4, 73.9, 73.7, 56.7, 42.4, 39.7, 31.8, 23.2, 18.8, 18.0, 17.4, 13.9. HRMS-ESI calculated for C$_{24}$H$_{30}$O$_4$Na (M+Na)$^+$: 405.2036; found: 405.2047.

Example 1-2

This example demonstrates the synthesis of (3aR,4S,5R,7R,8S)-5-hydroxy-7-isopropyl-1,4-dimethyl-2,3,3a,4,5,6,7,8-octahydro-4,7-epoxyazulen-8-yl 4-phenylbutanoate (Ib) in an embodiment of the invention.

Compound (Ib) was obtained from 11a1 (39 mg, 0.11 mmol) and 4-phenylbutanoic acid (18 mg, 0.12 mmol) (instead of protected glycolic acid) as follows: Et$_3$N (2.5 equiv) and 2,4,6-trichlorobenzoyl chloride (1.1 equiv) were added to a stirred solution containing 11a1, the corresponding acid (1.1 equiv) and DMAP (2.0 equiv) in toluene (0.03 M) at 0° C. The resulting white suspension was stirred at room temperature (23° C.) for 1 h before being quenched by adding a saturated aqueous NH$_4$Cl solution. Diethyl ether (Et$_2$O) was added, and the layers separated. The aqueous layer was further extracted twice with Et$_2$O. The combined organic layers were washed with brine, dried over Na$_2$SO$_4$, filtered, and concentrated in vacuo. The crude was purified by flash chromatography on silica. After deprotection of the TBS group with TBAF and purification by silica flash chromatography (cyclohexane:EtOAc, 9:1 to 7:3) a colorless oil was obtained in 27% yield (2 steps, 12 mg).

$[\alpha]_D^{25}$=29.7 (c=0.24, CHCl$_3$). $^1$H-NMR (300 MHz, CDCl$_3$) δ 7.32-7.25 (m, 2H), 7.23-7.14 (m, 3H), 5.53-5.50 (m, 1H), 3.95 (d, J=7.0 Hz, 1H), 2.86-2.76 (m, 1H), 2.68 (m, 2H), 2.42-2.39 (m, 4H), 2.29-2.17 (m, 1H), 1.97-1.88 (m, 2H), 1.91-1.77 (m, 1H), 1.67-1.60 (m, 1H), 1.58 (s, 3H), 1.47-1.39 (m, 1H), 1.37-1.30 (m, 1H), 1.21 (s, 3H), 1.00 (d, J=6.8 Hz, 3H), 0.96 (d, J=7.0 Hz, 3H). $^{13}$C-NMR (101 MHz, CDCl$_3$) δ 172.9, 141.4, 133.1, 129.9, 128.6, 126.2, 87.4, 85.2, 73.9, 73.7, 56.7, 42.2, 39.6, 35.3, 34.0, 31.3, 26.3, 23.2, 18.7, 17.8, 17.3, 13.8. HRMS-ESI calculated for C$_{25}$H$_{34}$O$_4$Na (M+Na)$^+$: 421.2349; found: 421.2354.

Example 1-3

This example demonstrates the synthesis of (3aR,4S,5R,7R,8S)-5-hydroxy-7-isopropyl-1,4-dimethyl-2,3,3a,4,5,6,7,8-octahydro-4,7-epoxyazulen-8-yl 2-phenylcyclopropane-1-carboxylate (Ic) in an embodiment of the invention.

Compound (Ic) was obtained quantitatively as a dense colorless oil from 11a1 (20 mg, 0.06 mmol) and trans-2-phenylcyclopropane1-carboxylic acid (7 mg, 0.06 mmol) according to the procedure described in Example 1-2, replacing butyric acid by trans-2-phenylcyclopropane1-carboxylic acid.

$[\alpha]_D^{25}$=27.6 (c=0.10, CHCl$_3$). $^1$H-NMR (500 MHz, CDCl$_3$) δ 7.31-7.27 (m, 2H), 7.24-7.19 (m, 1H), 7.11-7.08 (m, 2H), 5.53-5.50 (m, 1H), 3.96 (bs, 1H), 2.86-2.78 (m, 1H), 2.63-2.51 (m, 1H), 2.42-2.37 (m, 2H), 2.28-2.19 (m, 1H), 1.95-1.85 (m, 3H), 1.70-1.67 (m, 1H), 1.62-1.59 (m, 1H), 1.41-1.36 (m, 2H), 1.37-1.30 (m, 1H), 1.26 (s, 3H), 1.21 (s, 3H), 1.02 (dd, J=11.1, 6.8 Hz, 3H), 0.98 (dd, J=12.1, 7.0 Hz, 3H). $^{13}$C-NMR (76 MHz, CDCl$_3$) δ 172.9, 139.9 (one isomer), 139.8 (other isomer), 133.4 (one isomer), 133.4 (other isomer), 128.8, 128.7 (one isomer), 128.7 (other isomer), 126.8, 126.5 (one isomer), 126.4 (other isomer), 87.4 (one isomer), 87.4 (other isomer), 85.2 (one isomer), 85.2 (other isomer), 74.2, 73.6 (one isomer), 73.6 (other isomer), 56.7, 42.3 (one isomer), 42.2 (other isomer), 39.6, 31.8 (one isomer), 31.7 (other isomer), 29.8, 27.0 (one isomer), 26.3 (other isomer), 24.4 (one isomer), 24.3 (other isomer), 23.2 (one isomer), 23.2 (other isomer), 18.7, 17.9 (one isomer), 17.9 (others isomer), 17.4 (one isomer), 17.3 (other isomer), 17.1 (one isomer), 16.4 (other isomer), 13.9 (one isomer), 13.9 (other isomer). HRMS-ESI calculated for C$_{25}$H$_{32}$O$_4$Na (M+Na)$^+$: 419.2193; found: 421.2197.

Example 1-4

This example demonstrates the synthesis of (3aR,4S,5R,7R,8S)-5-hydroxy-7-isopropyl-1,4-dimethyl-2,3,3a,4,5,6,7,8-octahydro-4,7-epoxyazulen-8-yl acetate (Id) in an embodiment of the invention.

A solution of 11a1 (20 mg, 0.06 mmol), acetyl chloride (12 μL, 0.18 mmol), DMAP (22 mg, 0.18 mmol) and NEt$_3$ (125 μL, 0.90 mmol) in dry CH$_2$Cl$_2$ (0.5 mL) was stirred at 23° C. for 14 h. Then the crude was filtered through a pad of silica eluting with cyclohexane:EtOAc, 9:1. After evaporating the solvent, deprotection of TBS group was performed as described in general procedure B. A colorless oil was obtained after purification by silica chromatography (cyclohexane:EtOAc, 7:3) in 43% yield (2 steps, 5 mg).

$^1$H-NMR (300 MHz, CDCl$_3$) δ 5.49-5.47 (m, 1H), 3.97-3.94 (m, 1H), 2.91-2.71 (m, 1H), 2.37 (dd, J=14.3, 7.5 Hz, 2H), 2.30-2.18 (m, 1H), 2.11 (s, 3H), 1.96-1.77 (m, 2H), 1.66 (t, J=1.7 Hz, 1H), 1.61 (s, 3H), 1.39-1.29 (m, 2H), 1.20 (s, 3H), 1.01 (d, J=6.8 Hz, 3H), 0.96 (d, J=7.0 Hz, 3H). $^{13}$C-NMR (101 MHz, CDCl$_3$) δ 172.9, 141.4, 133.1, 129.9, 128.6, 126.2, 87.4, 85.2, 73.9, 73.7, 56.7, 42.2, 39.6, 35.3, 34.0, 31.3, 26.3, 23.2, 18.7, 17.8, 17.3, 13.8.

Example 1-5

This example demonstrates the synthesis of (3aR,4S,5R,7R,8S)-7-cyclohexyl-5-hydroxy-1,4-dimethyl-2,3,3a,4,5,6,7,8-octahydro-4,7-epoxyazulen-8-yl cinnamate (Ie) in an embodiment of the invention.

The cinnamate product was formed from (3aR,4S,5R,7R,8S)-5-((tert-butyldimethylsilyl)oxy)-7-cyclohexyl-1,4-dimethyl-2,3,3a,4,5,6,7,8-octahydro-4,7-epoxyazulen-8-ol, 11a3 (32 mg, 0.08 mmol) according to the general procedure G. After TBS deprotection and purification through flash chromatography on silica (cyclohexane:EtOAc, 8:2) a colorless dense oil was obtained (16 mg, 48% 2 steps).

$[\alpha]_D^{25}$=9.6 (c=0.15, CHCl$_3$). $^1$H-NMR (400 MHz, CDCl$_3$) δ 7.73 (d, J=16.0 Hz, 1H), 7.58-7.56 (m, 2H), 7.42-7.40 (m, 3H), 6.49 (d, J=16.0 Hz, 1H), 5.62-5.60 (m, 1H), 3.99 (bs, 1H), 2.88-2.80 (m, 1H), 2.45 (dd, J=14.3, 7.4 Hz, 1H), 2.41-2.36 (m, 1H), 2.27-2.21 (m, 1H), 1.99-1.85 (m, 2H), 1.79-1.71 (m, 4H), 1.59 (s, 3H), 1.56-1.45 (m, 6H), 1.39-1.33 (m, 2H), 1.22 (s, 3H), 1.13-1.09 (m, 1H). $^{13}$C-NMR (101 MHz, CDCl$_3$) δ 166.5, 145.9, 134.4, 133.5, 130.7, 129.1, 128.8, 128.4, 117.8, 87.4, 85.3, 73.6, 73.6, 56.7, 42.3, 42.2, 39.7, 28.1, 27.2, 27.1, 26.9, 26.6, 23.2, 18.8, 13.9. HRMS-ESI calculated for C$_{27}$H$_{34}$O$_4$Na (M+Na)$^+$: 445.2349; found: 445.2345.

Example 1-6

This example demonstrates the synthesis of (3aR,4S,5R,7R,8S)-5-hydroxy-1,4-dimethyl-7-phenyl-2,3,3a,4,5,6,7,8- octahydro-4,7-epoxyazulen-8-yl cinnamate (If) in an embodiment of the invention. See FIG. 3.

Ester formation from 11a4 (15 mg, 0.04 mmol) and cinnamoyl chloride (18.7 mg, 0.11 mmol) according to general procedure G and subsequent TBS deprotection afforded the desired product as a white solid after purification by silica chromatography (cyclohexane:EtOAc, 98:2, 9 mg, 58% 2 steps).

M.p.: 100-102° C. $[\alpha]_D^{25}$=13.8 (c=0.92, CHCl$_3$). $^1$H-NMR (400 MHz, CDCl$_3$) δ 7.53 (d, J=16.1 Hz, 1H), 7.51-7.49 (m, 2H), 7.42-7.38 (m, 5H), 7.28-7.24 (m, 2H), 7.22-7.18 (m, 1H), 6.30 (d, J=16.0 Hz, 1H), 5.58-5.45 (m, 1H), 4.16 (dd, J=7.6, 2.6 Hz, 1H), 3.09 (dd, J=13.9, 7.7 Hz, 1H), 3.06-3.01 (m, 1H), 2.42 (t, J=1.9 Hz, 1H), 2.37-2.28 (m, 1H), 2.05-1.94 (m, 1H), 1.66 (s, 3H), 1.53-1.45 (m, 1H), 1.33 (s, 3H). $^{13}$C-NMR (101 MHz, CDCl$_3$) δ 165.5, 145.4, 141.6, 134.4, 130.6, 129.0, 128.3, 128.0, 127.9, 127.6, 126.5, 117.6, 87.6, 84.7, 76.6, 73.4, 56.6, 45.0, 39.5, 23.3, 23.2, 18.9, 14.2. HRMS-ESI calculated for C$_{27}$H$_{28}$O$_4$Na (M+Na)$^+$: 439.1880; found: 439.1881.

Example 1-7

This example demonstrates the synthesis of (3aR,4S,5R,7R,8S)-7-cyclopropyl-5-hydroxy-1,4-dimethyl-2,3,3a,4,5,6,7,8-octahydro-4,7-epoxyazulen-8-yl cinnamate (Ig) in an embodiment of the invention. See FIG. 3.

Compound (Ig) was obtained as a white solid (15.3 mg, 40% yield after 3 steps) following the general procedure G from the impure (3aR,4S,5R,7R,8S)-5-((tert-butyldimethylsilyl)oxy)-7-cyclopropyl-1,4-dimethyl-2,3,3a,4,5,6,7,8-octahydro-4,7-epoxyazulen-8-ol, 11a2.

M.p. 42-43° C. $[\alpha]_D^{25}$=−7.3 (c=0.12, CHCl$_3$). $^1$H-NMR (400 MHz, CDCl$_3$) δ 7.74 (d, J=16.0 Hz, 1H), 7.56 (dd, J=6.6, 3.0 Hz, 2H), 7.46-7.32 (m, 3H), 6.50 (d, J=16.0 Hz, 1H), 5.61-5.59 (m, 1H), 4.01 (dd, J=7.5, 2.4 Hz, 1H), 2.86 (dd, J=8.5, 2.1 Hz, 1H), 2.37-2.33 (m, 1H), 2.29-2.22 (m, 1H), 1.92-1.89 (m, 1H), 1.65 (s, 3H), 1.39-1.33 (m, 1H), 1.21 (s, 3H), 1.11-1.07 (m, 1H), 0.55-0.48 (m, 1H), 0.45-0.38 (m, 2H), 0.38-0.31 (m, 1H). $^{13}$C-NMR (126 MHz, CDCl$_3$) δ 166.5, 145.7, 134.4, 133.9, 130.6, 129.1, 128.3, 117.9, 87.1, 82.9, 76.2, 73.1, 56.6, 41.4, 39.3, 23.4, 18.8, 14.7, 14.1, 1.6, 0.7. HRMS-ESI calculated for C$_{24}$H$_{28}$O$_4$Na (M+Na)$^+$: 403.1880; found: 403.1876.

Example 2

Step o)

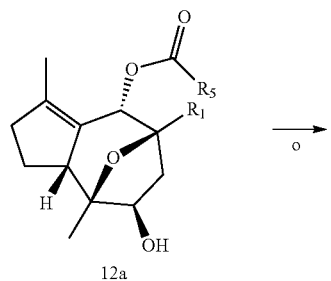

12a

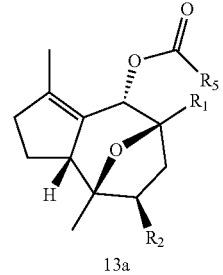

13a (Ih): R$_1$ = iPr, R$_5$ = CHCHPh, R$_2$ = OCOCH$_2$OH
(Ii): R$_1$ = iPr, R$_5$ = CH$_2$CH$_2$CH$_2$Ph, R$_2$ = OCOCH$_2$OH
(Ij): R$_1$ = iPr, R$_5$ = 1,2-trans-phenylcyclopropyl, R$_2$ = OCOCH$_2$OH
(Ik): R$_1$ = iPr, R$_5$ = Me, R$_2$ = OCOCH$_2$OH
(Il): R$_1$ = iPr, R$_5$ = CHCHPh, R$_2$ = OCOCH(CH$_3$)OH
(Im): R$_1$ = iPr, R$_5$ = CHCHPh, R$_2$ = OCOCH$_3$
(In): R$_1$ = iPr, R$_5$ = CHCHPh, R$_2$ = OCOCH(CH$_3$)NHBoc
(Io): R$_1$ = iPr, R$_5$ = CHCHPh, R$_2$ = OCOCH$_2$NH$_2$
(Ip): R$_1$ = iPr, R$_5$ = CHCHPh, R$_2$ = OCOCH(CH$_3$)NH$_2$
(Iq): R$_1$ =cyclohexyl, R$_5$ = CHCHPh, R$_2$ = OCOCH$_2$OH
(Ir): R$_1$ =cyclopropyl, R$_5$ = CHCHPh, R$_2$ = OCOCH$_2$OH
(Is): R$_1$ =Ph, R$_5$ = CHCHPh, R$_2$ = OCOCH$_2$OH General procedure H(Yamaguchi esterification): Et$_3$N (2.5 equiv) and 2,4,6-trichlorobenzoyl chloride (1.1 equiv) were added to a stirred solution containing the tricyclic alcohol free product of formula 12a, the corresponding acid of formula R$_2$CO$_2$H (1.1 equiv) and DMAP (2.0 equiv) in toluene (0.03 M) at 0° C. The resulting white suspension was stirred at r.t. (2° C.) for 1 h before being quenched adding saturated aqueous NH$_4$Cl solution. Et$_2$O was added and the layers separated. The aqueous layer was further extracted twice with Et$_2$O. The combined organic layers were washed with brine, dried over Na$_2$SO$_4$, filtered and concentrated in vacuo. The crude was purified by flash chromatography on silica.

In the cases when the acid used contained a TBDPS protected alcohol (TBDPS-protected glycolic acid, TBDPS-protected lactic acid) the final product was obtained by deprotection of the crude with TBAF as follows: acetic acid (20 equiv) and TBAF solution (1M in THF, 2 equiv) were added to a stirred solution of the TBDPS-protected analogue in THF (0.1 M) at 0° C. After stirring for 4 h at r.t., the reaction was quenched with saturated aqueous NH$_4$Cl solution, extractive work up with EtOAc followed. The combined organic layers were dried over Na$_2$SO$_4$, filtered, and concentrated under vacuum. The final compounds were obtained after chromatographic purification on silica.

Example 2-1

Compound (Ih) was prepared following the general procedure H starting from the compound of formula (Ia) and using 2-((tert-butyldiphenylsilyl)oxy)acetic acid as a compound of formula R$_2$CO$_2$H.

$[\alpha]_D^{25}$=−40.3 (c=0.19, CHCl$_3$). $^1$H-NMR (500 MHz, CDCl$_3$) δ 7.75 (d, J=16.0 Hz, 1H), 7.59-7.57 (m, 2H), 7.43-7.42 (m, 3H), 6.50 (d, J=16.0 Hz, 1H), 5.69 (bs, 1H), 5.24 (dd, J=8.0, 2.5 Hz, 1H), 4.21 (s, 2H), 2.92-2.87 (m, 1H), 2.56 (dd, J=14.5, 8.0 Hz, 1H), 2.43-2.32 (m, 2H), 1.98-1.89 (m, 2H), 1.81 (d, J=14.0 Hz, 1H), 1.64 (s, 3H), 1.60-1.50 (m, 1H), 1.28-1.26 (m, 1H), 1.18 (s, 3H), 1.03 (d, J=7.0 Hz, 3H), 1.00 (d, J=7.0 Hz, 3H). $^{13}$C-NMR (125 MHz, CDCl$_3$) δ 173.2, 166.3, 146.1, 134.6, 134.3, 130.8, 129.1, 128.4, 128.0, 117.8, 86.7, 85.9, 73.3, 60.8, 56.9, 39.7, 39.4, 32.1, 27.0, 22.9, 18.5, 18.1, 17.3, 13.9. HRMS-ESI calculated for $C_{26}H_{32}O_6Na$ (M+Na)$^+$: 463.2091; found: 463.2087.

Example 2-2

This example demonstrates the synthesis of (3aR,4S,5R,7R,8S)-5-(2-hydroxyacetoxy)-7-isopropyl-1,4-dimethyl-2,3,3a,4,5,6,7,8-octahydro-4,7-epoxyazulen-8-yl 4-phenylbutanoate (Ii) in an embodiment of the invention. See FIG. 3.

Compound (Ii) was synthesized following general procedure H from (Ib) (14 mg, 0.035 mmol) and 2-((tert-butyldiphenylsilyl)oxy)acetic acid (12.4 mg, 0.04 mmol). After purification by flash chromatography (cyclohexane:EtOAc, 8:2 to 1:1) a colorless oil was obtained in 81% yield (13 mg, 0.028 mmol).

$[\alpha]_D^{25}$=1.3 (c=0.14, CHCl$_3$). $^1$H-NMR (400 MHz, CDCl$_3$) δ 7.31-7.27 (m, 2H), 7.24-7.17 (m, 3H), 5.54-5.53 (m, 1H), 5.16 (dd, J=8.0, 2.5 Hz, 1H), 4.16 (d, J=3.6 Hz, 2H), 2.84-2.79 (m, 1H), 2.67 (t, J=7.7 Hz, 2H), 2.44-2.30 (m, 6H), 2.02-1.95 (m, 2H), 1.94-1.88 (m, 1H), 1.83 (sept, J=6.8 Hz, 1H), 1.73 (ddd, J=14.5, 2.5, 1.4 Hz, 1H), 1.60 (s, 3H), 1.52-1.46 (m, 1H), 1.13 (s, 3H), 0.98 (d, J=6.8 Hz, 3H), 0.95 (d, J=6.9 Hz, 3H). $^{13}$C-NMR (101 MHz, CDCl$_3$) δ 173.1, 172.8, 141.3, 134.2, 128.6, 128.5, 128.1, 126.2, 86.7, 85.7, 77.2, 73.4, 60.7, 56.9, 39.7, 35.3, 34.0, 31.5, 26.3, 22.8, 18.4, 17.9, 17.2, 13.9. HRMS-ESI calculated for $C_{27}H_{36}O_6Na$ (M+Na)$^+$: 479.2404; found: 479.2406.

Example 2-3

This example demonstrates the synthesis of (3aR,4S,5R,7R,8S)-5-(2-hydroxyacetoxy)-7-isopropyl-1,4-dimethyl-2,3,3a,4,5,6,7,8-octahydro-4,7-epoxyazulen-8-yl-2-phenylcyclopropane-1-carboxylate (Ij) in an embodiment of the invention. See FIG. 3.

Compound (Ij) was produced as a colorless oil in 80% (4.6 mg) according to general procedure H from (Ic) (5 mg, 0.013 mmol) and 2-((tert-butyldiphenylsilyl)oxy)acetic acid (6 mg, 0.02 mmol), after alcohol deprotection and purification by flash chromatography (cyclohexane:EtOAc, 8:2 to 1:1).

$[\alpha]_D^{25}$=−7.3 (c=0.11, CHCl$_3$). $^1$H-NMR (500 MHz, CDCl$_3$) δ 7.31-7.27 (m, 2H), 7.24-7.20 (m, 1H), 7.11-7.08 (m, 2H), 5.58-5.55 (m, 1H), 5.18 (td, J=7.8, 2.5 Hz, 1H), 4.17 (s, 2H), 2.85-2.81 (m, 1H), 2.63-2.52 (m, 1H), 2.47-2.38 (m, 2H), 2.38-2.33 (m, 1H), 1.95-1.83 (m, 3H), 1.76-1.71 (m, 1H), 1.69-1.66 (m, 2H), 1.64-1.59 (m, 1H), 1.53-1.47 (m, 1H), 1.42-1.37 (m, 1H), 1.25 (s, 3H), 1.13 (s, 3H), 0.98 (ddd, J=14.8, 12.1, 6.9 Hz, 6H). $^{13}$C-NMR (126 MHz, CDCl$_3$) δ 173.2 (one isomer), 173.1 (other isomer), 172.9 (one isomer), 172.9 (other isomer), 139.9 (one isomer), 139.8 (other isomer), 134.5 (one isomer), 134.5 (other isomer), 128.7, 128.0 (one isomer), 128.0 (other isomer), 126.8 (one isomer), 126.8 (other isomer), 126.5 (one isomer), 126.4 (other isomer), 86.8 (one isomer), 86.7 (other isomer), 85.8 (one isomer), 85.7 (other isomer), 77.2, 73.7 (one isomer), 73.7 (other isomer), 60.8, 56.9, 39.7, 39.3 (one isomer), 39.2 (other isomer), 32.1 (one isomer), 31.9 (other isomer), 29.9 (one isomer), 29.8 (other isomer), 27.1, 26.4, 24.4 (one isomer), 24.3 (other isomer), 22.9 (one isomer), 22.9 (other isomer), 18.5, 18.1, 18.0 (other isomer), 17.3 (one isomer), 17.3 (other isomer), 17.1, 16.4, 13.9. HRMS-ESI calculated for $C_{27}H_{34}O_6Na$ (M+Na)$^+$: 477.2248; found: 477.2245.

Example 2-4

This example demonstrates the synthesis of (3aR,4S,5R,7R,8S)-8-acetoxy-7-isopropyl-1,4-dimethyl-2,3,3a,4,5,6,7,8-octahydro-4,7-epoxyazulen-5-yl 2-hydroxyacetate (Ik) in an embodiment of the invention. See FIG. 3.

General procedure H from (Id) (5 mg, 0.017 mmol) and 2-((tert-butyldiphenylsilyl)oxy)acetic acid (5.8 mg, 0.018 mmol) afforded the desired product as a colorless oil (3.2 mg, 53%, 2 steps) after deprotection of the TBDPS group and purification by silica flash chromatography (cyclohexane:EtOAc, 91:9 to 7:3).

$[\alpha]_D^{25}$=35.3 (c=0.1, CHCl$_3$). $^1$H-NMR (500 MHz, CDCl$_3$) δ 5.53-5.50 (m, 1H), 5.17 (dd, J=8.0, 2.5 Hz, 1H), 4.17 (d, J=5.4 Hz, 2H), 2.84-2.78 (m, 1H), 2.42 (dd, J=14.4, 8.0 Hz, 2H), 2.35-2.30 (m, 2H), 2.11 (s, 3H), 1.94-1.89 (m, 1H), 1.88-1.82 (m, 1H), 1.73 (ddd, J=14.5, 2.5, 1.4, 1H), 1.63 (s, 3H), 1.52-1.46 (m, 1H), 1.13 (s, 3H), 0.99 (d, J=6.8 Hz, 3H), 0.96 (d, J=7.0 Hz, 3H). $^{13}$C-NMR (126 MHz, CDCl$_3$) δ 173.1, 170.4, 134.2, 128.0, 86.7, 85.7, 77.2, 73.5, 60.8, 56.9, 39.7, 39.3, 32.0, 22.8, 21.4, 18.4, 18.0, 17.3, 13.7. HRMS-ESI calculated for $C_{19}H_{28}O_6Na$ (M+Na)$^+$: 375.1778; found: 375.1780.

Example 2-5

This example demonstrates the synthesis of (3aR,4S,5R,7R,8S)-5-(((S)-2-hydroxypropanoyl)oxy)-7-isopropyl-1,4-dimethyl-2,3,3a,4,5,6,7,8-octahydro-4,7-epoxyazulen-8-yl cinnamate (Il) in an embodiment of the invention. See FIG. 3.

General procedure H from (Ia) (16.3 mg, 0.043 mmol) and TBDPS-protected lactic acid (15.1 mg, 0.046 mmol) gave the named product as a colorless oil in 41% yield (7.9 mg) after deprotection with TBAF (1 M, 51 µL, 0.051 mmol) and acetic acid (51 µL, 0.89 mmol).

$[\alpha]_D^{25}$=−36.4 (c=0.18, CHCl$_3$). $^1$H-NMR (400 MHz, CDCl$_3$) δ 7.75 (d, J=16.0 Hz, 1H), 7.59-7.57 (m, 2H), 7.43-7.42 (m, 3H), 6.49 (d, J=16.0 Hz, 1H), 5.69 (bs, 1H), 5.17 (dd, J=8.0, 2.0 Hz, 1H), 4.33 (q, J=6.8 Hz, 1H), 2.89 (m, 1H), 2.57 (dd, J=14.4, 7.2 Hz, 1H), 2.45-2.40 (m, 1H), 2.37-2.31 (m, 1H), 1.99-1.89 (m, 2H), 1.77 (d, J=14.8 Hz, 1H), 1.63 (s, 3H), 1.56-1.48 (m, 1H), 1.46 (d, J=6.8 Hz, 3H), 1.20 (s, 3H), 1.03 (d, J=6.8 Hz, 3H), 1.01 (d, J=7.2 Hz, 3H). $^{13}$C-NMR (101 MHz, CDCl$_3$) δ 175.5, 166.3, 146.0, 134.6, 134.3, 130.8, 129.1, 128.4, 128.0, 117.7, 86.7, 85.8, 77.3, 73.4, 66.8, 56.9, 39.7, 39.6, 31.7, 22.9, 20.5, 18.5, 18.0, 17.2, 13.9. HRMS-ESI calculated for $C_{27}H_{34}O_6Na$ (M+Na)$^+$: 477.2248; found: 477.2265.

Example 2-6

This example demonstrates the synthesis of (3aR,4S,5R,7R,8S)-5-acetoxy-7-isopropyl-1,4-dimethyl-2,3,3a,4,5,6,7,8-octahydro-4,7-epoxyazulen-8-yl cinnamate (Im) in an embodiment of the invention. See FIG. 3.

To a solution of alcohol (Ia) (32.1 mg, 0.084 mmol) and pyridine (14 µL, 0.168 mmol) in dichloromethane (0.5 mL) was added acetic anhydride (16 µL, 0.168 mmol) at 0° C. After 3 h, the reaction was quenched with water and washed with aq. HCl and brine. Purification by silica chromatography (hexane:EtOAc, 4:1) yielded compound (Im) as a white solid (33.5 mg, 94%).

M.p.: 70-72° C. $[\alpha]_D^{25}$=−26.7 (c=0.2, CHCl$_3$). $^1$H-NMR (400 MHz, CDCl$_3$) δ 7.75 (d, J=16.0 Hz, 1H), 7.59-7.57 (m, 2H), 7.43-7.42 (m, 3H), 6.50 (d, J=16.0 Hz, 1H), 5.68 (bs, 1H), 5.11 (dd, J=8.0, 2.4 Hz, 1H), 2.87 (m, 1H), 2.53 (dd, J=14.0, 8.0 Hz, 1H), 2.45-2.30 (m, 2H), 2.09 (s, 3H), 1.96-1.89 (m, 2H), 1.78 (d, J=14.0 Hz, 1H), 1.63 (s, 3H), 1.61-1.51 (m, 1H), 1.19 (s, 3H), 1.04 (d, J=6.8 Hz, 3H), 1.00 (d, J=6.8 Hz, 3H). $^{13}$C-NMR (101 MHz, CDCl$_3$) δ 170.9, 166.3, 145.9, 134.3, 134.3, 130.7, 129.1, 128.3, 128.1, 117.8, 86.7, 85.8, 75.8, 73.4, 57.0, 39.7, 39.6, 32.2, 22.8, 21.3, 18.5, 18.1, 17.3, 13.9. HRMS-ESI calculated for $C_{26}H_{32}O_5Na$ (M+Na)$^+$: 447.2142; found: 447.2133.

Example 2-7

This example demonstrates the synthesis of (3aR,4S,5R, 7R,8S)-5-(((R)-2-((tert-butoxycarbonyl)amino)propanoyl) oxy)-7-isopropyl-1,4-dimethyl-2,3,3a,4,5,6,7,8-octahydro-4,7-epoxyazulen-8-yl cinnamate (In) in an embodiment of the invention. See FIG. 3.

Compound (In) was synthesized according to general procedure I from alcohol (Ia) (14.0 mg, 0.037 mmol) and BOC-D-alanine (6.9 mg, 0.037 mmol) in the presence of DMAP (8.9 mg, 0.073 mmol). The solution in toluene (1.4 mL) at 0° C. was treated with Et$_3$N (13 µL, 0.092 mmol) and 2,4,6-trichlorobenzoyl chloride (10 µL, 0.040 mmol). Chromatographic purification yielded the desired compound as a colorless oil (19.2 mg, 95%).

$[\alpha]_D^{25}$=−19.6 (c=0.12, CHCl$_3$). $^1$H-NMR (400 MHz, CDCl$_3$) δ 7.74 (d, J=16.0 Hz, 1H), 7.59-7.56 (m, 2H), 7.43-7.41 (m, 3H), 6.49 (d, J=16.0 Hz, 1H), 5.67 (bs, 1H), 5.16 (d, J=6.0 Hz, 1H), 5.01 (m, 1H), 4.34 (m, 1H), 2.87 (m, 1H), 2.52 (dd, J=14.4, 8.0 Hz, 1H), 2.41-2.29 (m, 2H), 1.96-1.87 (m, 2H), 1.81 (d, J=14.4 Hz, 1H), 1.62 (s, 3H), 1.60-1.50 (m, 1H), 1.47 (s, 9H), 1.43 (d, J=7.2 Hz, 3H), 1.18 (s, 3H), 1.04 (d, J=7.2 Hz, 3H), 1.00 (d, J=6.8 Hz, 3H). $^{13}$C-NMR (101 MHz, CDCl$_3$) 173.1, 166.3, 155.2, 146.0, 134.5, 134.3, 130.7, 129.1, 128.4, 128.0, 117.8, 86.7, 85.9, 80.0, 76.8, 73.4, 57.0, 49.6, 39.7, 39.5, 32.0, 28.5, 22.8, 18.8, 18.6, 18.1, 17.3, 13.9. HRMS-ESI calculated for $C_{32}H_{43}O_7Na$ (M+Na)$^+$: 576.2932; found: 576.2932.

Example 2-8

This example demonstrates the synthesis of (3aR,4S,5R, 7R,8S)-5-(glycyloxy)-7-isopropyl-1,4-dimethyl-2,3,3a,4,5, 6,7,8-octahydro-4,7-epoxyazulen-8-yl cinnamate (Io) in an embodiment of the invention. See FIG. 3.

The named compound was synthesized following the same procedure I from alcohol (Ia) (6 mg, 0.016 mmol) but using Fmoc-GlyOH (7 mg, 0.024 mmol) instead of the protected glycolic acid. The crude of the ester product was used directly for the Fmoc group deprotection (Atherton et al., *J. Chem. Soc. Perkin Trans.* 1 1981, 538-546), it was redissolved in CH$_2$Cl$_2$ (1 mL) and morpholine (1 mL, 11.5 mmol) was added. The reaction was left stirring at 23° C. for 3 h until completion. Solvent was evaporated and the crude purified by flash chromatography (SiO$_2$, cyclohexane:EtOAc, 9:1 to 1:1) giving the desired product as a pale yellow oil (31% 2 steps, 2.8 mg).

$[\alpha]_D^{25}$=−5.2 (c=0.15, CHCl$_3$). $^1$H-NMR (300 MHz, CDCl$_3$) δ 7.73 (d, J=16.0 Hz, 1H), 7.57-7.54 (m, 2H), 7.43-7.37 (m, 3H), 6.47 (d, J=16.0 Hz, 1H), 5.65 (bs, 1H), 5.14 (dd, J=7.9, 2.6 Hz, 1H), 3.75 (bs, 2H), 3.48 (bs, 2H), 2.89-2.81 (m, 1H), 2.50 (dd, J=14.3, 8.0 Hz, 1H), 2.42-2.24 (m, 2H), 1.95-1.89 (m, 2H), 1.77 (d, J=14.5 Hz, 1H), 1.60 (s, 3H), 1.50-1.44 (m, 1H), 1.16 (s, 3H), 1.01 (d, J=6.8 Hz, 3H), 0.98 (d, J=7.1 Hz, 3H). $^{13}$C-NMR (101 MHz, CDCl$_3$) 170.5, 166.3, 146.0, 134.5, 134.3, 130.8, 129.1, 128.4, 128.1, 117.7, 86.8, 85.9, 76.2, 73.4, 57.0, 53.9, 39.8, 32.1, 29.9, 22.8, 18.6, 18.1, 17.4, 14.0. HRMS-ESI calculated for $C_{24}H_{29}O_3(M-C_2H_4NO_2)^+$: 365.2111; found: 365.2117.

Example 2-9

This example demonstrates the synthesis of (3aR,4S,5R, 7R,8S)-5-((L-alanyl)oxy)-7-isopropyl-1,4-dimethyl-2,3,3a, 4,5,6,7,8-octahydro-4,7-epoxyazulen-8-yl cinnamate (Ip) in an embodiment of the invention. See FIG. 3.

General procedure H for the ester formation was adapted for the synthesis of (Ip) using alcohol (Ia) (6 mg, 0.016 mmol) and commercially available Fmoc-AlaOH (7.3 mg, 0.024 mmol). For Fmoc group deprotection (Atherton et al., *J. Chem. Soc. Perkin Trans.* 1 1981, 538-546) the product from the ester formation reaction was dissolved in CH$_2$Cl$_2$ (1 mL) and morpholine (1 mL, 11.5 mmol) was added. The reaction was stirred at 23° C. for 3 h until complete Fmoc removal was observed by TLC. Then the reaction was concentrated under vacuum and the pure product was produced as a pale yellow oil (26% 2 steps, 2.8 mg) after purification by silica chromatography (cyclohexane:EtOAc, 9:1 to 1:1).

$[\alpha]_D^{25}$=−5.9 (c=0.10, CHCl$_3$). $^1$H-NMR (400 MHz, CDCl$_3$) δ 7.72 (d, J=16.0 Hz, 1H), 7.58-7.53 (m, 2H), 7.42-7.38 (m, 3H), 6.47 (d, J=16.0 Hz, 1H), 5.66 (bs, 1H), 5.09 (dd, J=7.9, 2.5 Hz, 1H), 3.58 (q, J=7.1 Hz, 1H), 2.89-2.83 (m, 1H), 2.53 (dd, J=14.4, 7.9 Hz, 1H), 2.43-2.37 (m, 1H), 2.35-2.27 (m, 1H), 1.95-1.87 (m, 2H), 1.76-1.69 (m, 1H), 1.60 (s, 3H), 1.55-1.45 (m, 1H), 1.36 (d, J=7.0 Hz, 3H), 1.18 (s, 3H), 1.01 (d, J=6.8 Hz, 3H), 0.98 (d, J=7.0 Hz, 3H). $^{13}$C-NMR (101 MHz, CDCl$_3$) 176.2, 166.3, 146.0, 134.5, 134.3, 130.8, 129.1, 128.4, 128.1, 117.8, 86.8, 85.8, 76.4, 73.4, 57.0, 50.2, 39.7, 31.9, 29.9, 22.9, 20.8, 18.6, 18.0, 17.3, 13.9. HRMS-ESI calculated for $C_{27}H_{35}NO_5$ (M+H)$^+$: 454.2588; found: 454.2581.

Example 2-10

This example demonstrates the synthesis of (3aR,4S,5R, 7R,8S)-7-cyclohexyl-5-(2-hydroxyacetoxy)-1,4-dimethyl-2,3,3a,4,5,6,7,8-octahydro-4,7-epoxyazulen-8-yl cinnamate (Iq) in an embodiment of the invention. See FIG. 3.

The desired product was obtained as colorless oil (12 mg, 66%, 2 steps) according to the general procedure H from (Ie) (16 mg, 0.04 mmol) and 2-((tert-butyldiphenylsilyl)oxy) acetic acid (17 mg, 0.05 mmol). HPLC analysis showed a final enantiomeric ratio of 9:1 (Agilent HPLC 1200, ChiralPack IC, room temperature 7.68 min (major), 9.74 min (minor) (Agilent Technologies, Santa Clara, Calif.)).

$[\alpha]_D^{25}$=−12.9 (c=0.22, CHCl$_3$). $^1$H-NMR (400 MHz, CDCl$_3$) δ 7.73 (d, J=16.0 Hz, 1H), 7.59-7.55 (m, 2H), 7.43-7.39 (m, 3H), 6.48 (d, J=16.0 Hz, 1H), 5.68-5.63 (m, 1H), 5.20 (dd, J=7.9, 2.5 Hz, 1H), 4.19 (s, 2H), 2.87-2.83 (m, 1H), 2.51 (dd, J=14.4, 7.9 Hz, 1H), 2.45-2.26 (m, 3H), 1.96-1.87 (m, 1H), 1.85-1.70 (m, 4H), 1.60 (s, 3H), 1.56-1.47 (m, 2H), 1.25-1.18 (m, 5H), 1.15 (s, 3H), 1.14-1.05 (m, 2H). $^{13}$C-NMR (101 MHz, CDCl$_3$) δ 177.2, 166.4, 146.1, 134.6, 134.3, 130.8, 129.1, 128.4, 127.9, 117.7, 86.7, 85.8, 77.4, 73.1, 60.8, 56.9, 42.9, 39.8, 39.3, 28.3, 27.2, 27.1, 27.1, 26.5, 22.8, 18.5, 13.9. HRMS-ESI calculated for $C_{29}H_{36}O_6Na$ (M+Na)$^+$: 503.2404; found: 503.2394.

Example 2-11

This example demonstrates the synthesis of (3aR,4S,5R, 7R,8S)-5-(2-hydroxyacetoxy)-1,4-dimethyl-7-phenyl-2,3, 3a,4,5,6,7,8-octahydro-4,7-epoxyazulen-8-yl cinnamate (Ir) in an embodiment of the invention. See FIG. 3.

General procedure H from (3aR,4S,5R,7R,8S)-5-hydroxy-1,4-dimethyl-7-phenyl-2,3,3a,4,5,6,7,8-octahydro-4, 7-epoxyazulen-8-yl cinnamate, (If) (8 mg, 0.02 mmol) and 2-((tert-butyldiphenylsilyl)oxy)acetic acid (9 mg, 0.03 mmol) furnished a white gum after purification by silica chromatography (cyclohexane:EtOAc 95:5 to 8:2, 5 mg, 38% 2 steps). HPLC analysis showed a final enantiomeric ratio of 91:9 (Agilent HPLC 1200, ChiralPack IC, room temperature 10.02 min (major), 13.71 min (minor) (Agilent Technologies, Santa Clara, Calif.)).

$[\alpha]_D^{25}$=78.2 (c=0.10, CHCl$_3$). $^1$H-NMR (400 MHz, CDCl$_3$) δ 7.56 (d, J=16.2 Hz, 1H), 7.53-7.50 (m, 2H), 7.42-7.38 (m, 5H), 7.31-7.26 (m, 2H), 7.25-7.21 (m, 1H), 6.32 (d, J=16.0 Hz, 1H), 5.58-5.57 (m, 1H), 5.37 (dd, J=8.0, 3.0 Hz, 1H), 4.16 (s, 2H), 3.17 (dd, J=13.9, 8.0 Hz, 1H), 3.12-3.05 (m, 1H), 2.50-2.41 (m, 2H), 2.37-2.28 (m, 1H), 2.14 (ddd, J=13.9, 3.0, 1.4 Hz, 1H), 2.08-1.99 (m, 1H), 1.70 (s, 3H), 1.68-1.61 (m, 1H), 1.30 (s, 3H). $^{13}$C-NMR (101 MHz, CDCl$_3$) δ 173.2, 165.4, 145.6, 141.0, 135.5, 134.3, 130.7, 129.1, 128.3, 128.1, 127.8, 127.2, 126.3, 117.4, 86.9, 85.2, 76.7, 76.2, 60.8, 56.7, 41.6, 39.5, 27.1, 23.0, 18.7, 14.2. HRMS-ESI calculated for C$_{29}$H$_{30}$O$_6$Na (M+Na)$^+$: 497.1935; found: 497.1917.

Example 2-12

This example demonstrates the synthesis of (3aR,4S,5R,7R,8S)-7-cyclopropyl-5-(2-hydroxyacetoxy)-1,4-dimethyl-2,3,3a,4,5,6,7,8-octahydro-4,7-epoxyazulen-8-yl cinnamate (Is) in an embodiment of the invention. See FIG. 3.

Compound (Is) was produced as a colorless oil in 78% yield (9 mg, 2 steps) following general procedure H from (Ig) (10 mg, 0.03 mmol) and 2-((tert-butyldiphenylsilyl)oxy)acetic acid (12.4 mg, 0.04 mmol).

$[\alpha]_D^{25}$=−24.9 (c=0.18, CHCl$_3$). $^1$H-NMR (400 MHz, CDCl$_3$) δ 7.77 (d, J=16.0 Hz, 1H), 7.62-7.52 (m, 2H), 7.51-7.38 (m, 3H), 6.53 (d, J=16.0 Hz, 1H), 5.71-5.58 (m, 1H), 5.23 (dd, J=8.0, 2.9 Hz, 1H), 4.20 (bs, 2H), 2.94-2.82 (m, 1H), 2.50 (dd, J=14.1, 8.0 Hz, 1H), 2.43-2.31 (m, 2H), 1.96-1.87 (m, 1H), 1.70 (s, 3H), 1.58-1.46 (m, 2H), 1.49-1.35 (m, 1H), 1.16 (s, 3H), 1.16-1.08 (m, 1H), 0.59-0.49 (m, 1H), 0.49-0.31 (m, 3H). $^{13}$C-NMR (126 MHz, CDCl$_3$) δ 173.2, 166.4, 145.8, 134.9, 134.3, 130.7, 129.1, 128.4, 127.4, 117.8, 86.4, 83.3, 76.7, 75.7, 60.8, 56.8, 39.4, 38.6, 23.1, 18.5, 14.5, 14.2, 1.5, 0.9. HRMS-ESI calculated for C$_{26}$H$_{30}$O$_6$Na (M+Na)$^+$: 461.1935; found: 461.1927.

Example 3

This example illustrates that compounds of the invention inhibit human cancer cell growth.

Samples were tested in the standard National Cancer Institute 60-cell line protocol. First, they were tested against all 60 cell lines in a single final concentration of 10 micromolar. Then, they were separately tested in five 10-fold dilutions. The drug exposure was two days, with an SRB endpoint. The results are set forth in Table 1.

TABLE 1

Potency of several compounds of formula (I) in cancer cell lines within the NCI 60 cell assay (GI$_{50}$ values μM).

| Cell Line | (Ih) GI-50 value μM | (Il) GI-50 value μM | (Im) GI-50 value μM | (Ij) GI-50 value μM | (Iq) GI-50 value μM | (Is) GI-50 value μM | (Ir) GI-50 value μM |
|---|---|---|---|---|---|---|---|
| LEUKEMIA | | | | | | | |
| CCRF-CEM | 42 | 16 | 32 | 18 | 15 | 19 | 20 |
| HL-60(TB) | 35 | 11 | 25 | 14 | 15 | 12 | 16 |
| K-562 | 38 | 15 | 34 | 15 | 13 | 20 | 16 |
| MOLT-4 | 40 | 10 | 27 | 9 | 12 | 16 | 12 |
| RPMI-8226 | 27 | 8 | 10 | 13 | 10 | 20 | 13 |
| SR | 32 | 13 | 32 | 14 | 9 | 17 | 11 |
| NSCLC | | | | | | | |
| A549/ATCC | 33 | 13 | 47 | 13 | 11 | 14 | 15 |
| EKVX | n.t. | 10 | 20 | 13 | 11 | 14 | 15 |
| HOP-62 | 36 | 15 | 89 | 17 | 14 | 16 | 18 |
| HOP-92 | 100 | 6 | n.t. | 13 | 6 | 17 | 14 |
| NCI-H226 | 35 | 11 | 29 | 17 | 12 | 17 | 16 |
| NCI-H23 | 42 | 14 | 35 | 15 | 14 | 17 | 17 |
| NCI-H322M | 43 | 19 | 100 | 19 | 17 | 17 | 22 |
| NCI-H460 | 37 | 15 | 31 | 16 | 13 | 18 | 15 |
| NCI-H522 | 40 | 13 | 21 | 13 | 15 | 17 | 17 |
| COLON | | | | | | | |
| COLO 205 | 44 | 17 | 32 | 17 | 15 | 19 | 15 |
| HCC-2998 | 100 | 14 | 68 | 14 | 13 | 17 | 15 |
| HCT-116 | 33 | 12 | 16 | 19 | 9 | 16 | 15 |
| HCT-15 | 32 | 12 | 32 | 13 | 10 | 14 | 13 |
| HT29 | 39 | 14 | 31 | 13 | 12 | 17 | 16 |
| KM12 | 40 | 16 | 40 | 13 | 14 | 17 | 16 |
| SW-620 | 40 | 15 | 39 | 17 | 14 | 20 | 21 |
| CNS | | | | | | | |
| SF-268 | 2.6 | 1.3 | 35 | 14 | 0.7 | 1.6 | 1.4 |
| SF-295 | 40 | 11 | 39 | 13 | 12 | 17 | 14 |
| SF-539 | 40 | 15 | 100 | 17 | 17 | 17 | 18 |

TABLE 1-continued

Potency of several compounds of formula (I) in cancer cell lines within the NCI 60 cell assay (GI$_{50}$ values µM).

| Cell Line | Compound (Ih) GI-50 value µM | (Il) GI-50 value µM | (Im) GI-50 value µM | (Ij) GI-50 value µM | (Iq) GI-50 value µM | (Is) GI-50 value µM | (Ir) GI-50 value µM |
|---|---|---|---|---|---|---|---|
| SNB-19 | 39 | 18 | 85 | 17 | 17 | 19 | 22 |
| SNB-75 | 2.9 | 24 | 28 | 15 | 14 | 13 | 15 |
| U251 | 35 | 14 | 48 | 15 | 13 | 15 | 13 |
| MELANOMA | | | | | | | |
| LOX IMVI | 42 | 15 | 30 | 15 | 14 | 17 | 17 |
| MALME-3M | 43 | 15 | 39 | 17 | 17 | 16 | 20 |
| M14 | 43 | 13 | 40 | 13 | 15 | 17 | 17 |
| MDA-MB-435 | 43 | 15 | 39 | 15 | 15 | 17 | 17 |
| SK-MEL-2 | 44 | 15 | 100 | 16 | 17 | 19 | 16 |
| SK-MEL-28 | 42 | 16 | 69 | 17 | 17 | 18 | 18 |
| SK-MEL-5 | 35 | 13 | 22 | 16 | 14 | 18 | 15 |
| UACC-257 | 40 | 15 | 28 | 16 | 14 | 16 | 19 |
| UACC-62 | 100 | 13 | 26 | 12 | 15 | 15 | 15 |
| OVARIAN | | | | | | | |
| IGROV1 | 46 | 19 | 100 | 19 | 19 | 19 | 24 |
| OVCAR-3 | 39 | 13 | 22 | 14 | 13 | 16 | 15 |
| OVCAR-4 | 35 | 12 | 11 | 14 | 15 | 15 | 15 |
| OVCAR-5 | 41 | 18 | 100 | 20 | 19 | 17 | 22 |
| OVCAR-8 | 0.09 | 0.35 | 9 | 13 | 0.10 | 0.054 | 0.26 |
| NCI/ADR-RES | 0.13 | 0.42 | 23 | 12 | 0.25 | 0.071 | 0.34 |
| SK-OV-3 | 44 | 15 | 71 | 17 | 13 | 16 | 19 |
| RENAL | | | | | | | |
| 786-0 | 35 | 13 | 85 | 15 | 13 | 13 | 14 |
| A498 | 0.034 | 0.21 | 2.2 | 0.27 | 0.021 | 0.11 | 0.089 |
| ACHN | 0.022 | 0.09 | 4.5 | 1.4 | 0.035 | 0.028 | 0.035 |
| CAKI-1 | 1.07 | 7.2 | 13 | 12 | 10 | 11 | 13 |
| RXF 393 | 0.13 | 0.045 | 8.9 | 0.069 | 0.025 | 0.014 | 0.027 |
| SN12C | 20 | 0.21 | 10 | 7.4 | 0.060 | 0.052 | 11 |
| TK-10 | 100 | 17 | 93 | 17 | 17 | 19 | 23 |
| UO-31 | 0.040 | 0.71 | 20 | 11 | 0.46 | 0.33 | 0.55 |
| PROSTATE | | | | | | | |
| PC-3 | 26 | 4 | 8 | 9 | 12 | 15 | 10 |
| DU-145 | 41 | 17 | 71 | 16 | 13 | 18 | 17 |
| BREAST | | | | | | | |
| MCF7 | 32 | 10 | 19 | 8.9 | 4.5 | 13 | 10 |
| MDA-MB-231/ATCC | 39 | 15 | 49 | 15 | 18 | 18 | 19 |
| HS 578T | 0.015 | 0.098 | 4.8 | 0.15 | 0.030 | 0.023 | 0.033 |
| BT-549 | 0.14 | 1.4 | 51 | 14 | 0.50 | 0.21 | 0.71 |
| T-47D | 27 | 7.2 | 20 | 4.6 | 9.1 | 14 | 11 |
| MDA-MB-468 | 33 | 11 | 24 | 13 | 12 | 15 | 15 |

Example 4

This example illustrates some of the properties of the compounds of formula (I) in accordance with an embodiment of the invention. FIGS. 4-8 depict the dose response curves for certain compounds of formula (I) against various cancer cell lines in a 60-cell test, showing that the compound is active against a number of leukemia, non-small cell, colon cancer, melanoma, prostate, renal, breast, ovarian, and CNS cancer cell lines.

FIGS. 4A-4I are the dose response curves for (Ih).
FIGS. 5A-5I are the dose response curves for (Ij).
FIGS. 6A-6I are the dose response curves for (Is).
FIGS. 7A-7I are the dose response curves for (Iq).
FIGS. 8A-8I are the dose response curves for (Ir).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I)

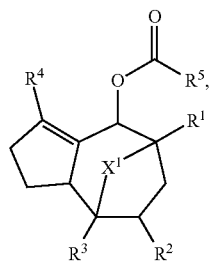

(I)

wherein
- $R^1$ is selected from $C_1$-$C_6$ alkyl, $C_2$-$C_6$ alkenyl, $C_3$-$C_6$ cycloalkyl, aryl, and heteroaryl, each of which is optionally substituted;
- $R^2$ is selected from hydroxy, alkoxy, $X^2$—(CX$^3$)—(CR$^6$R$^7$)$_m$—X$^2$—(CX$^3$)—R$^8$, —X$^2$—(CX$^3$)—(CR$^6$R$^7$)$_m$—R$^8$, and —X$^2$—(CX$^3$)—(CR$^6$R$^7$)$_m$—X$^2$—R$^{18}$;
- $R^6$ and $R^7$ are independently selected from hydrogen, hydroxy, fluorine, chlorine, and $C_1$-$C_6$ alkyl;
- $R^8$ is selected from $C_1$-$C_6$ alkyl, fluoro $C_1$-$C_6$ alkyl, heterocycloalkyl, aryl, heteroaryl, alkoxy, aryloxy, each of the foregoing is optionally substituted, hydroxy, and —NR$^{15}$R$^{16}$;
- $R^{15}$ and $R^{16}$ are independently selected from hydrogen and $C_1$-$C_6$ alkyl; or
- $R^{16}$ is COOR$^{17}$;
- $R^{17}$ is $C_1$-$C_6$ alkyl;
- $R^{18}$ is selected from $C_1$-$C_6$ alkyl, fluoro $C_1$-$C_6$ alkyl, aryl, and heteroaryl, each of which is optionally substituted;
- each $X^2$ is independently selected from O, S and NR$^{15}$;
- $X^3$ is selected from O and S;
- $R^3$ and $R^4$ are independently a $C_1$-$C_6$ alkyl;
- $R^5$ is selected from —(CR$^9$R$^{10}$)$_n$—R$^{11}$ and —(CR$^{12}$=cR$^{13}$)$_n$—R$^{14}$;
- $R^9$ and $R^{10}$ are independently selected from hydrogen and $C_1$-$C_6$ alkyl; or alternatively
- $R^9$ and $R^{10}$, together with the carbon to which they are attached, form a $C_3$-$C_6$ cycloalkyl;
- $R^{11}$ and $R^{14}$ are independently selected from $C_1$-$C_6$ alkyl, $C_3$-$C_6$ cycloalkyl, aryl, and heteroaryl, each of which is optionally substituted;
- $R^{12}$ and $R^{13}$ are independently selected from hydrogen, halogen, and $C_1$-$C_6$ alkyl;
- $X^1$ is selected from O, NR$^{15}$ and S; and
- n and m are independently selected from 0 and an integer of 1-3, or a stereoisomer or a pharmaceutically acceptable salt thereof.

2. The compound of claim 1, wherein $R^1$ is selected from isopropyl, tert-butyl, $C_3$-$C_6$ cycloalkyl, and phenyl, and $X^1$ is O, or a stereoisomer or a pharmaceutically acceptable salt thereof.

3. The compound of claim 1, wherein $R^2$ is hydroxy, or a stereoisomer or a pharmaceutically acceptable salt thereof.

4. The compound of claim 1, wherein $R^2$ is $X^2$—C(O)—(CR$^6$R$^7$)$_m$—R$^8$; wherein
- $R^6$ is hydrogen;
- $R^7$ is selected from hydrogen and $C_1$-$C_6$ alkyl;
- $R^8$ is selected from $C_1$-$C_6$ alkyl, hydroxy, —NH$_2$, —NH-Boc, and —NHCOOR$^{17}$;
- $R^{17}$ is $C_1$-$C_6$ alkyl;
- $X^2$ is O; and
- m is 0 or 1, or a stereoisomer or a pharmaceutically acceptable salt thereof.

5. The compound of claim 1, wherein $R^5$ is —(CR$^9$R$^{10}$)$_n$—R$^{11}$, $R^9$ and $R^{10}$ are each hydrogen, $R^{11}$ is phenyl, and n is 1-3, or a stereoisomer or a pharmaceutically acceptable salt thereof.

6. The compound of claim 1, wherein $R^5$ is —(CR$^9$R$^{10}$)$_n$—R$^{11}$, n is 0, and $R^{11}$ is $C_1$-$C_6$ alkyl, or a stereoisomer or a pharmaceutically acceptable salt thereof.

7. The compound of claim 1, wherein $R^5$ is —(CR$^9$R$^{10}$)$_n$—R$^{11}$, $R^9$ and $R^{10}$, together with the carbon to which they are attached, form a $C_3$-$C_6$ cycloalkyl, $R^{11}$ is phenyl, and n is 1-3, or a stereoisomer or a pharmaceutically acceptable salt thereof.

8. The compound of claim 1, wherein $R^5$ is —(CR$^{12}$=CR$^{13}$)$_n$—R$^{14}$, $R^{12}$ and $R^{13}$ are each hydrogen, $R^{14}$ is phenyl, and n is 1-3, or a stereoisomer or a pharmaceutically acceptable salt thereof.

9. The compound of claim 1, wherein $R^3$ is methyl, or a stereoisomer or a pharmaceutically acceptable salt thereof.

10. The compound of claim 1, wherein $R^4$ is methyl, or a stereoisomer or a pharmaceutically acceptable salt thereof.

11. The compound of claim 1 that is selected from the group consisting of

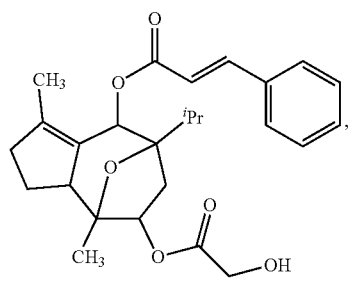
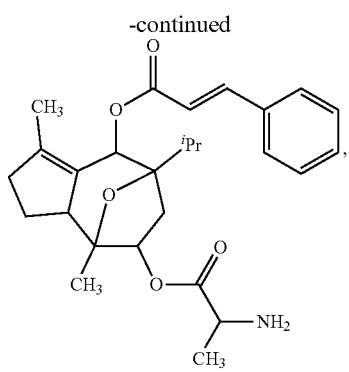
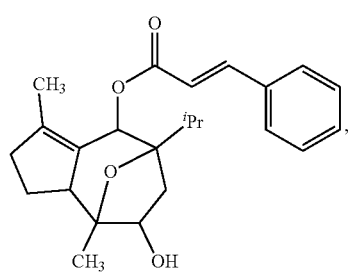
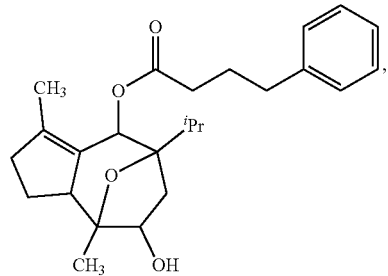
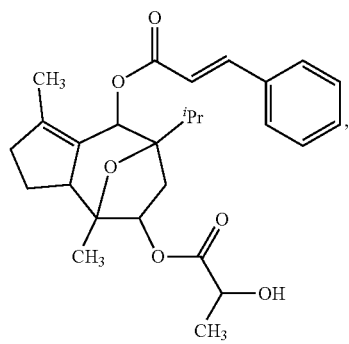
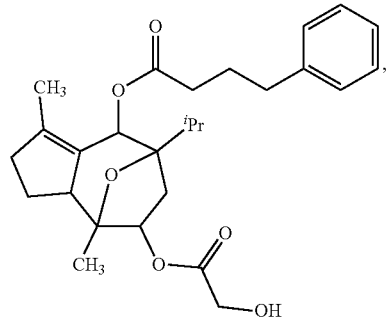
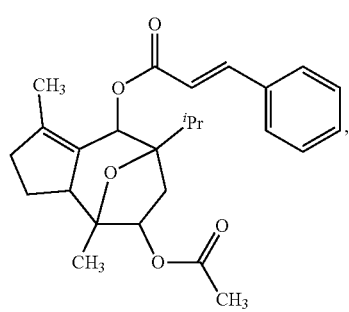
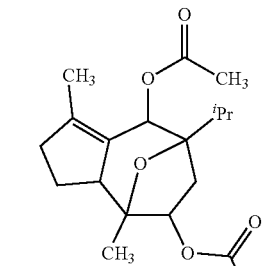
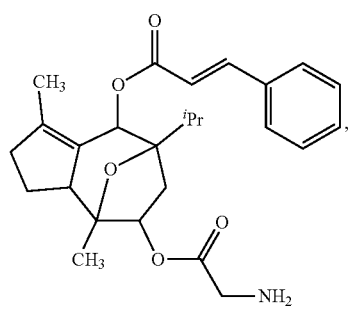
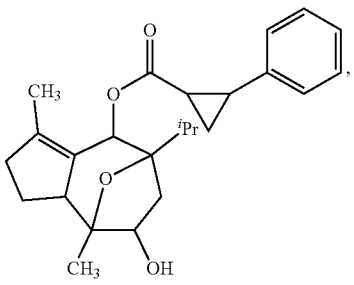

-continued
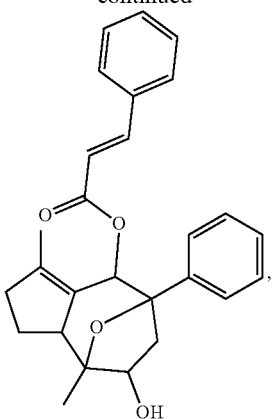
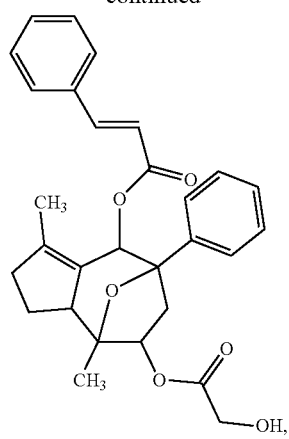
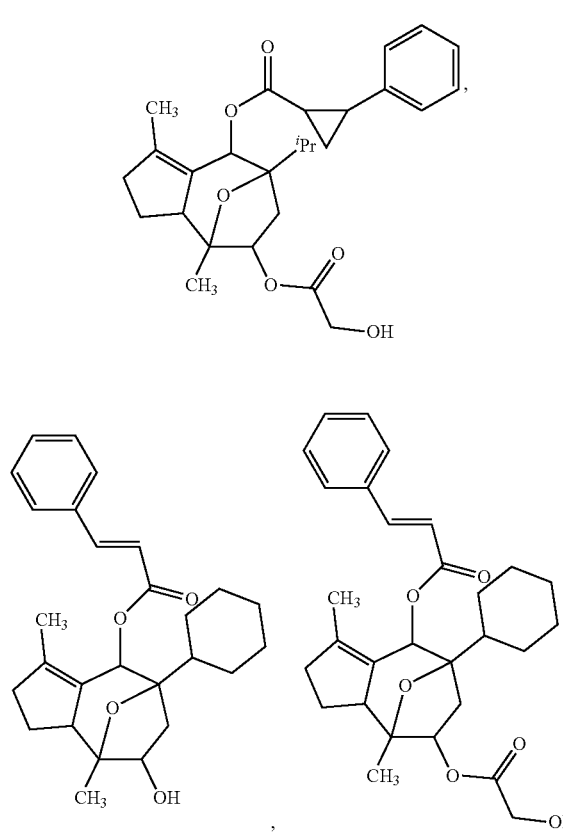
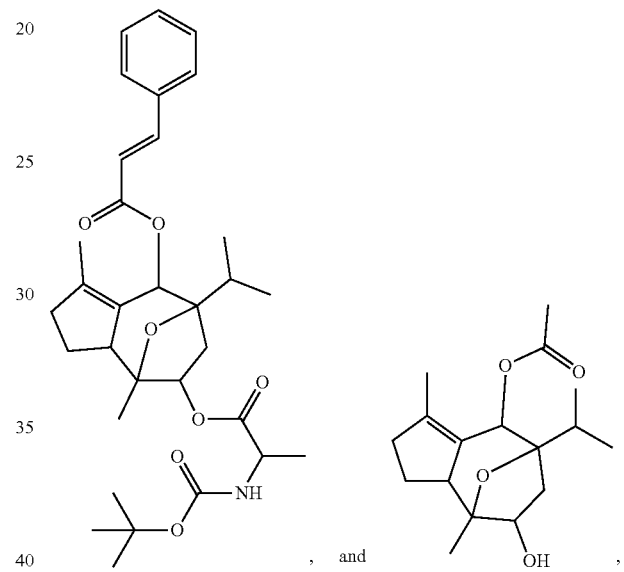
, and
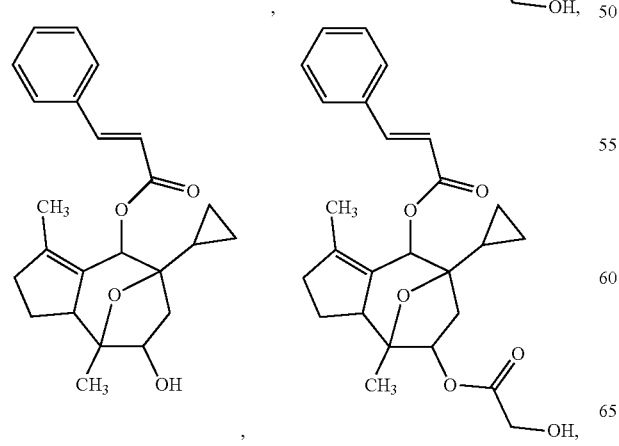
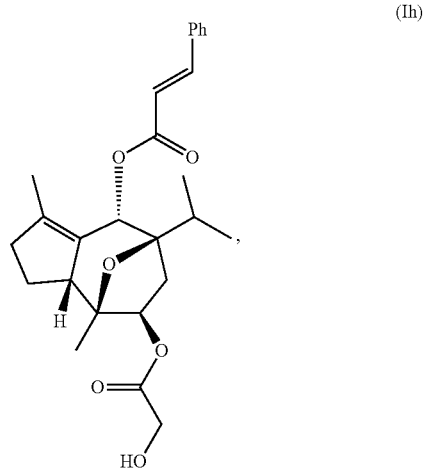
or a stereoisomer or a pharmaceutically acceptable salt thereof.
12. The compound of claim 1 that is selected from the group consisting of
(Ih)

(Ij) 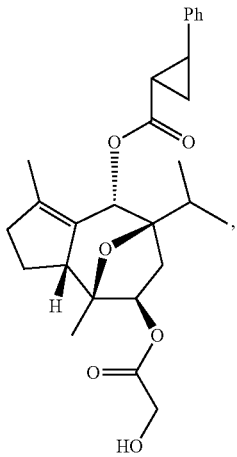

(Il) 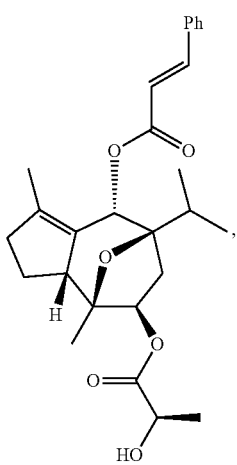

(Im) 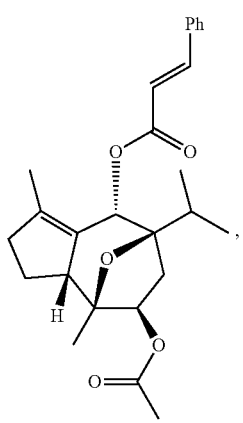

(Iq) 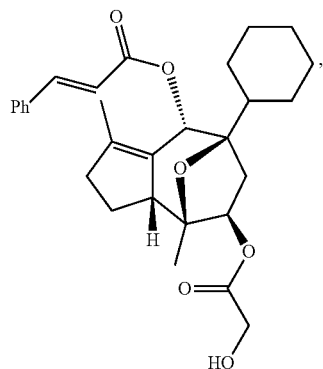

(Ir) 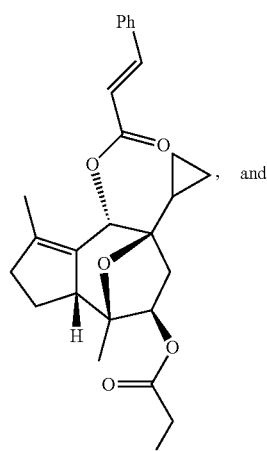, and (Is) 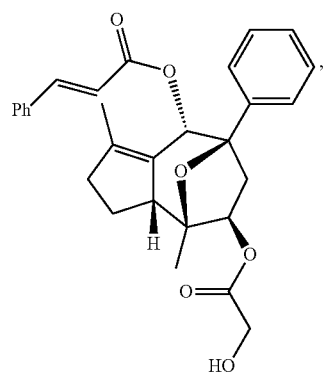

or a pharmaceutically acceptable salt thereof.

13. A pharmaceutical composition comprising a pharmaceutically acceptable carrier and a compound of claim 1 or a stereoisomer or a pharmaceutically acceptable salt thereof.

14. A method of treating cancer in a subject comprising administering an effective amount of a compound of claim 1 or a stereoisomer or a pharmaceutically acceptable salt thereof to the subject.

15. The method of claim 14, wherein the cancer is selected from the group consisting of leukemia, non-small cell lung cancer, colon cancer, melanoma, prostate cancer, renal cancer, breast cancer, CNS cancer, ovarian cancer, and Ewing's sarcoma.

16. The method of claim 15, wherein the cancer is renal cancer.

17. The method of claim 15, wherein the cancer is Ewing's sarcoma.

18. The method of claim 15, wherein the cancer is prostate cancer.
19. The compound of claim 1, wherein the compound of formula (I) has the stereochemistry of formula (I'):
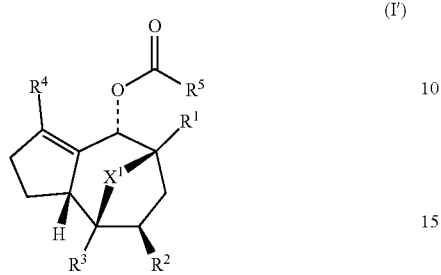
(I')
or a pharmaceutically acceptable salt thereof.
* * * * *